(12) United States Patent
Nash et al.

(10) Patent No.: US 8,974,362 B2
(45) Date of Patent: *Mar. 10, 2015

(54) CENTRIFUGE

(71) Applicant: Kensey Nash Corporation, Exton, PA (US)

(72) Inventors: John E. Nash, Chester Springs, PA (US); William T. Fisher, Schwenksville, PA (US)

(73) Assignee: Kensey Nash Corporation, Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/294,302

(22) Filed: Jun. 3, 2014

(65) Prior Publication Data

US 2014/0287903 A1 Sep. 25, 2014

Related U.S. Application Data

(63) Continuation of application No. 13/766,528, filed on Feb. 13, 2013, which is a continuation-in-part of application No. 13/447,008, filed on Apr. 13, 2012, now Pat. No. 8,394,006, which is a (Continued)

(51) Int. Cl.
*B04B 1/14* (2006.01)
*A61M 1/36* (2006.01)

(Continued)

(52) U.S. Cl.
CPC .............. *A61M 1/3696* (2014.02); *B04B 1/14* (2013.01); *B04B 1/02* (2013.01); *B04B 5/0407* (2013.01);

(Continued)

(58) Field of Classification Search
CPC ...... B04B 1/14; B04B 5/0407; B04B 5/0442; B04B 11/05

USPC ............ 494/2, 3, 10, 26, 43, 45, 56; 422/533, 422/548; 604/6.01–6.06; 210/782

See application file for complete search history.

(56) References Cited

U.S. PATENT DOCUMENTS

| 347,702 A | 8/1886 | Evans |
| 1,429,320 A | 9/1922 | Bouillon |

(Continued)

FOREIGN PATENT DOCUMENTS

| DE | 1179025 B | 10/1964 |
| DE | 102010003223 A1 | 9/2011 |

(Continued)

OTHER PUBLICATIONS

International Search Report dated May 30, 2012 re Application No. PCT/US2011/001922.

(Continued)

*Primary Examiner* — Timothy Cleveland
(74) *Attorney, Agent, or Firm* — Caesar, Rivise, Berstein, Cohen & Pokotilow, Ltd.

(57) ABSTRACT

Centrifuges are useful to, among other things, remove red blood cells from whole blood and retain platelets and other factors in a reduced volume of plasma. Platelet rich plasma (PRP) and or platelet poor plasma (PPP) can be obtained rapidly and is ready for immediate injection into the host. Embodiments may include valves, operated manually or automatically, to open ports that discharge the excess red blood cells and the excess plasma into separate receivers while retaining the platelets and other factors in the centrifuge chamber. High speeds used allow simple and small embodiments to be used at the patient's side during surgical procedures. The embodiments can also be used for the separation of liquids or slurries in other fields such as, for example, the separation of pigments or lubricants.

22 Claims, 38 Drawing Sheets

Figure 2:
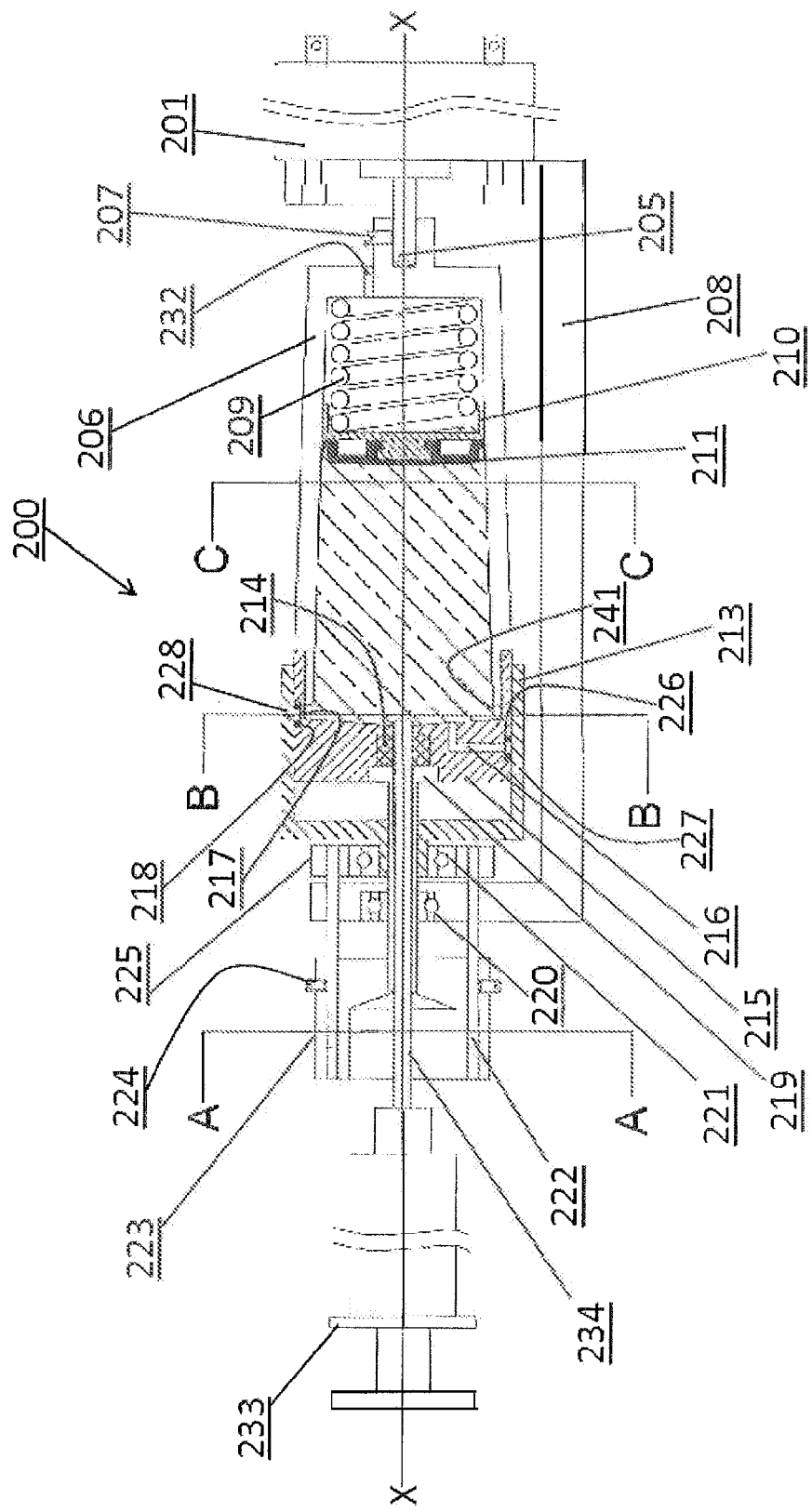
Figure 3:
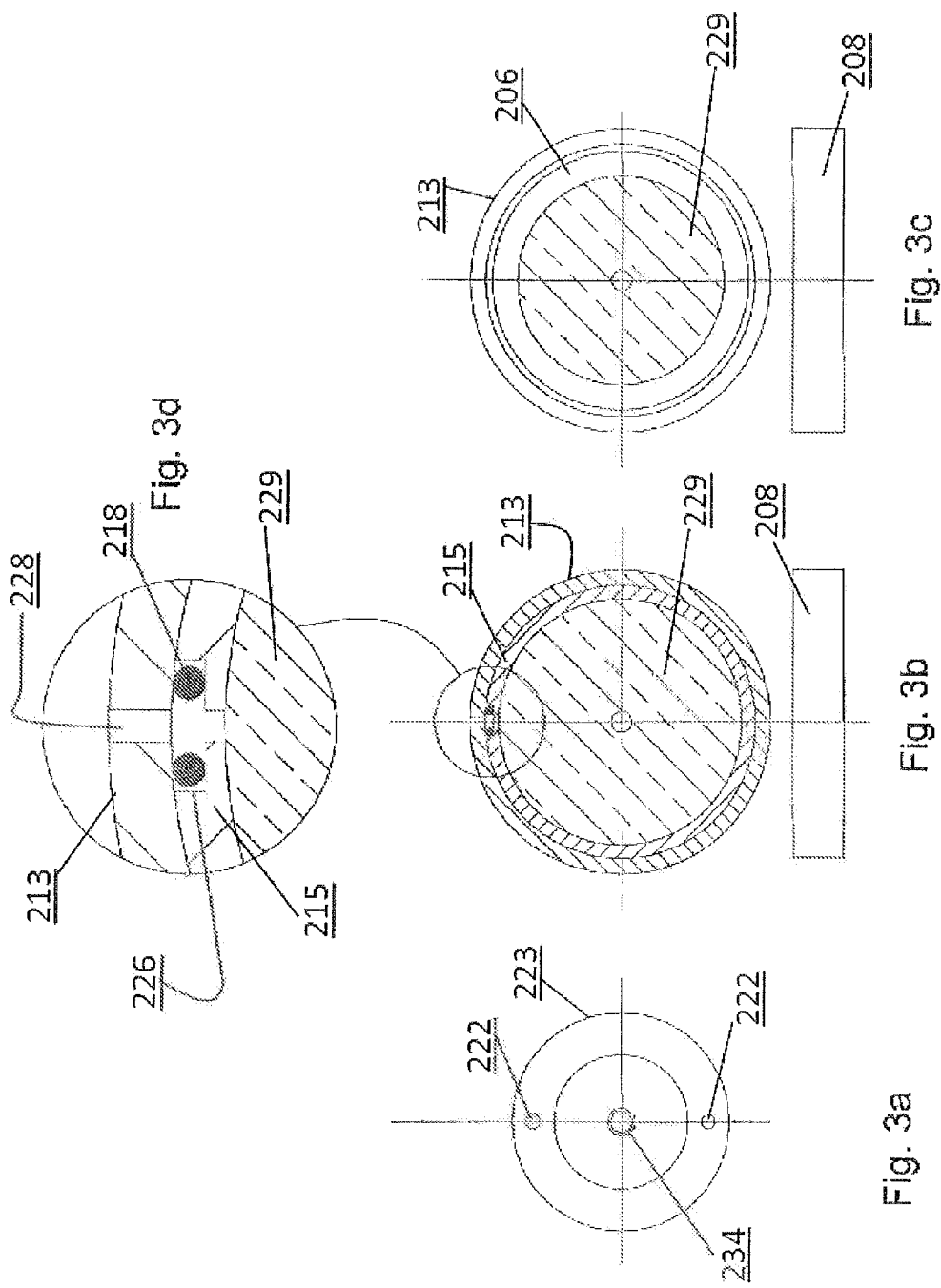

Related U.S. Application Data continuation-in-part of application No. 13/396,600, filed on Feb. 15, 2012, now Pat. No. 8,556,794, which is a continuation-in-part of application No. PCT/US2011/001922, filed on Nov. 19, 2011, which is a continuation-in-part of application No. 12/949,781, filed on Nov. 19, 2010, now Pat. No. 8,317,672, which is a continuation-in-part of application No. 13/209,226, filed on Aug. 12, 2011, now Pat. No. 8,469,871, which is a continuation-in-part of application No. 12/949,781, filed on Nov. 19, 2010, now Pat. No. 8,317,672.

(51) Int. Cl.

| | | |
|---|---|---|
| *B04B 1/02* | (2006.01) | |
| *B04B 5/04* | (2006.01) | |
| *B04B 7/08* | (2006.01) | |
| *B04B 11/04* | (2006.01) | |
| *B04B 1/18* | (2006.01) | |
| *B01D 21/26* | (2006.01) | |
| *B01D 21/34* | (2006.01) | |

(52) U.S. Cl.
CPC ............... *B04B 5/0442* (2013.01); *B04B 7/08* (2013.01); *B04B 11/04* (2013.01); *B04B 2005/0485* (2013.01); *A61M 1/3693* (2013.01); *B04B 1/18* (2013.01); *B01D 21/262* (2013.01); *B01D 21/34* (2013.01); *B01D 2221/10* (2013.01)
USPC ........ 494/37; 494/3; 494/26; 494/43; 422/533

(56) References Cited

U.S. PATENT DOCUMENTS

| | | |
|---|---|---|
| 1,921,181 A | 8/1933 | Fawcett |
| 2,023,762 A | 12/1935 | Fawcett |
| 2,136,127 A | 11/1938 | Fawcett |
| 2,596,616 A | 5/1952 | Strezynski |
| 2,822,126 A | 2/1958 | Cohn et al. |
| 2,822,315 A | 2/1958 | Cohn et al. |
| 2,873,910 A | 2/1959 | Steinacker |
| 2,906,450 A | 9/1959 | Lang et al. |
| 2,906,451 A | 9/1959 | Tullis et al. |
| 2,906,452 A | 9/1959 | Tullis |
| 2,940,662 A | 6/1960 | Applegate |
| 3,085,407 A | 4/1963 | Tomlinson |
| 3,092,582 A | 6/1963 | Lacker |
| 3,096,283 A | 7/1963 | Hein |
| 3,104,225 A | 9/1963 | DiBenedetto |
| 3,145,713 A | 8/1964 | Latham, Jr. |
| 3,239,136 A | 3/1966 | Hein |
| 3,244,362 A | 4/1966 | Hein |
| 3,249,295 A | 5/1966 | Childs |
| 3,304,990 A | 2/1967 | Ontko et al. |
| 3,332,614 A | 7/1967 | Webster et al. |
| 3,482,771 A | 12/1969 | Thylefors |
| 3,655,123 A | 4/1972 | Judson et al. |
| 3,675,846 A | 7/1972 | Drucker |
| 3,703,984 A | 11/1972 | Pruessner |
| 3,780,936 A | 12/1973 | Bush |
| 3,825,177 A | 7/1974 | Kohlstette et al. |
| 3,908,893 A | 9/1975 | Williams |
| 3,955,755 A | 5/1976 | Breillatt, Jr. et al. |
| 3,982,691 A | 9/1976 | Schlutz |
| 4,056,225 A | 11/1977 | Hein, Jr. |
| 4,081,129 A | 3/1978 | Stroucken |
| 4,086,924 A | 5/1978 | Latham, Jr. |
| 4,111,355 A | 9/1978 | Ishimaru |
| 4,132,349 A | 1/1979 | Khoja et al. |
| 4,226,669 A | 10/1980 | Vilardi |
| 4,285,464 A | 8/1981 | Latham, Jr. |
| 4,303,193 A | 12/1981 | Latham, Jr. |
| 4,304,357 A | 12/1981 | Schoendorfer |
| 4,332,350 A | 6/1982 | McClellan |
| 4,332,351 A | 6/1982 | Kellogg et al. |
| 4,341,343 A | 7/1982 | Beckman |
| 4,392,846 A | 7/1983 | Novoselac et al. |
| 4,421,503 A | 12/1983 | Latham, Jr. et al. |
| 4,425,112 A | 1/1984 | Ito |
| 4,530,691 A | 7/1985 | Brown |
| 4,629,564 A | 12/1986 | Pinato |
| 4,636,193 A | 1/1987 | Cullis |
| 4,684,361 A | 8/1987 | Feldman et al. |
| 4,700,117 A | 10/1987 | Giebeler et al. |
| 4,753,729 A | 6/1988 | Schoendorfer et al. |
| 4,776,964 A | 10/1988 | Schoendorfer et al. |
| 4,813,923 A | 3/1989 | Johanssson |
| 4,816,151 A | 3/1989 | Schoendorfer et al. |
| 4,828,716 A | 5/1989 | McEwen et al. |
| 4,846,781 A | 7/1989 | Knelson |
| 4,854,933 A | 8/1989 | Mul |
| 4,859,333 A | 8/1989 | Panzani |
| 4,879,031 A | 11/1989 | Panzani |
| 4,889,524 A | 12/1989 | Fell et al. |
| 4,911,833 A | 3/1990 | Schoendorfer et al. |
| 4,944,883 A | 7/1990 | Schoendorfer et al. |
| 4,959,158 A | 9/1990 | Meikrantz |
| 5,007,892 A | 4/1991 | Columbus |
| 5,032,288 A | 7/1991 | Columbus et al. |
| 5,034,135 A | 7/1991 | Fischel |
| 5,039,401 A | 8/1991 | Columbus et al. |
| 5,053,127 A | 10/1991 | Schoendorfer et al. |
| 5,076,911 A | 12/1991 | Brown et al. |
| 5,100,372 A | 3/1992 | Headley |
| 5,104,526 A | 4/1992 | Brown et al. |
| 5,147,186 A | 9/1992 | Buckholtz |
| 5,149,432 A | 9/1992 | Lavin |
| 5,188,583 A | 2/1993 | Guigan |
| 5,254,075 A | 10/1993 | Nemoto et al. |
| 5,254,076 A | 10/1993 | Chow et al. |
| 5,254,248 A | 10/1993 | Nakamura |
| 5,267,936 A | 12/1993 | Miachon |
| 5,316,667 A | 5/1994 | Brown et al. |
| 5,322,620 A | 6/1994 | Brown et al. |
| 5,354,256 A | 10/1994 | Knelson |
| 5,387,174 A | 2/1995 | Rochat |
| 5,405,308 A | 4/1995 | Headley et al. |
| 5,441,475 A | 8/1995 | Storruste et al. |
| 5,480,378 A | 1/1996 | Weis-Fogh et al. |
| 5,514,070 A | 5/1996 | Pages |
| 5,573,678 A | 11/1996 | Brown et al. |
| 5,585,007 A | 12/1996 | Antanavich et al. |
| 5,603,845 A | 2/1997 | Holm |
| 5,607,830 A | 3/1997 | Biesel et al. |
| 5,628,915 A | 5/1997 | Brown et al. |
| 5,632,893 A | 5/1997 | Brown et al. |
| 5,643,594 A | 7/1997 | Dorian et al. |
| 5,674,173 A | 10/1997 | Hlavinka et al. |
| 5,728,040 A | 3/1998 | Schill et al. |
| 5,733,446 A | 3/1998 | Holm |
| 5,738,784 A | 4/1998 | Holm et al. |
| 5,738,792 A | 4/1998 | Schoendorfer |
| 5,741,428 A | 4/1998 | Holm |
| 5,750,039 A | 5/1998 | Brown et al. |
| 5,776,336 A | 7/1998 | Holm |
| 5,788,662 A | 8/1998 | Antanavich et al. |
| 5,792,344 A | 8/1998 | Holm |
| 5,795,489 A | 8/1998 | Holm |
| 5,807,492 A | 9/1998 | Brown et al. |
| 5,824,230 A | 10/1998 | Holm et al. |
| 5,830,352 A | 11/1998 | Holm |
| 5,849,178 A | 12/1998 | Holm et al. |
| 5,851,169 A | 12/1998 | Meresz et al. |
| 5,853,600 A | 12/1998 | McNeal et al. |
| 5,858,253 A | 1/1999 | Holm |
| 5,873,810 A | 2/1999 | Holm et al. |
| 5,935,432 A | 8/1999 | Holm |
| 5,939,319 A | 8/1999 | Hlavinka et al. |
| 5,955,026 A | 9/1999 | Holm et al. |
| 5,958,253 A | 9/1999 | Holm |
| 5,961,842 A | 10/1999 | Min et al. |

(56) References Cited

U.S. PATENT DOCUMENTS

| | | |
|---|---|---|
| 5,964,724 A | 10/1999 | Rivera et al. |
| 5,980,760 A | 11/1999 | Min et al. |
| 5,993,370 A | 11/1999 | Brown et al. |
| 6,007,472 A | 12/1999 | Schill et al. |
| 6,007,725 A | 12/1999 | Brown |
| 6,027,655 A | 2/2000 | Holm |
| 6,027,657 A | 2/2000 | Min et al. |
| 6,051,146 A | 4/2000 | Green et al. |
| 6,063,297 A | 5/2000 | Antanavich et al. |
| 6,099,740 A | 8/2000 | Holm et al. |
| 6,123,655 A | 9/2000 | Fell |
| 6,123,687 A | 9/2000 | Simonyl et al. |
| 6,132,598 A | 10/2000 | Hvid et al. |
| 6,214,338 B1 | 4/2001 | Antanavich et al. |
| 6,228,017 B1 | 5/2001 | Brown |
| 6,241,649 B1 | 6/2001 | Zanella et al. |
| 6,296,602 B1 | 10/2001 | Headley |
| 6,299,784 B1 | 10/2001 | Biesel |
| 6,302,836 B1 | 10/2001 | North, Jr. |
| 6,348,031 B1 | 2/2002 | Unger et al. |
| 6,387,263 B1 | 5/2002 | Bhaskar et al. |
| 6,398,972 B1 | 6/2002 | Blasetti et al. |
| 6,416,456 B2 | 7/2002 | Zanella et al. |
| 6,475,175 B1 | 11/2002 | Rivera et al. |
| 6,511,411 B1 | 1/2003 | Brown |
| 6,530,871 B1 | 3/2003 | Mackel et al. |
| 6,544,162 B1 | 4/2003 | Van Wie et al. |
| 6,689,042 B2 | 2/2004 | Unger et al. |
| 6,716,151 B2 | 4/2004 | Panzani et al. |
| 6,716,187 B1 | 4/2004 | Jorgensen et al. |
| 6,719,901 B2 | 4/2004 | Dolecek et al. |
| 6,733,433 B1 | 5/2004 | Fell |
| 6,814,862 B2 | 11/2004 | Biesel |
| 6,835,316 B2 | 12/2004 | Dolecek |
| 6,835,353 B2 | 12/2004 | Smith et al. |
| 6,855,119 B2 | 2/2005 | Rivera et al. |
| 6,899,666 B2 | 5/2005 | Brown |
| 6,905,612 B2 | 6/2005 | Dorian et al. |
| RE38,757 E | 7/2005 | Wells et al. |
| 6,946,079 B1 | 9/2005 | Holm |
| 6,962,560 B2 | 11/2005 | Grewel |
| 6,964,646 B1 | 11/2005 | Biesel |
| 6,979,307 B2 | 12/2005 | Beretta et al. |
| 6,982,038 B2 | 1/2006 | Dolecek et al. |
| 7,001,323 B2 | 2/2006 | Panzani et al. |
| 7,029,430 B2 | 4/2006 | Hlavinka et al. |
| 7,033,501 B1 | 4/2006 | Bhaskar et al. |
| 7,037,428 B1 | 5/2006 | Robinson et al. |
| 7,060,017 B2 | 6/2006 | Collier |
| 7,060,018 B2 | 6/2006 | Skinkle et al. |
| 7,074,173 B2 | 7/2006 | Kohlstette et al. |
| 7,081,082 B2 | 7/2006 | Scholz et al. |
| 7,134,991 B2 | 11/2006 | Rivalier et al. |
| 7,156,800 B2 | 1/2007 | Panzani et al. |
| 7,179,391 B2 | 2/2007 | Leach et al. |
| 7,195,606 B2 | 3/2007 | Ballin |
| 7,204,795 B2 | 4/2007 | Himmen et al. |
| 7,223,346 B2 | 5/2007 | Dorian et al. |
| 7,252,758 B2 | 8/2007 | Dolecek et al. |
| 7,306,555 B2 | 12/2007 | Dolecek et al. |
| 7,311,849 B2 | 12/2007 | Panzani et al. |
| 7,314,441 B2 | 1/2008 | Collier |
| 7,347,932 B2 | 3/2008 | Holmes et al. |
| 7,347,948 B2 | 3/2008 | Dolecek et al. |
| 7,354,515 B2 | 4/2008 | Coull et al. |
| 7,364,657 B2 | 4/2008 | Mandrusov et al. |
| 7,374,678 B2 | 5/2008 | Leach et al. |
| 7,407,472 B2 | 8/2008 | Skinkle et al. |
| 7,413,652 B2 | 8/2008 | Dolecek et al. |
| 7,470,371 B2 | 12/2008 | Dorian et al. |
| 7,520,402 B2 | 4/2009 | Ellsworth et al. |
| 7,553,413 B2 | 6/2009 | Dorian et al. |
| 7,694,828 B2 | 4/2010 | Swift et al. |
| 7,708,152 B2 | 5/2010 | Dorian et al. |
| 7,740,760 B2 | 6/2010 | Coull et al. |
| 7,745,106 B2 | 6/2010 | Beretta et al. |
| 7,771,590 B2 | 8/2010 | Leach et al. |
| 7,780,860 B2 | 8/2010 | Higgins et al. |
| 7,789,245 B2 | 9/2010 | Westberg et al. |
| 7,803,279 B2 | 9/2010 | Coull et al. |
| 7,806,276 B2 | 10/2010 | Leach et al. |
| 7,811,463 B2 | 10/2010 | Dolecek et al. |
| 7,824,559 B2 | 11/2010 | Dorian et al. |
| 7,828,709 B2 | 11/2010 | Sweat |
| 7,832,566 B2 | 11/2010 | Leach et al. |
| 7,833,185 B2 | 11/2010 | Felt et al. |
| 7,837,884 B2 | 11/2010 | Dorian et al. |
| 7,845,499 B2 | 12/2010 | Higgins et al. |
| 7,857,744 B2 | 12/2010 | Langley et al. |
| 7,866,485 B2 | 1/2011 | Dorian et al. |
| 7,867,159 B2 | 1/2011 | Dolecek et al. |
| 2005/0054506 A1 | 3/2005 | Bradley |
| 2006/0104863 A1 | 5/2006 | Bell |
| 2006/0191857 A1 | 8/2006 | Hlavinka et al. |
| 2008/0128367 A1 | 6/2008 | Rochat |

FOREIGN PATENT DOCUMENTS

| | | |
|---|---|---|
| WO | 9400169 | 1/1994 |
| WO | 2010127278 A1 | 11/2010 |
| WO | 2012067658 A2 | 5/2012 |

OTHER PUBLICATIONS

International Search Report dated Jul. 30, 2013 re Application No. PCT/US2013/026175.

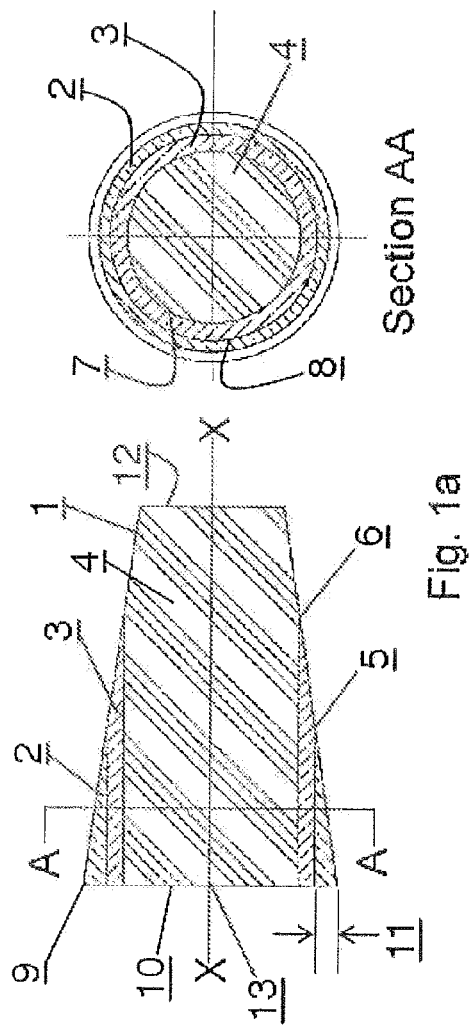
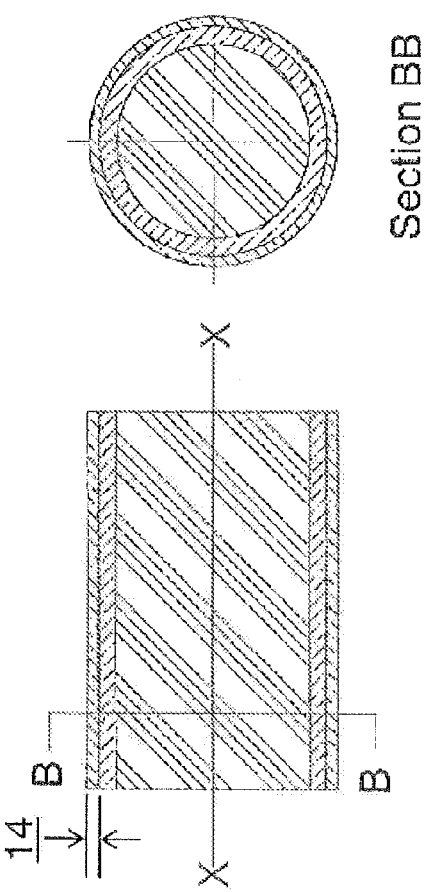
Fig. 1a
Fig. 1b

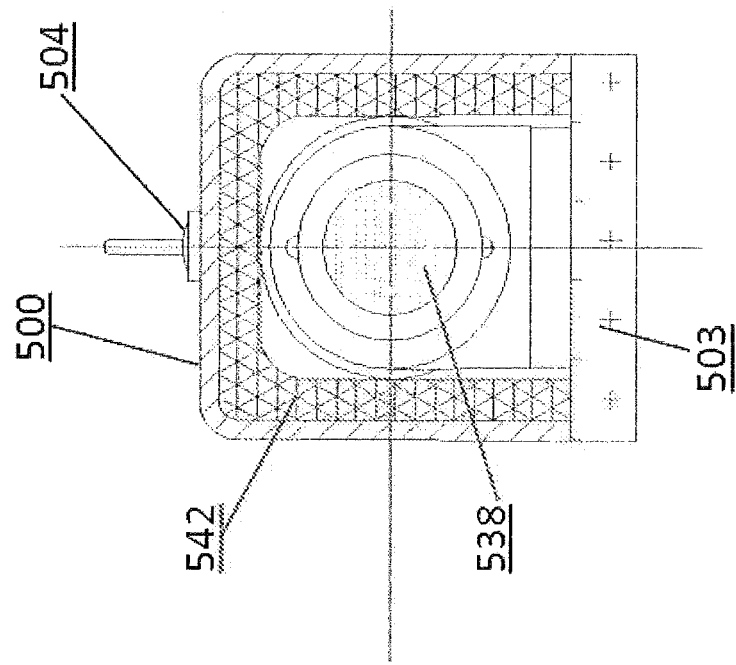
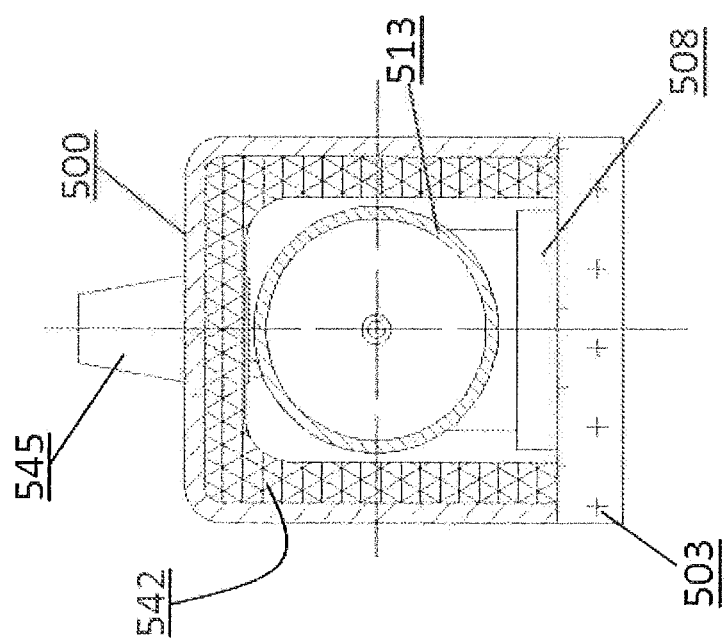
Fig. 18 A
Fig. 18 B

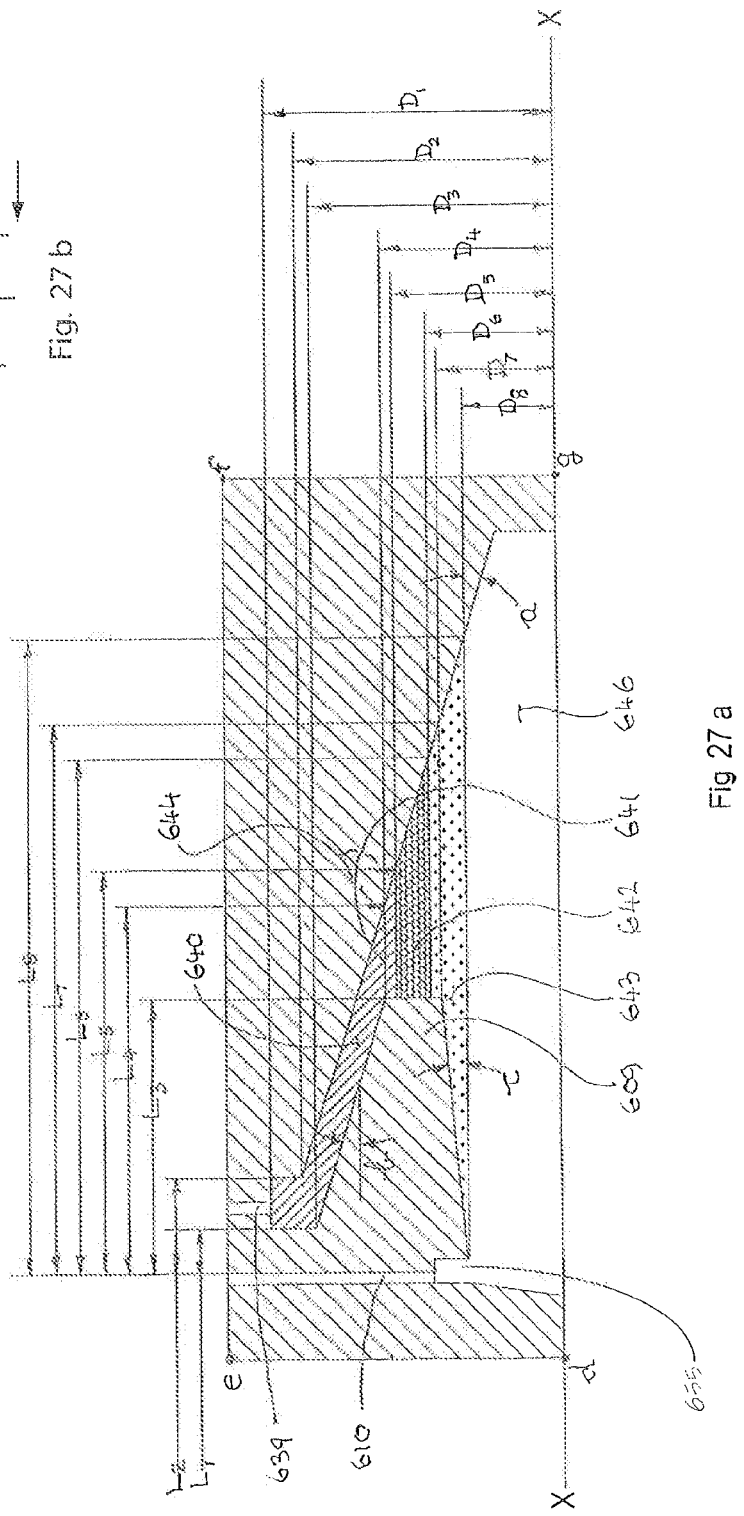
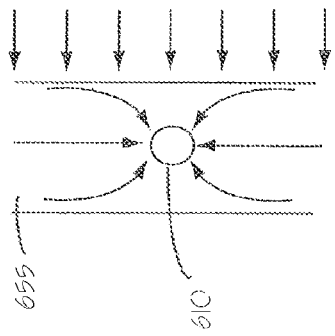
Fig. 27 b
Fig 27 a

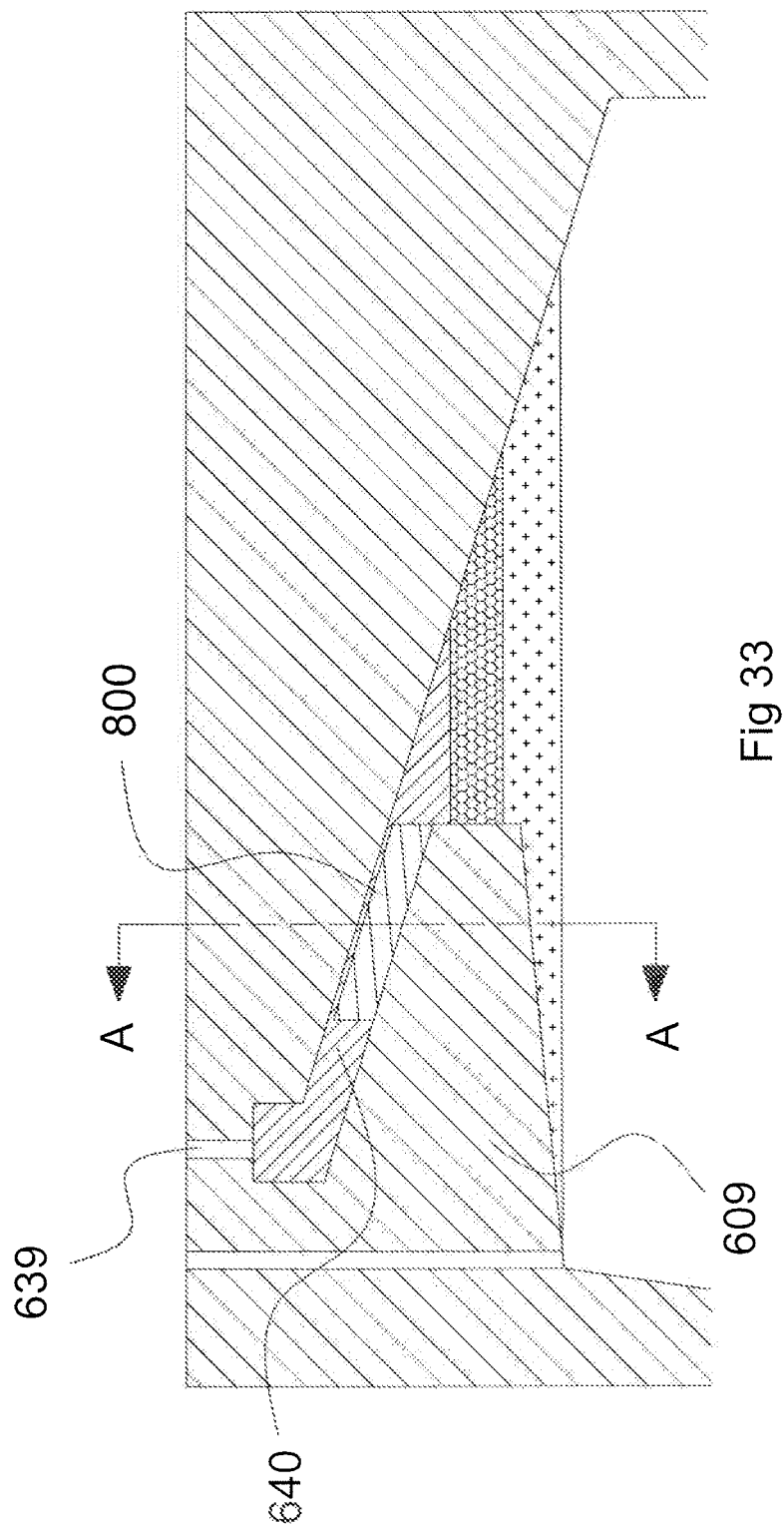

CENTRIFUGE

CROSS REFERENCE TO RELATED APPLICATIONS

This application is a Continuation of U.S. patent application Ser. No. 13/766,528, filed on Feb. 13, 2013, entitled Centrifuge, which is a Continuation-In-Part of U.S. patent application Ser. No. 13/447,008, filed on Apr. 13, 2012, entitled Centrifuge, which is a Continuation-In-Part of U.S. patent application Ser. No. 13/396,600, filed on Feb. 15, 2012, which is a Continuation-In-Part Application of our earlier filed PCT International Patent Application S.N. PCT/US11/01922, filed on Nov. 19, 2011, and designating the U.S., which is a Continuation-In-Part of U.S. patent application Ser. No. 13/209,226, filed on Aug. 12, 2011. The Ser. No. 13/396,600 application is also a Continuation-In-Part of our earlier filed U.S. patent application Ser. No. 13/209,226, which is a Continuation-In-Part of U.S. patent application Ser. No. 12/949,781, filed on Nov. 19, 2010. All of the above listed applications are assigned to the same assignee as this invention and whose disclosures are incorporated by reference herein.

TECHNICAL FIELD

The present invention pertains to centrifuges.

BACKGROUND ART

Fluids, such as whole blood or various other biological fluids are suspensions and can be separated into their constituent parts or fractions. For example, whole blood comprises four main fractions, red blood cells, white blood cells, platelets and plasma, that can be separated based on their different specific gravities in a device such as a centrifuge. An anti-coagulated whole blood sample may be placed in a test tube, or other similar device, which is then spun in a centrifuge at a specified speed. The generated centrifugal force separates the blood into the different fractions based on their relative specific gravities. The red blood cells are on the bottom, plasma, is on the top with the intermediate specific gravity white blood cells and platelets (together referred to as the buffy coat (BC)) intermediate to the other two fractions. Various other biological fluids may be separated as well. For example, nucleated cells may be separated and extracted from bone marrow or adipose tissue derived samples.

It is desirable to isolate the different fractions of whole blood for differing medicinal purposes. The platelets can be obtained in preparations of platelet rich plasma (PRP) or platelet concentrates (PC). Platelets contain growth factors (e.g. PDGF, TGF-β, and others), which may initiate, aid in or accelerate various bodily functions, including but not limited to angiogenesis, wound healing, and osteogenesis. Administering autologous platelets to an injury site may improve the healing response by using a patient's own platelets without the risk of infection by using blood products from another donor source. Alternatively, platelet poor plasma (PPP) may be desired for use in various procedures. PPP may be prepared by isolating the plasma fraction from platelet concentrates, and preserving the isolated plasma fraction.

Various systems exist for the production of PRP/PC. Some use specialized test tubes, U.S. Pat. Nos. 7,179,391 and 7,520,402, that can include floats, tubing and/or gel materials of specific densities. Other systems use specialized double syringes, for example those found in U.S. Pat. Nos. 6,716,187 and 7,195,606. These test tubes and syringes must be centrifuged in a specialized large centrifuge for a specified time, typically 10-30 minutes, and then by delicate handling and extraction or decanting procedures produce the desired PRP/PC. The consistency of these preparations can vary depending on the operator's skill level. Other systems, for example U.S. Pat. No. 6,982,038, contain specialized centrifuge chambers and complicated control systems to produce the PRP/PC in about 30 minutes. All of these systems provide PRP/PC of differing platelet concentrations depending on the method used. A major drawback to these methods is the need for an expensive piece of capital equipment which limits the utility to facilities that have the funds and space available. These methods also require considerable operator skills to complete the procedures necessary to obtain the PRP/PC.

The ability to produce PRP/PC from a patient's own blood at the point of care without the need for complex, expensive equipment and difficult procedures would facilitate the clinical utility of PRP/PC. Therefore the objects of this invention include among other things providing an apparatus and method for processing a patient's own blood at the point of care in a short period of time that is self contained, battery operated, small and or portable, inexpensive, easy to use, reproducible, able to separate many cellular populations, and disposable without the need for additional centrifugation equipment

DISCLOSURE OF THE INVENTION

In accordance with the invention, a single use, sterile, self-contained, compact, easy to use centrifugal separation unit provides for quick, reliable concentration of constituents of a liquid mixture, for example, a biologic liquid mixture, such as platelet concentration from whole blood, or alternatively concentrating cells from bone marrow aspirate. The resultant PRP/PC can be immediately used for application to the patient. The unit is suitable for office, operating room, emergency use, or military field hospital use.

The disposable self-contained PRP separator features a motor with a drive axis, the drive axis being coaxial with the central or longitudinal axis of the blood separation chamber (BSC) assembly. The motor can have the capacity to rotate the BSC at speeds in the range 10,000 to 25,000 RPM for several minutes. Power can be supplied to the motor through a battery or other power pack. The power can be connected through a switch and even small dry cell batteries will have sufficient capacity to complete the separation process. The BSC and motor/battery are fully enclosed in an outer container that includes an access port to the BSC to which a standard syringe can be attached. Alternatively the BSC can be rotated by non-electrical means such as an air driven turbine or spring drive. It could also include a magnetic or mechanical coupling to an external drive motor, or any source of energy that may be available at the surgical site for example in the surgical suite or on location during a trauma procedure, such as at a "MASH" compound.

In a first embodiment the BSC assembly features a barrel that may be cylindrical or tapered, an end cap incorporating passageways and a tubular extension, and in some embodiments a piston or bladder, that between them define the BSC. A sleeve sliding over the outer diameter of the end cap acts as the moving part of two valve assemblies, each valve featuring a recess in the outer surface of the end cap and an O-ring in the recess. Passages within the end cap lead from the BSC to the recess centers, and two ports in the sleeve align with the recess centers in a 3 position sequence. The two ports in the sleeve are positioned so that they do not align with the two recess centers in the end cap at the same time. In sequence, the sleeve selects a first port open, then both ports closed, and then a second port open. The ports are opened in a stepwise motion, but could be opened proportionally. The sleeve is operated by a knob connected to a slidable collar through a bearing assembly so that the knob does not rotate during operation of the motor.

Anti-coagulated blood is injected through the tubular extension in order to fill the BSC. The sleeve is in a first position where both ports on the sleeve do not align with either of the recesses in the end cap. The motor is actuated and the BSC rotates to create a centrifugal force on the blood thereby separating it into its components with the red blood cells closest to the inner wall of the BSC with the white blood cells lining the red blood cell layer toward the center, followed by the platelets and then plasma filling the center. In other words, the centrifugation yields concentric stratified constituent layers of the mixture, with adjacent concentric stratified constituent layers defining a mixture interface. After a centrifugation period of about 1 minute or less the sleeve is moved to a second position in which the first port in the sleeve aligns with the recess in the end cap. This port communicates with the layer of red blood cells against the inner wall. The red blood cells will exit the chamber through this port due to pressure generated by the centrifugal force. As red blood cells exit the separator, the volume is replaced by air entering through the tubular extension in the end cap. The air forms a column in the center of the chamber that grows larger as more volume is replaced. It is also conceived that without an air inlet vent, that continued rotation and evacuation of the red blood cells will result in a vacuum core being formed, as the blood is degassed and possibly drawing vapor from the liquid due to the reduced pressure at the center of rotation. After a substantial amount, preferably the majority, of the red blood cells are discharged from the blood separator volume, the sleeve is moved to a third position to close the first port and open the second port. This is done before the layer of platelets in the volume can exit the first port. The passage to the second recess in the end cap of the device is precisely positioned away from the center axis to remove a volume of plasma from the BSC without disturbing the platelet layer. As plasma leaves the chamber, air replaces the volume through the tubular extension and the column of air in the center of the BSC continues to grow in diameter. When the diameter of the air column encompasses the second passage entrance, no more plasma can exit the chamber and the concentration process is thereby automatically ended. In the case where there is a vacuum core created, the concentration process would automatically end in a similar manner, as the vacuum core encounters the second passage entrance. The device is turned off and the platelet concentrate is ready for use.

Another embodiment uses a flexible bladder lining the interior of the BSC. The solid end of the BSC includes a hole for air to enter around the exterior of the flexible bladder. The end cap axis tubular extension includes an airtight valve. This embodiment operates in the same manner except that it does not deliberately introduce air into contact with the blood sample. During the centrifugation cycle while red blood cells and then plasma are exiting the chamber, air enters the opposite side of the chamber thus collapsing the flexible bladder. Due to the pressure generated in the liquid by centrifugal force, the sack collapses into a "W" shape with the open ends of the "W" facing toward the end of the chamber opposite the end with the air bleed hole. As more plasma exits the chamber the middle of the "W" reaches the second passage in the end cap and closes the passage off thus automatically ending the cycle.

Another embodiment replaces the flexible bladder with a piston and spring: as red blood cells (RBCs) exit the valve ports, the piston moves towards the end cap encouraged by the spring.

It is further disclosed that the system of the subject invention may incorporate an automatic shutoff mechanism to seal the port(s) based upon certain conditions. For example, one such mechanism can incorporate a flowable separation aid in the form of a gel of an intermediate specific gravity selected to be between an undesired element, e.g. red blood cells, and a desired therapeutic element, e.g. platelets. The separator gel viscosity is designed so that it will not pass through the small exit port at the centrifuge speed employed in the blood separation centrifuge. Upon activation of the centrifuge, the separator gel would create a distinct layer and barrier between the outer red blood cell layer, located near the periphery of the axis of rotation, and the platelet poor layer which would be located closer to the center axis of the centrifuge rotation. The separator gel automatically plugs the first port when all of the red blood cells have exited. As a further example, the automatic shut-off of the first port can be accomplished with a solid damper, or vent flap, also constructed of a material with a specifically targeted intermediate specific gravity. Upon initial operation, the damper would open and separate away from the vent hole based upon its density and attempt to position itself at a location between the red blood cells and the platelets. As in the previous example, once the red blood cells have fully exited the system, the damper would seal the vent hole and effectively prevent the platelet rich fluid from exited the system. As yet another example of a separation aid, plastic beads such as microspheres with the desired intermediate specific gravity could also be pre-located within the centrifuge chamber. The beads would be sized appropriately to plug the exit port after the undesirable element, e.g. red blood cells, exited the system.

In another embodiment, the BSC, or at least a portion thereof, can be made of a clear (transparent) material so that the progress of the red blood cell removal can be observed through a clear window in the outer case. This can allow for precise timing for closing the first port to end the exiting of the red blood cells.

Another embodiment accomplishes the concentration through precise timing of the valve opening/closing sequence and the starting and stopping of the motor.

In another embodiment, the system may feature a reusable drive component with a motor that is arranged to be coupled to a disposable centrifuge component, wherein the blood products are centrifuged, separated, and contained entirely within the disposable unit, such that the drive component is not exposed to blood product and may be reused without fear of contamination.

In another embodiment, the disposable unit may include blood absorbent materials or fluid receiving chambers to capture the evacuated blood products.

In another embodiment, the rotation chamber is arranged to minimize the disruption to the interfaces between the separated blood products, while the red blood cells and plasma components are evacuated from the rotating chamber.

BRIEF DESCRIPTIONS OF THE DRAWINGS

FIGS. 1a and 1b: Principle of operation.

FIG. 2: Centrifuge with spring loaded piston in tapered chamber, charge position, RBC valve open, Plasma valve closed (Longitudinal part section).

FIGS. 3a, 3b, 3c, and 3d show transverse sections of the centrifuge with spring loaded piston in tapered chamber, (transverse sections of FIG. 2), and enlarged details of the RBC valve components used in all devices shown in FIGS. 2, 4, 5, 6, 7, 9, 10, 11, 12, 14, 15, 16, 17, and 18.

Figure 4:
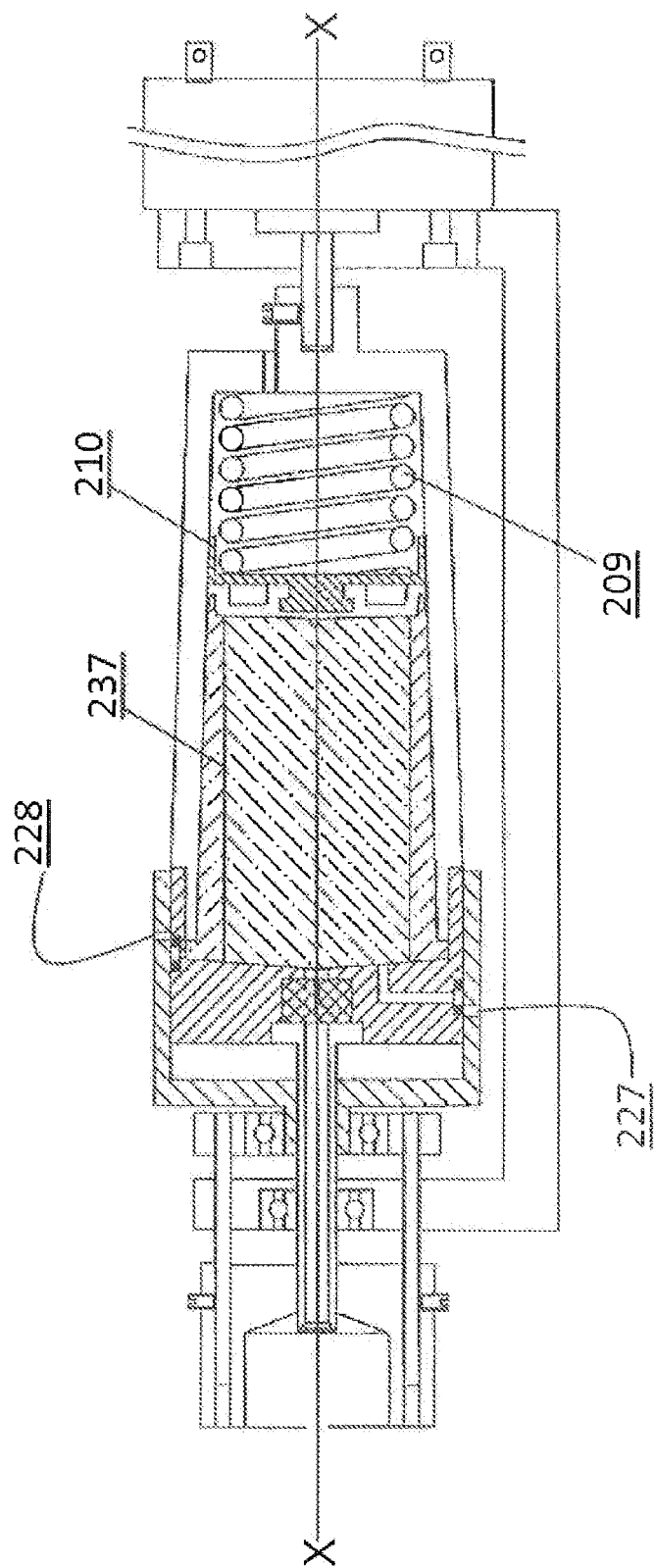

FIG. 4: Centrifuge with spring-loaded piston in tapered chamber, spin-down, RBCs separated from plasma, both valves closed (Longitudinal part section).

Figure 5:
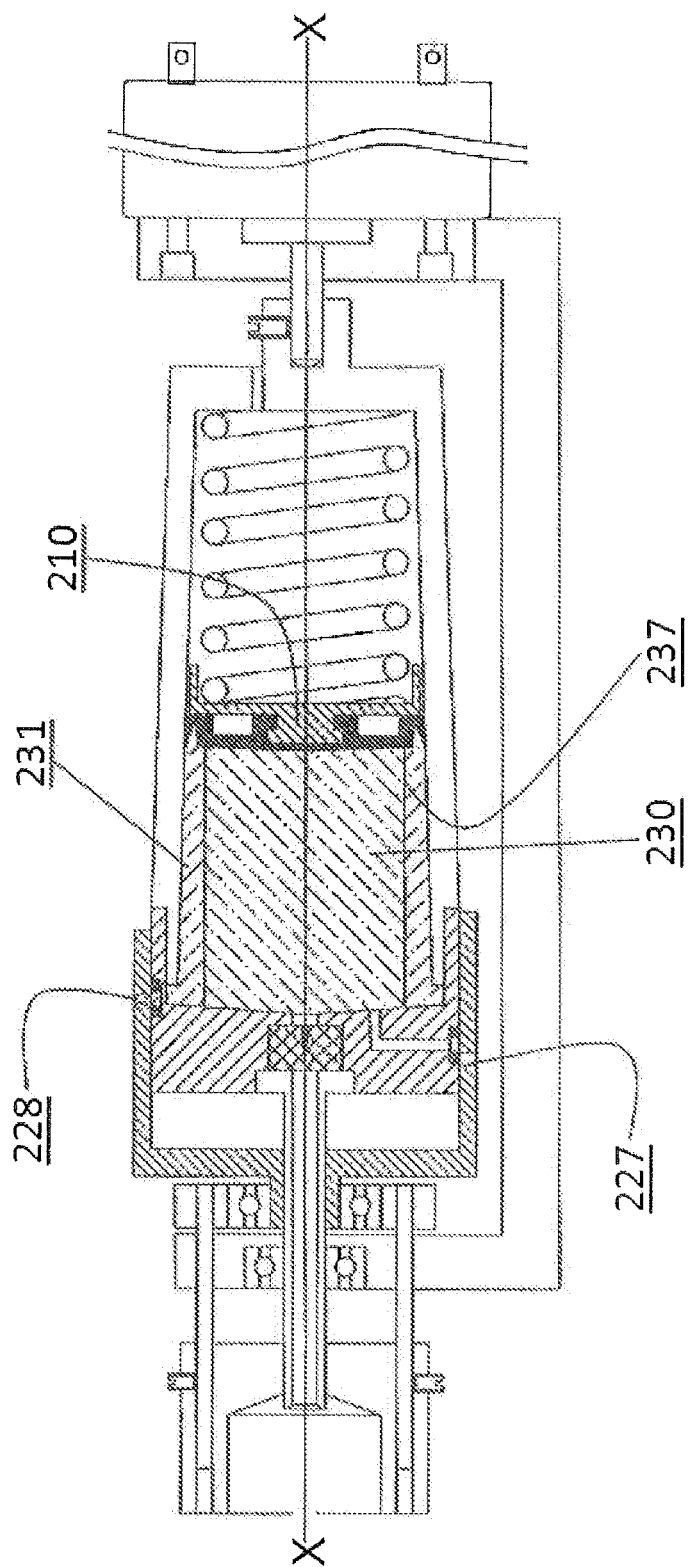

FIG. 5: Centrifuge with spring-loaded piston in tapered chamber, mid position, RBC valve open and RBCs being dumped, plasma valve closed (Longitudinal part section).

Figure 6:
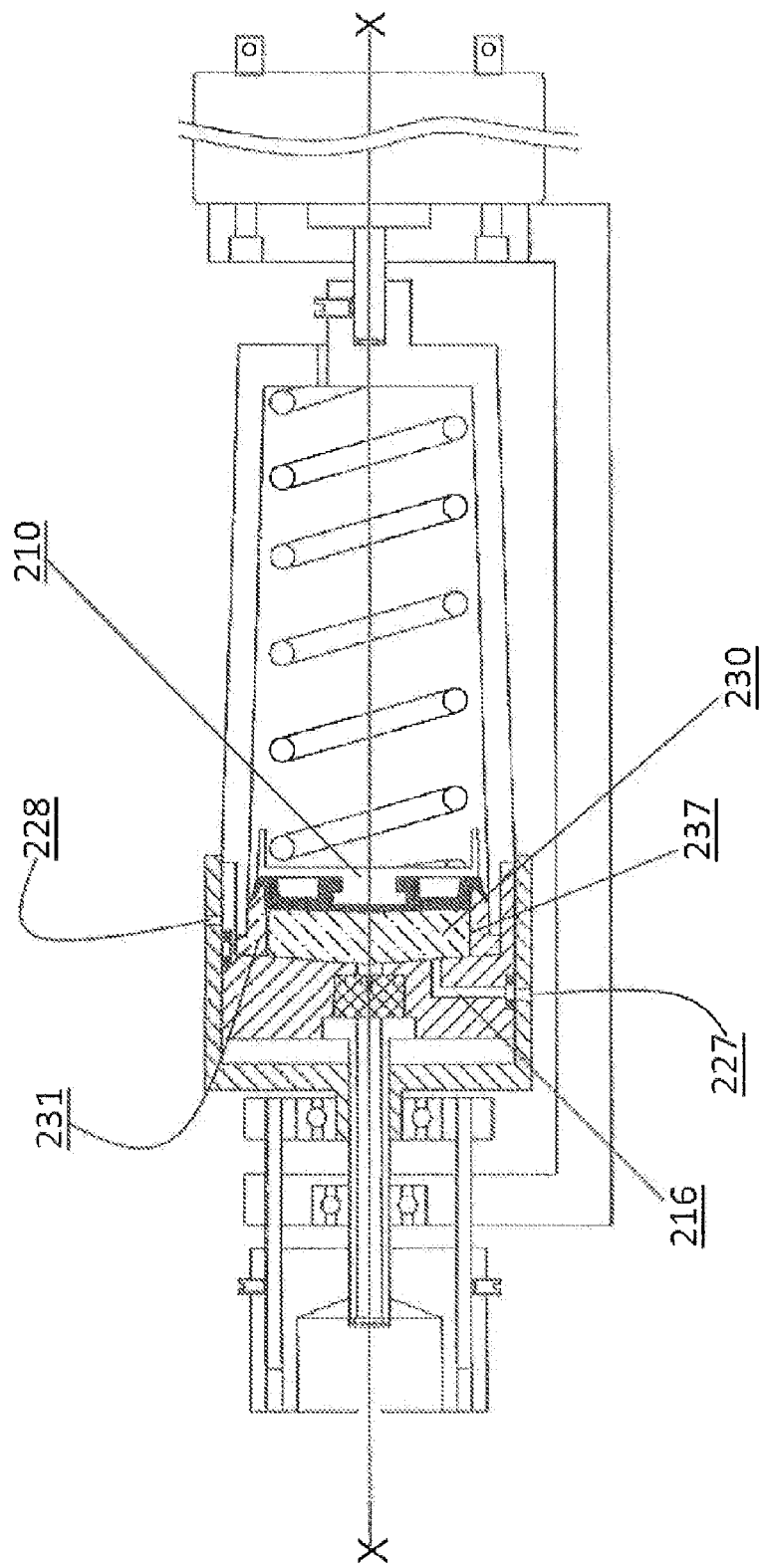

FIG. 6: Centrifuge with spring-loaded piston in tapered chamber, final position, RBC valve closed, plasma valve open and most of plasma dumped (Longitudinal part section).

Figure 7:
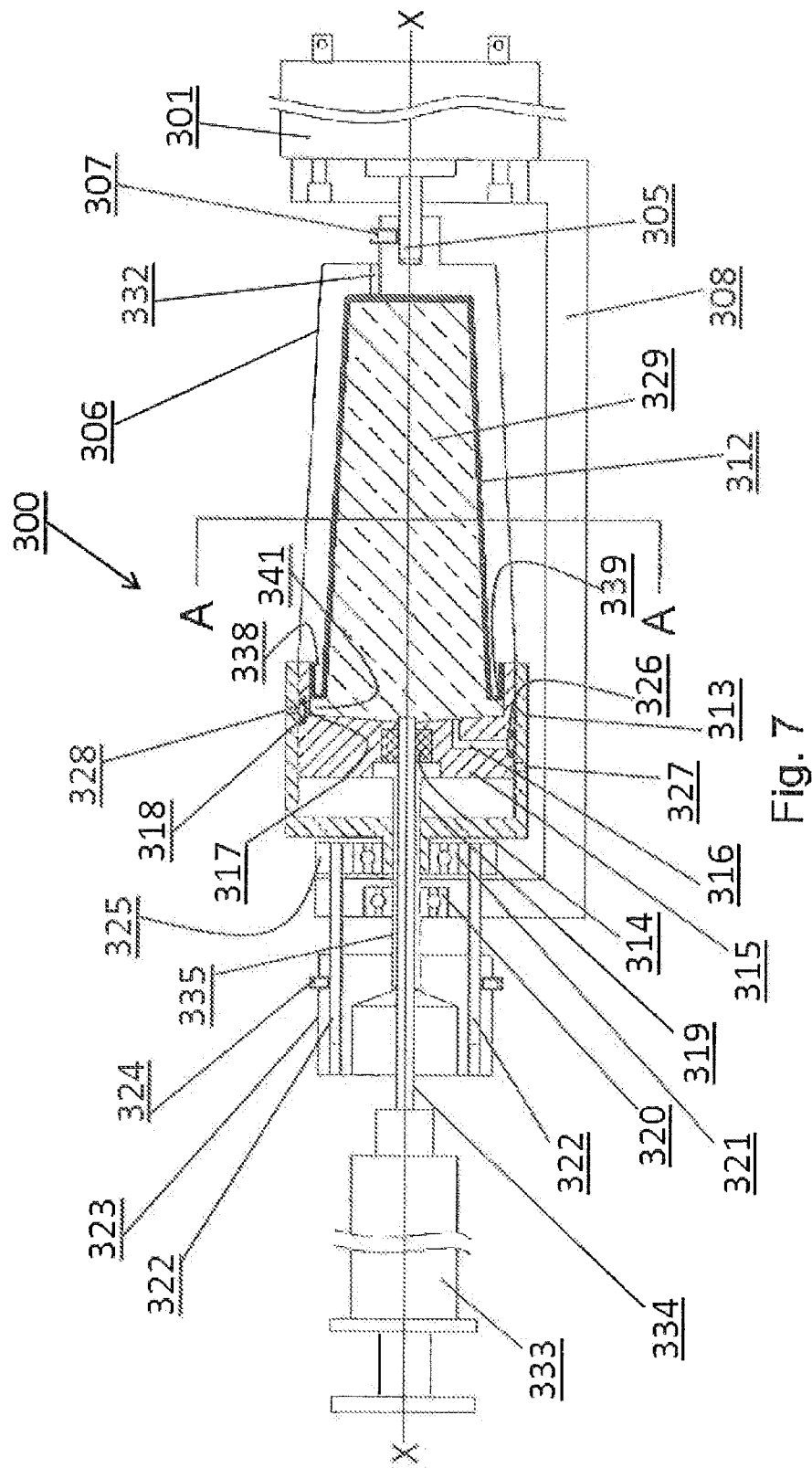

FIG. 7: Centrifuge with bladder chamber, charge position, RBC valve open, plasma valve closed (Longitudinal part section).

Figure 8:
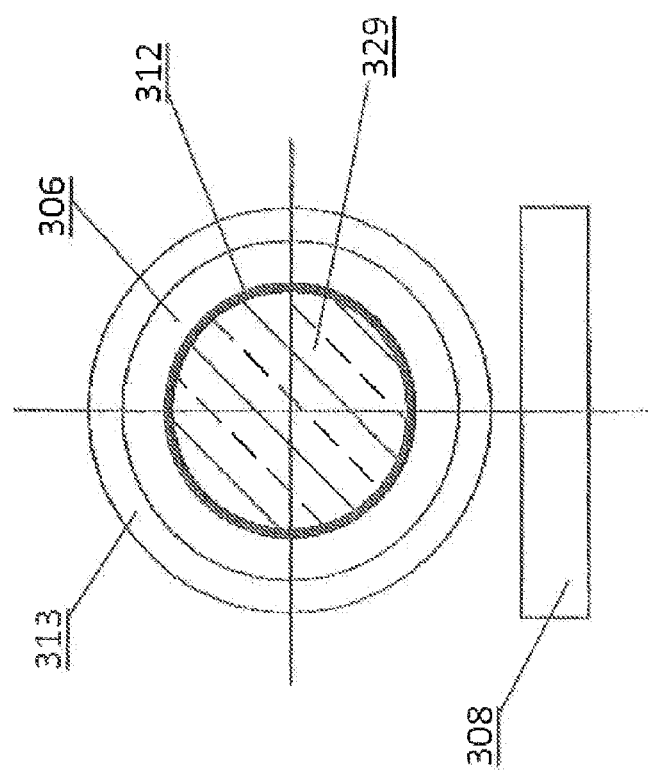

FIG. 8: Centrifuge with bladder chamber, charge position, (transverse section of FIG. 7).

Figure 9:
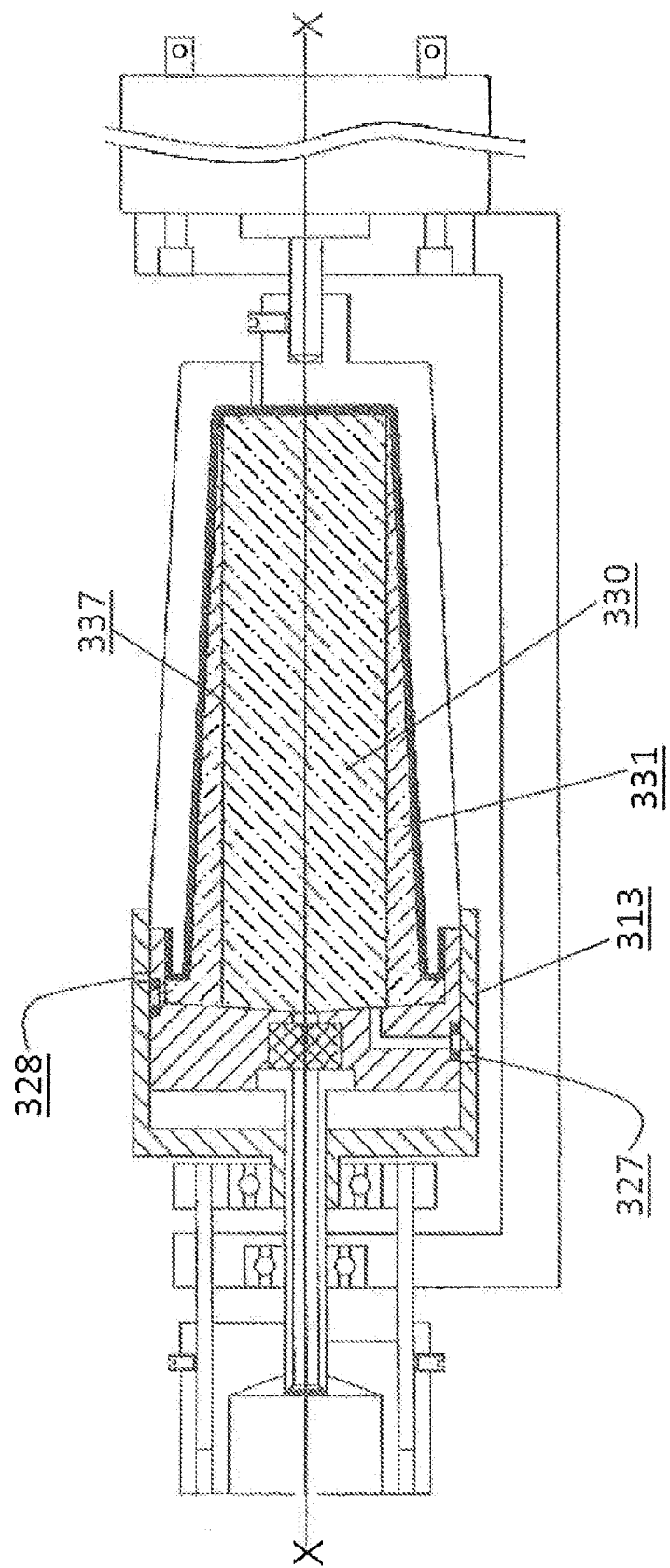

FIG. 9: Centrifuge with bladder chamber, spin-down, RBCs separated from plasma, both valves closed, (longitudinal part section).

Figure 10:
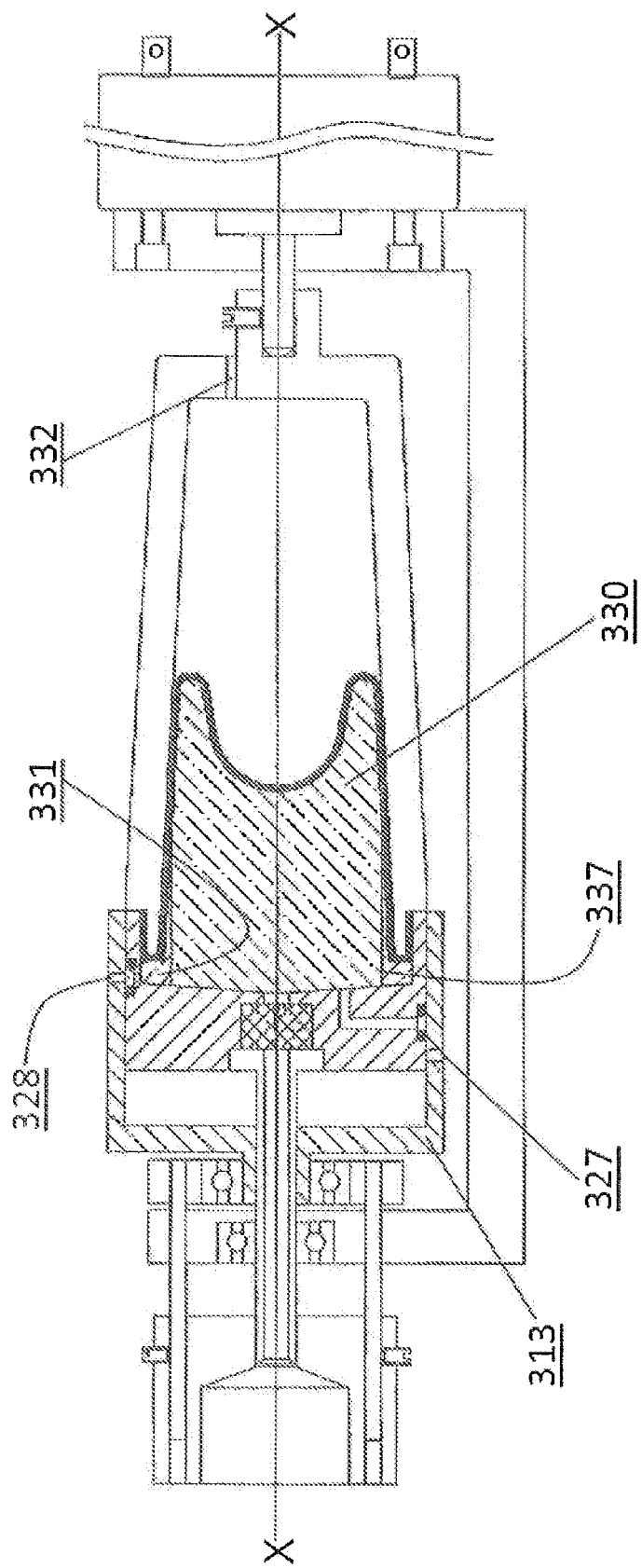

FIG. 10: Centrifuge with bladder chamber, RBCs dumping position, RBC valve open, plasma valve closed (Longitudinal part section).

Figure 11:
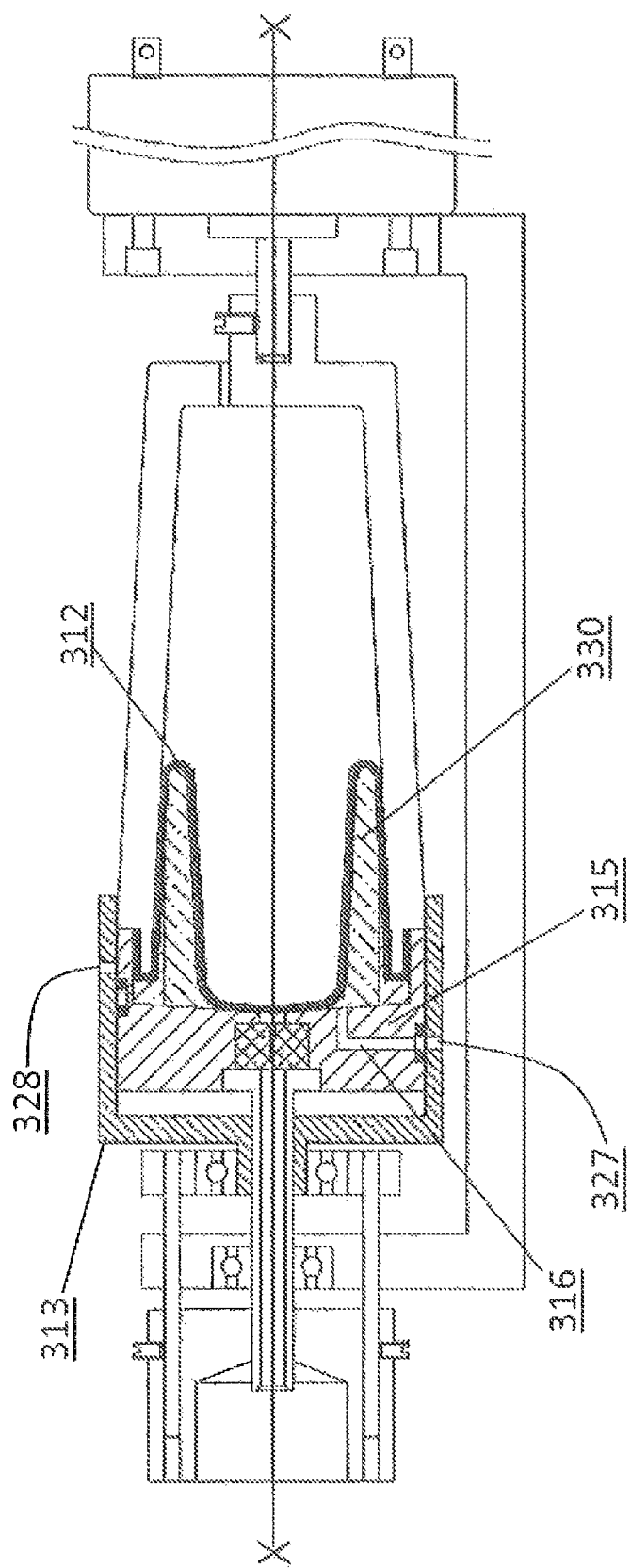

FIG. 11: Centrifuge with bladder chamber, Plasma valve open, RBC valve closed, plasma being dumped (Longitudinal part section).

Figure 12:
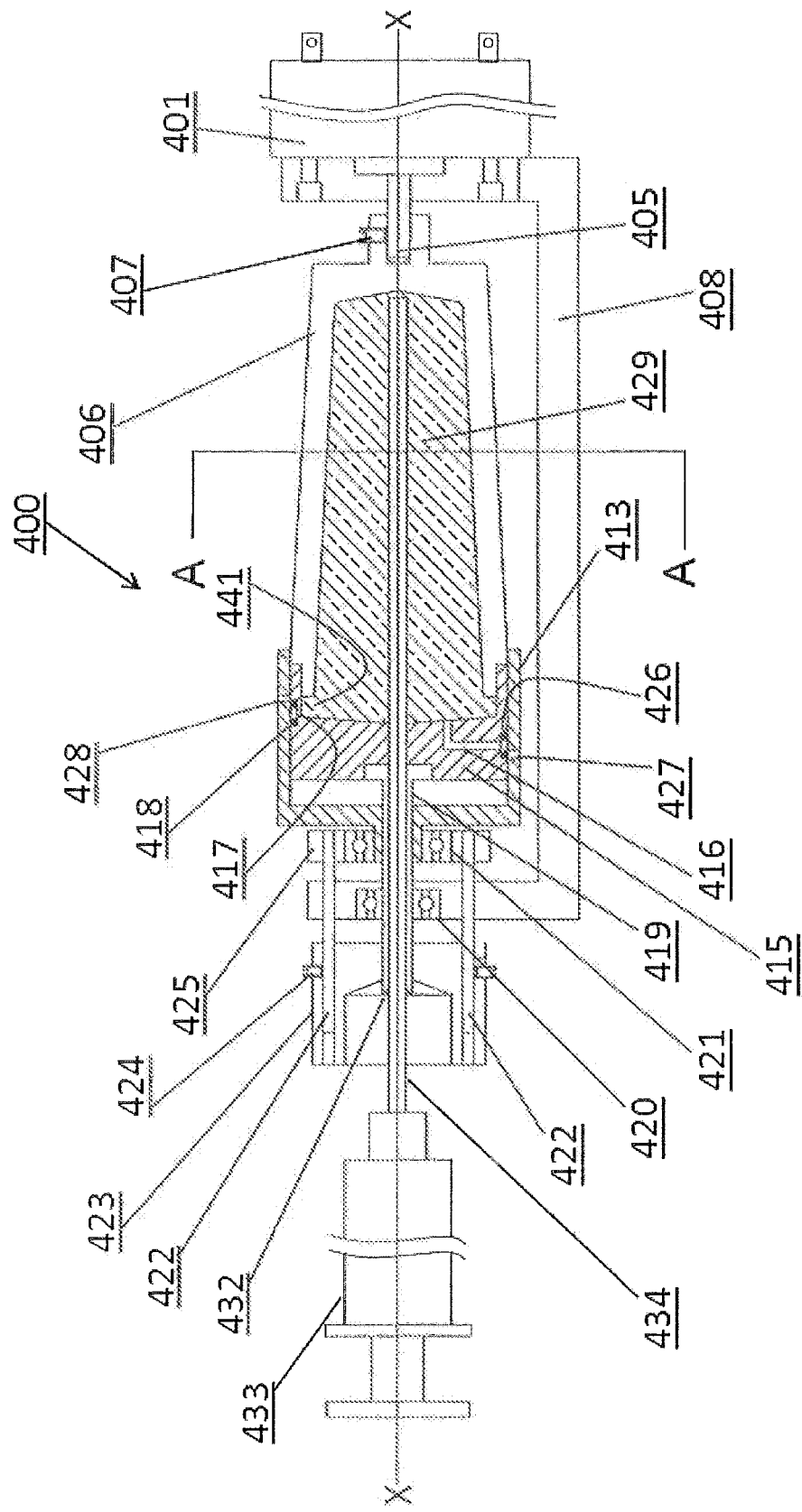

FIG. 12: Centrifuge with air core, initial charge position, both valves closed. (Longitudinal part section).

Figure 13:
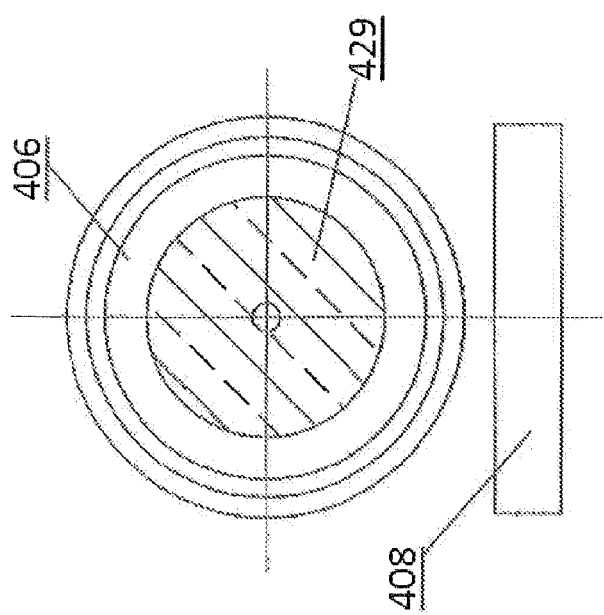

FIG. 13: Centrifuge with air core, (transverse section of FIG. 12).

Figure 14:
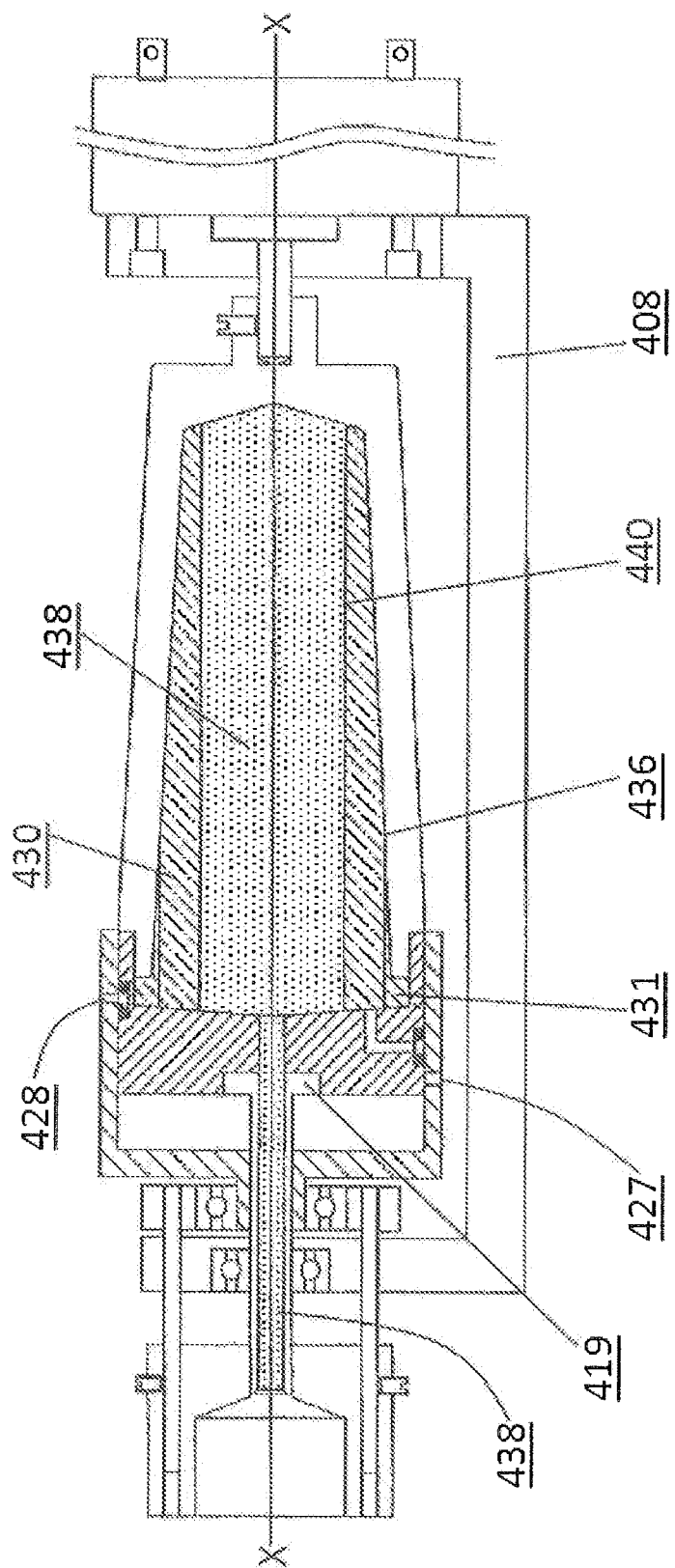

FIG. 14: Centrifuge with air core, spin and separate, RBCs being dumped, RBC valve open, plasma valve closed (Longitudinal part section).

Figure 15:
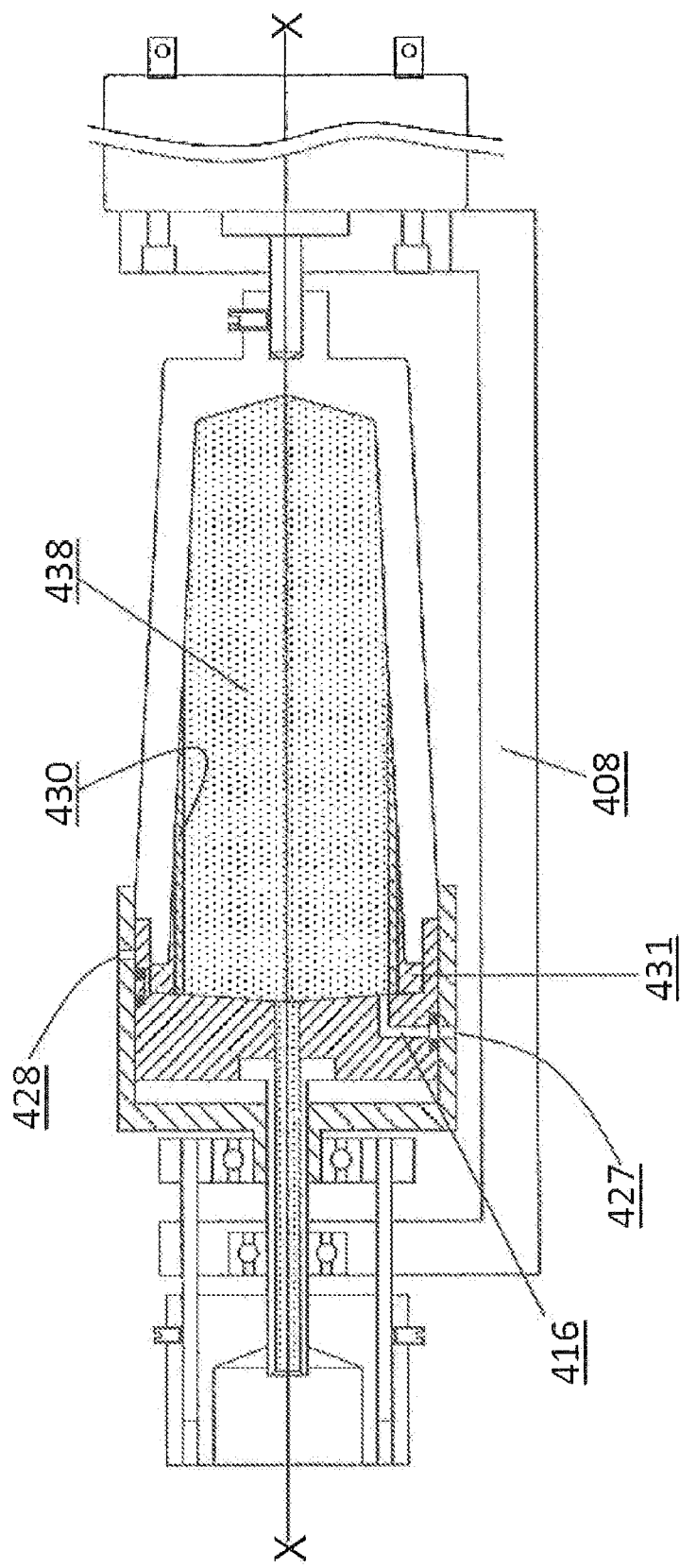

FIG. 15: Centrifuge with air core, RBC valve closed, plasma valve open, residual RBCs and residual plasma remaining (Longitudinal part section).

Figure 16:
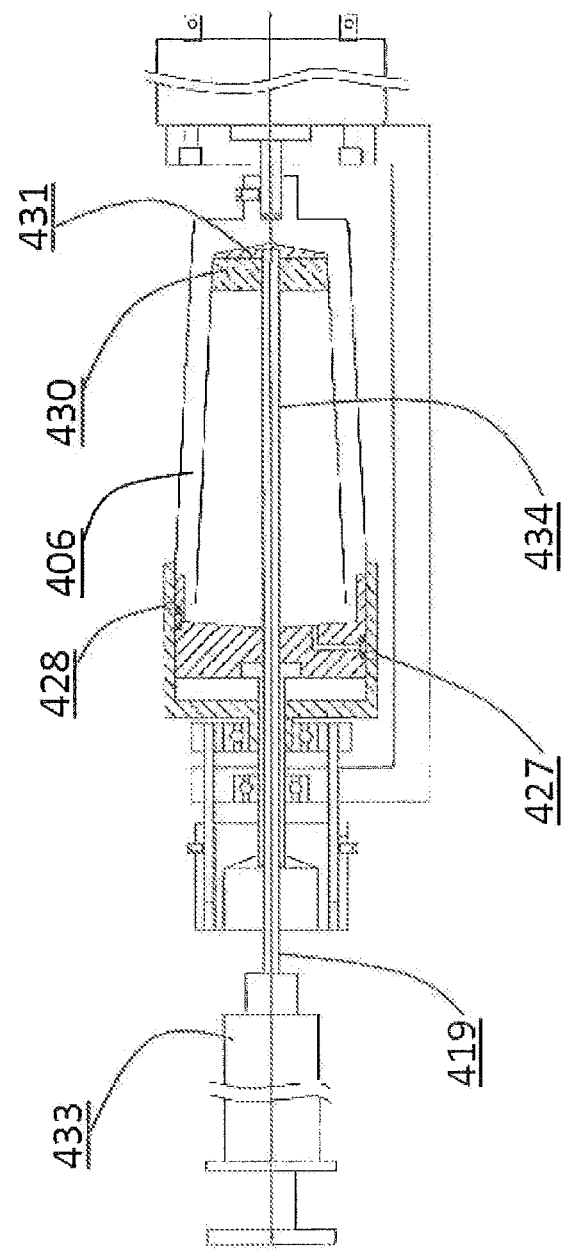

FIG. 16: Centrifuge with air core, removal of PRP at finish, both valves closed (Longitudinal part section).

Figure 17:
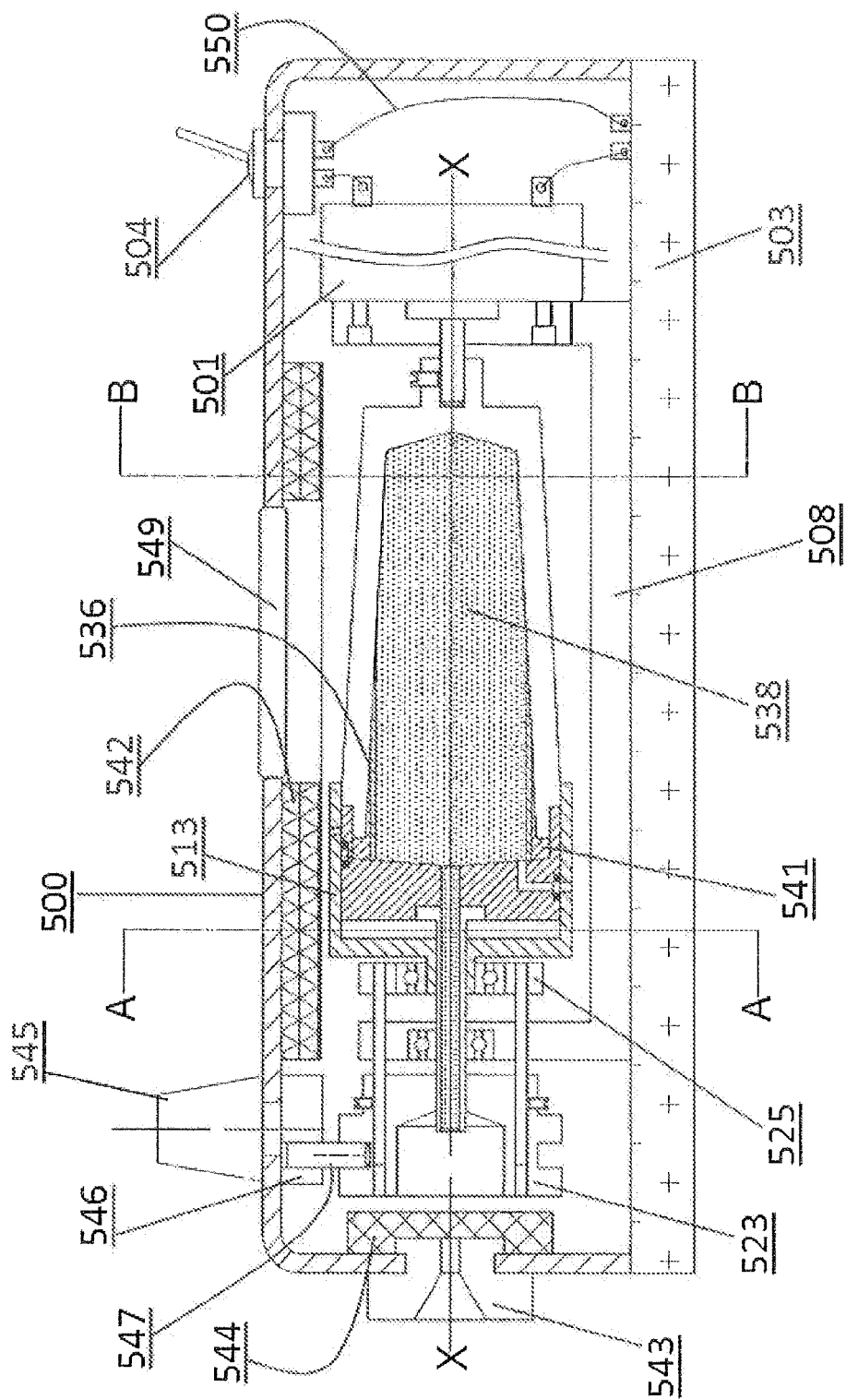

FIG. 17: Centrifuge with a typical enclosure (Longitudinal part section, showing RBC and plasma capture means and aerosol prevention means).

FIGS. 18a and 18b: Centrifuge with typical enclosure, (transverse section of FIG. 17).

Figure 19:
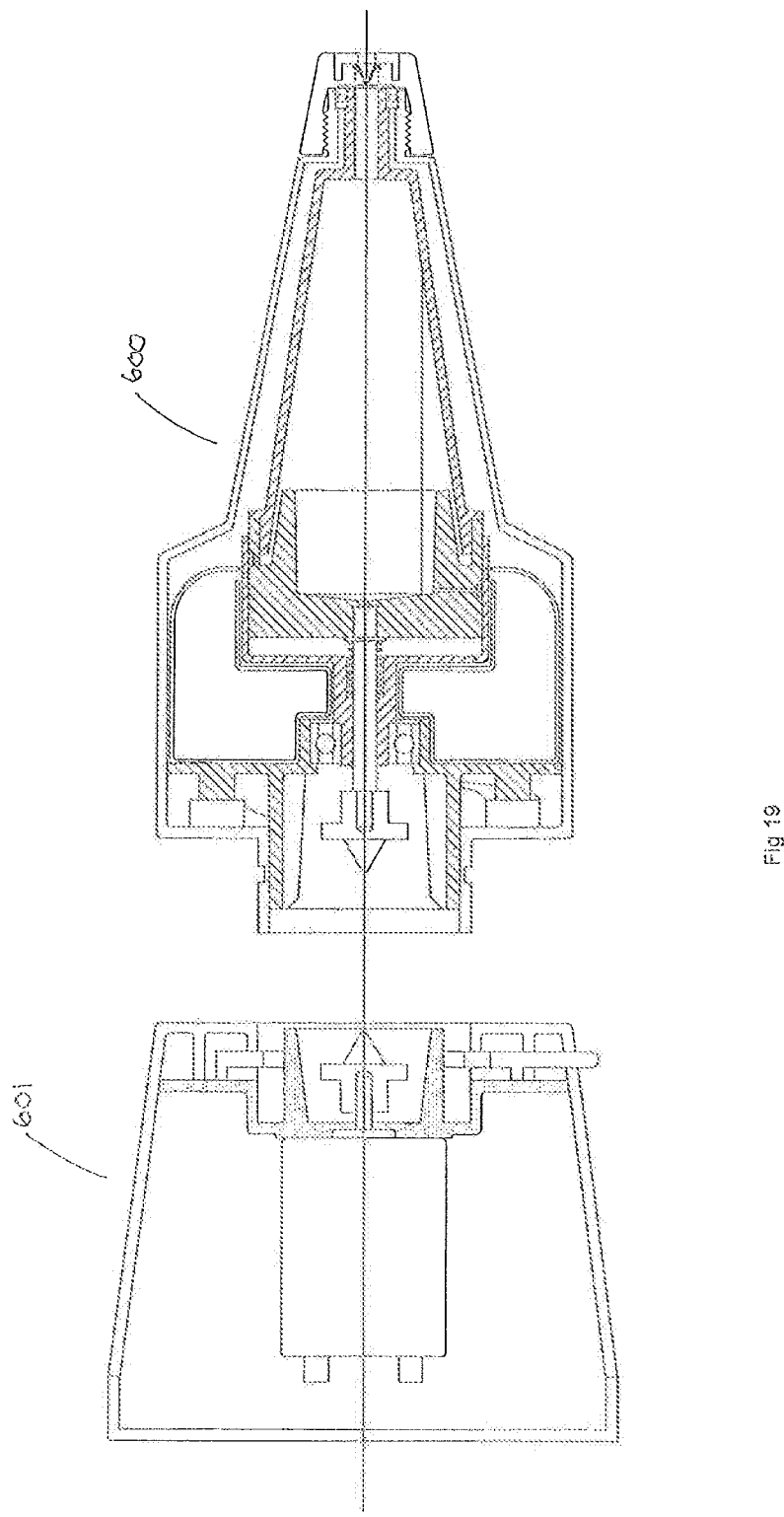

FIG. 19. Simplified longitudinal cross section of centrifuge with disposable and reusable components shown separated. Shown with the red blood cell and plasma valves closed.

Figure 20:
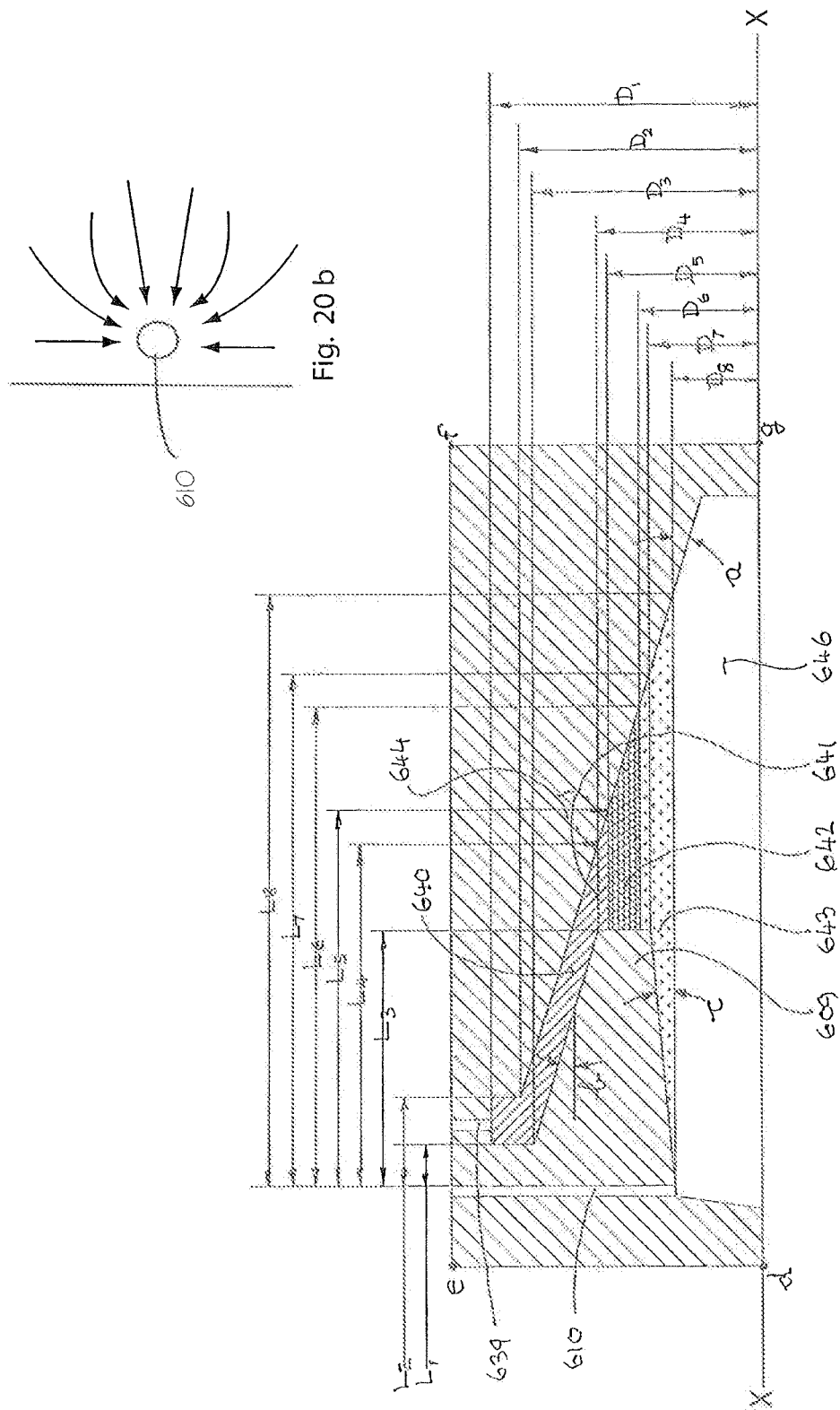

FIG. 20a. Simplified schematic of centrifuge chamber having a plenum at the end of the red blood cell channel and separated fluids.

FIG. 20b. Projection view of the plasma port of FIG. 20a with plasma fluid flow pattern represented by arrows.

Figure 21:
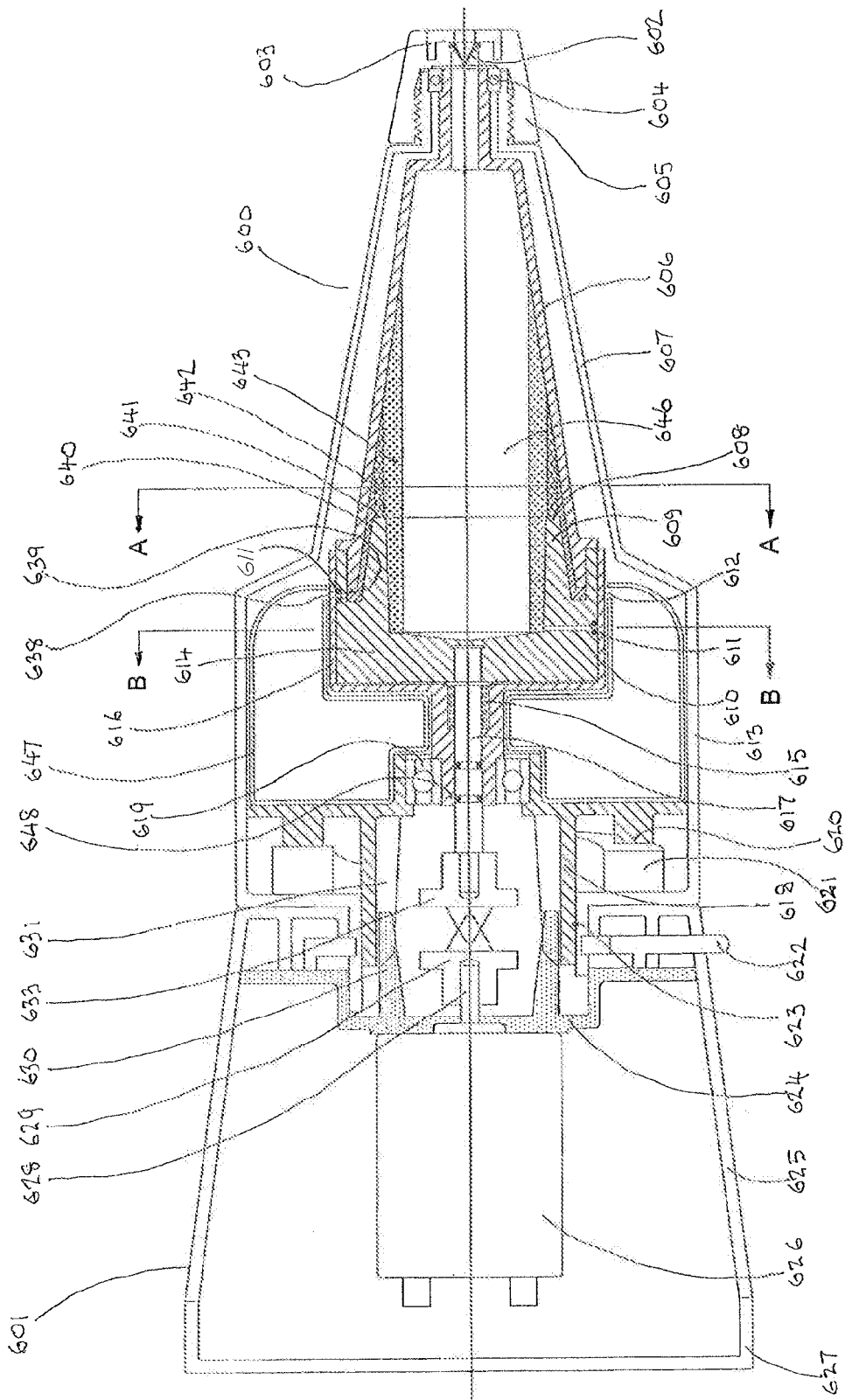

FIG. 21. Assembled centrifuge in running position, RBC valve open and RBC dump complete.

Figure 22:
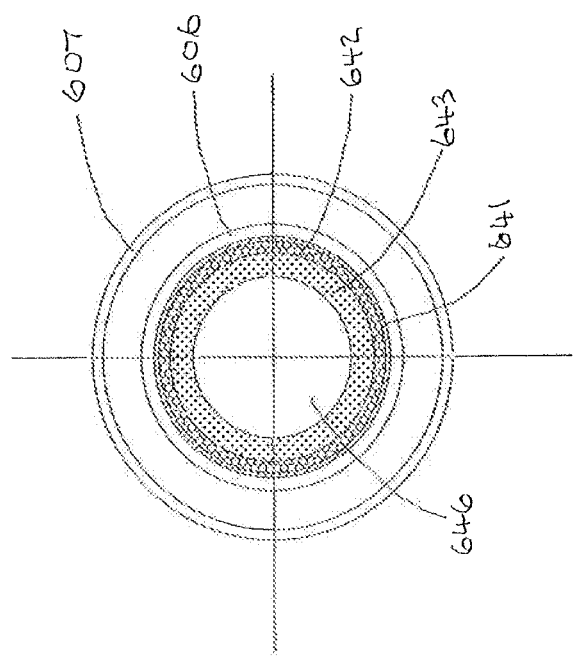

FIG. 22. Simplified transverse section of FIG. 21 at AA.

Figure 23:
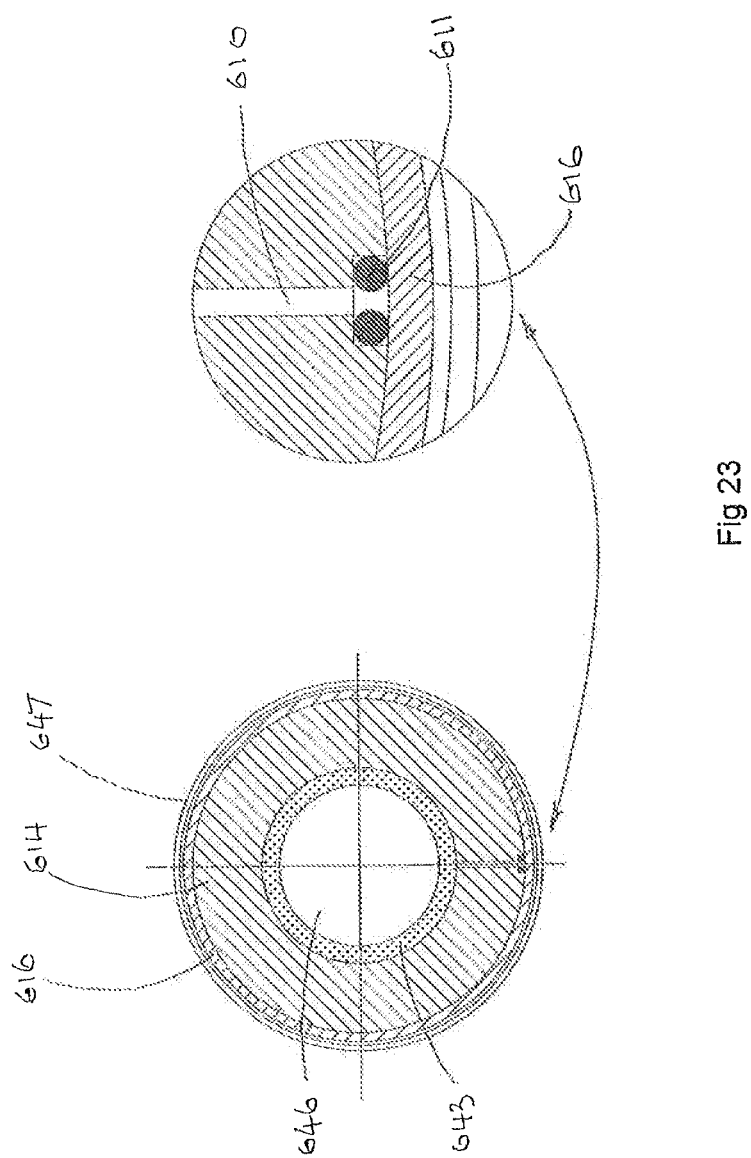

FIG. 23. Simplified transverse section of FIG. 21 through plasma valve at BB showing valve construction.

Figure 24:
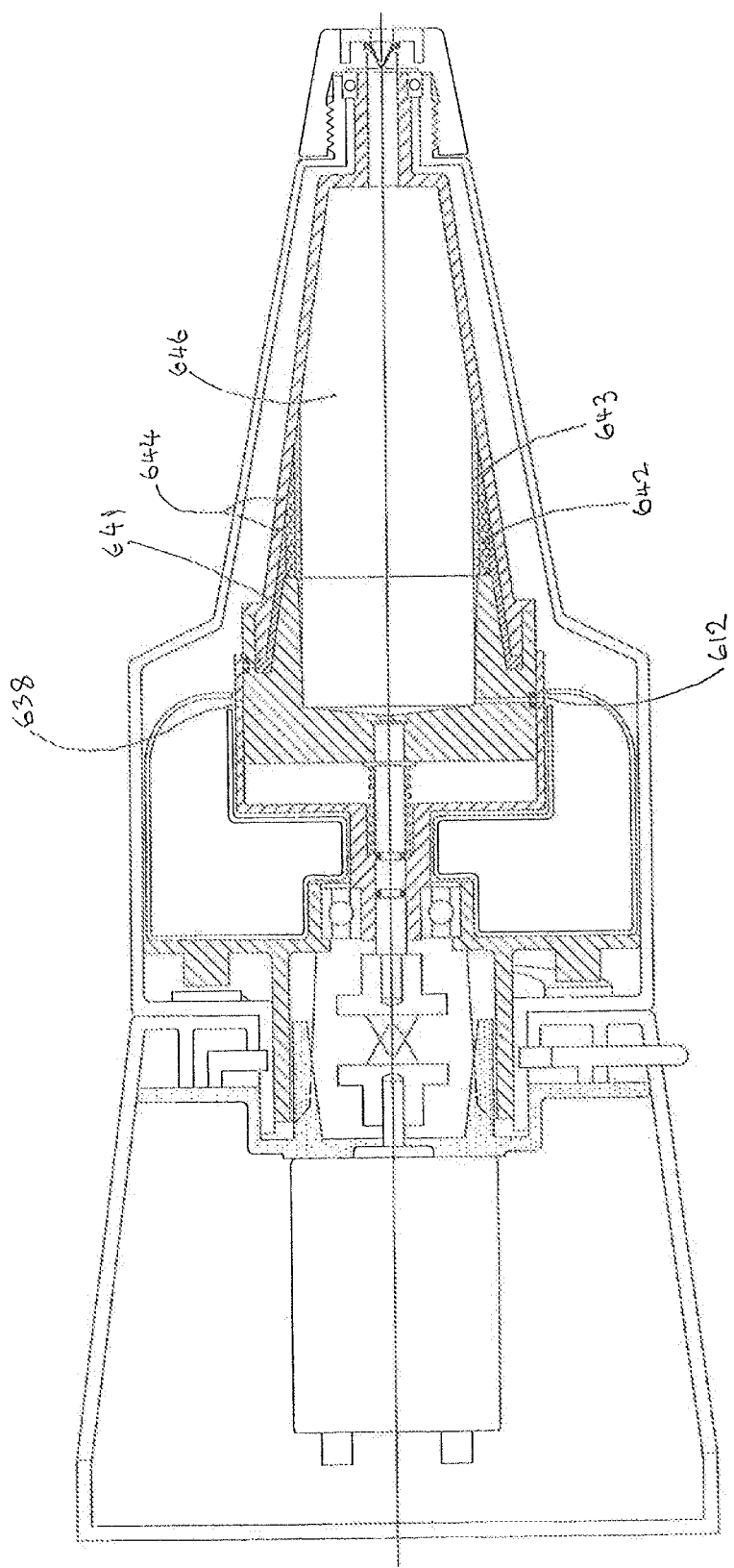

FIG. 24. Assembled centrifuge in running position, RBC valve shut, plasma valve open and plasma dump complete.

Figure 25:
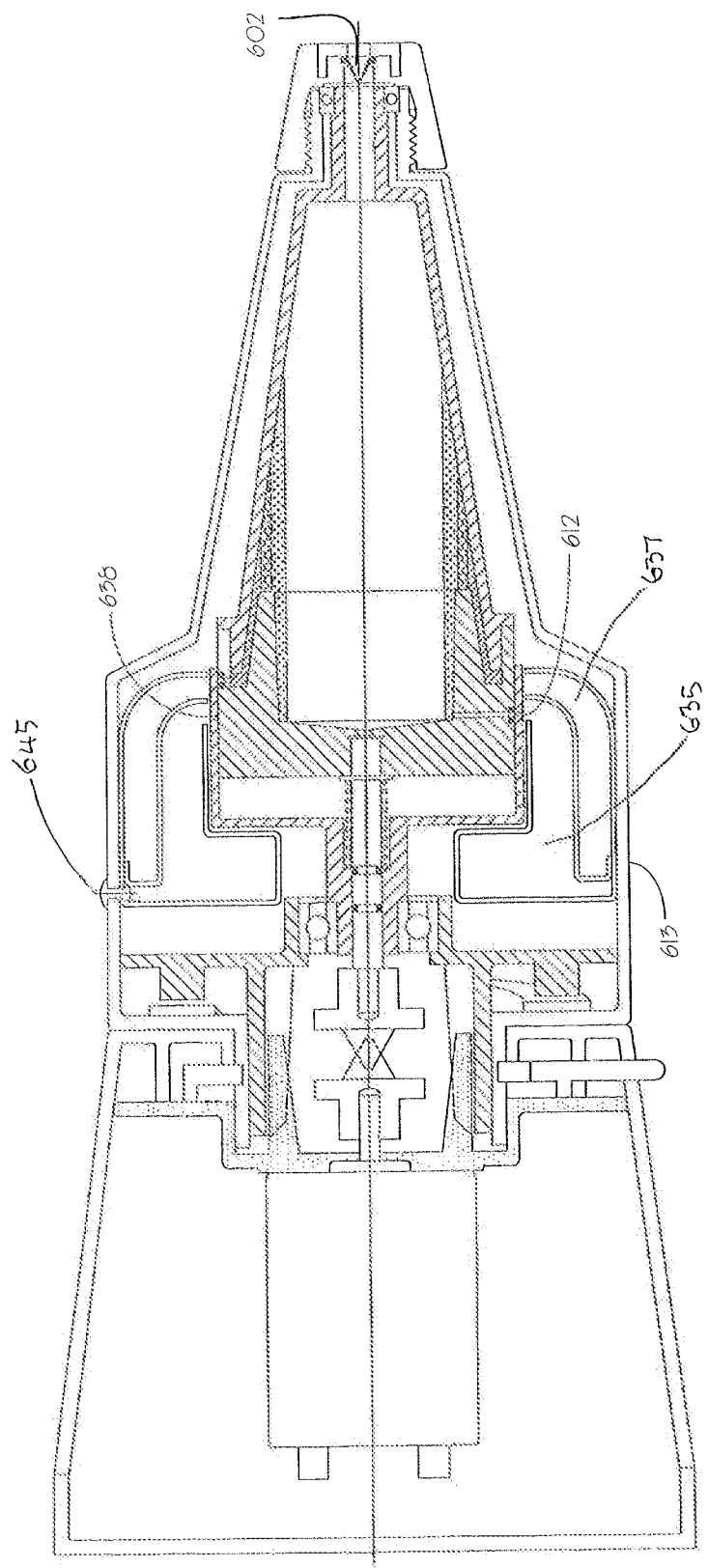

FIG. 25. Centrifuge with means for gathering Platelet Poor Plasma (PPP) in a separate receiver, shown in plasma collection phase of operation.

Figure 26:
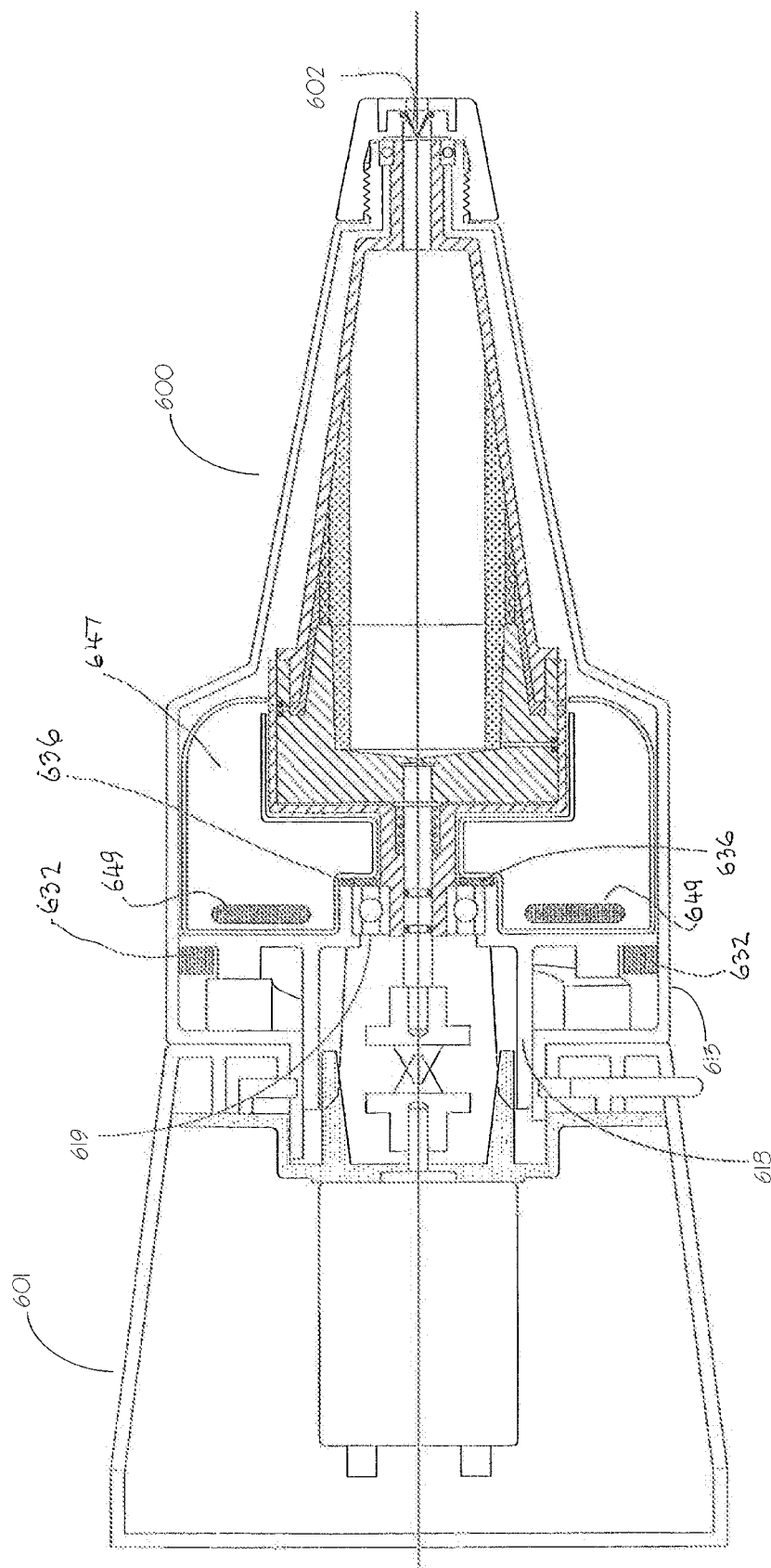

FIG. 26. Centrifuge with absorbent washers to capture blood products, shown at the end of the RBC dump phase.

FIG. 27a. Simplified schematic of centrifuge chamber having plena at the end of the red blood cell channel and at the plasma outlet, and separated fluids.

FIG. 27b. Projection view of the plasma port of FIG. 27A, with fluid flow pattern represented by arrows.

Figure 28:
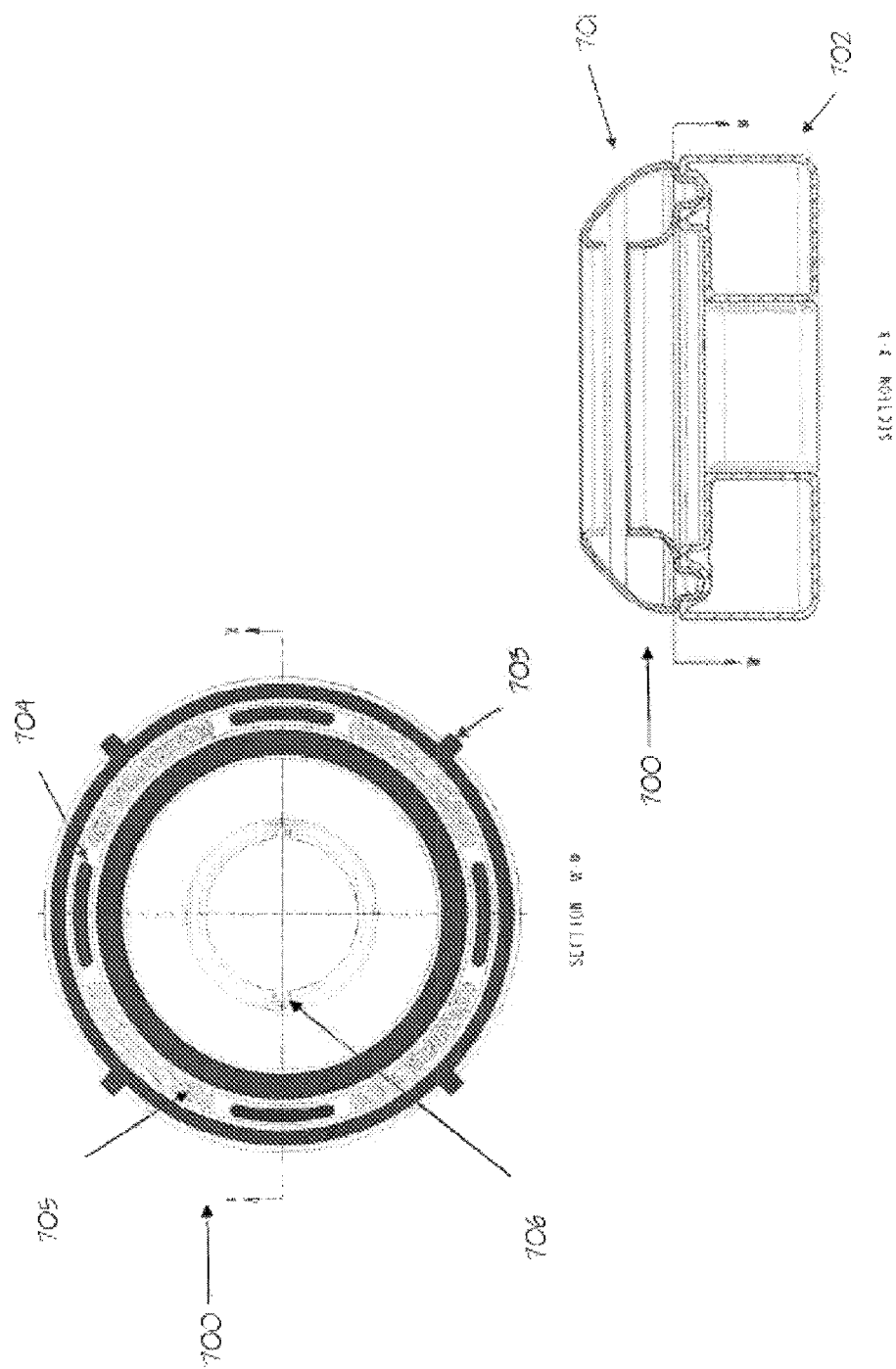

FIG. 28. Cross section views of alternate RBC-Plasma receiver with indexing valve, depicted in the closed position.

Figure 29:
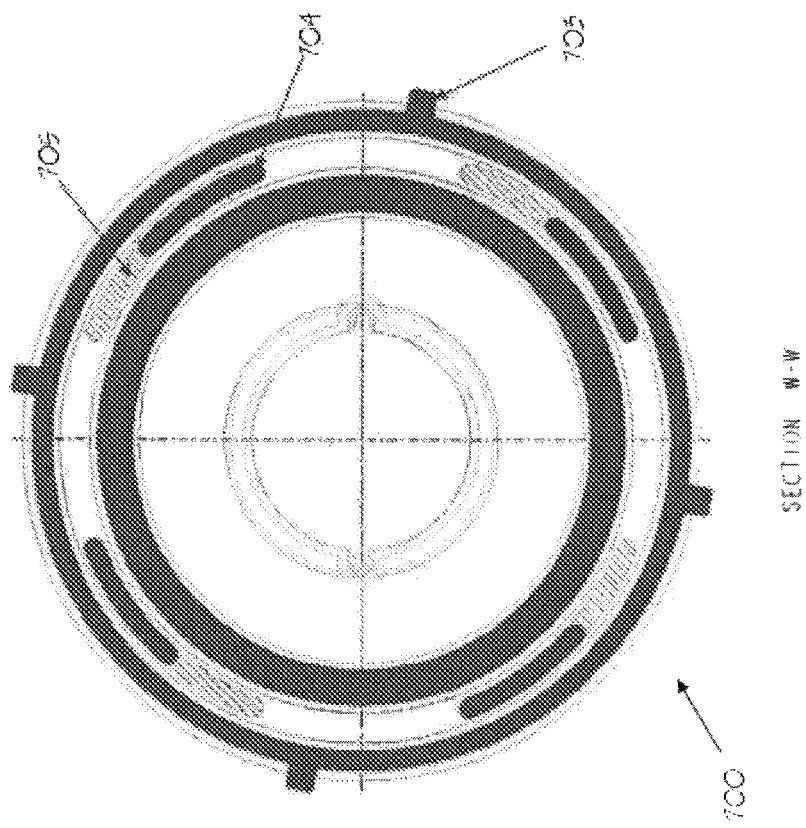

FIG. 29. Cross section view of alternate RBC-Plasma receiver with indexing valve showing valve in open position.

Figure 30:
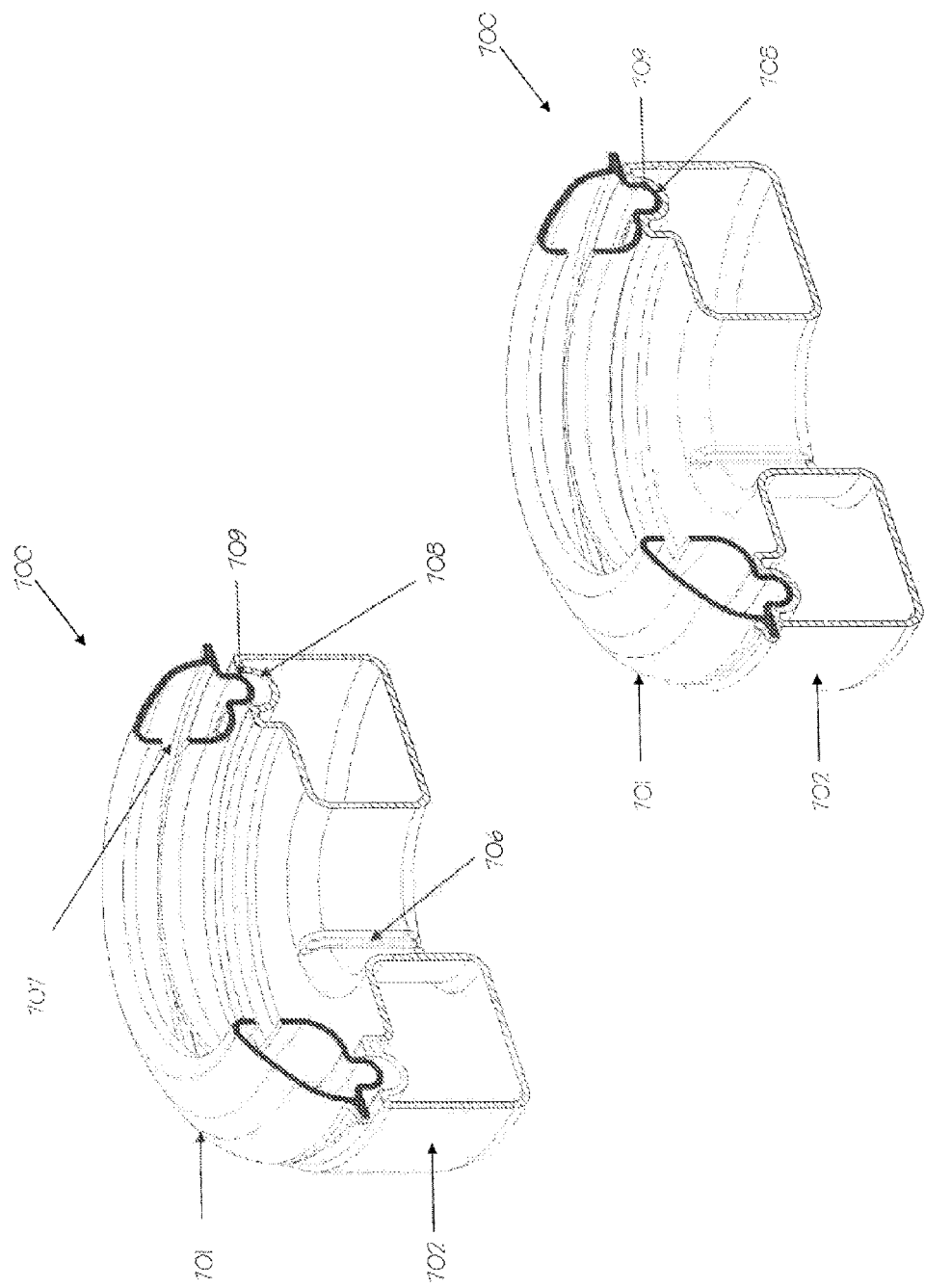

FIG. 30. Isometric cross section view of alternate RBC-Plasma receiver with indexing valve.

Figure 31:
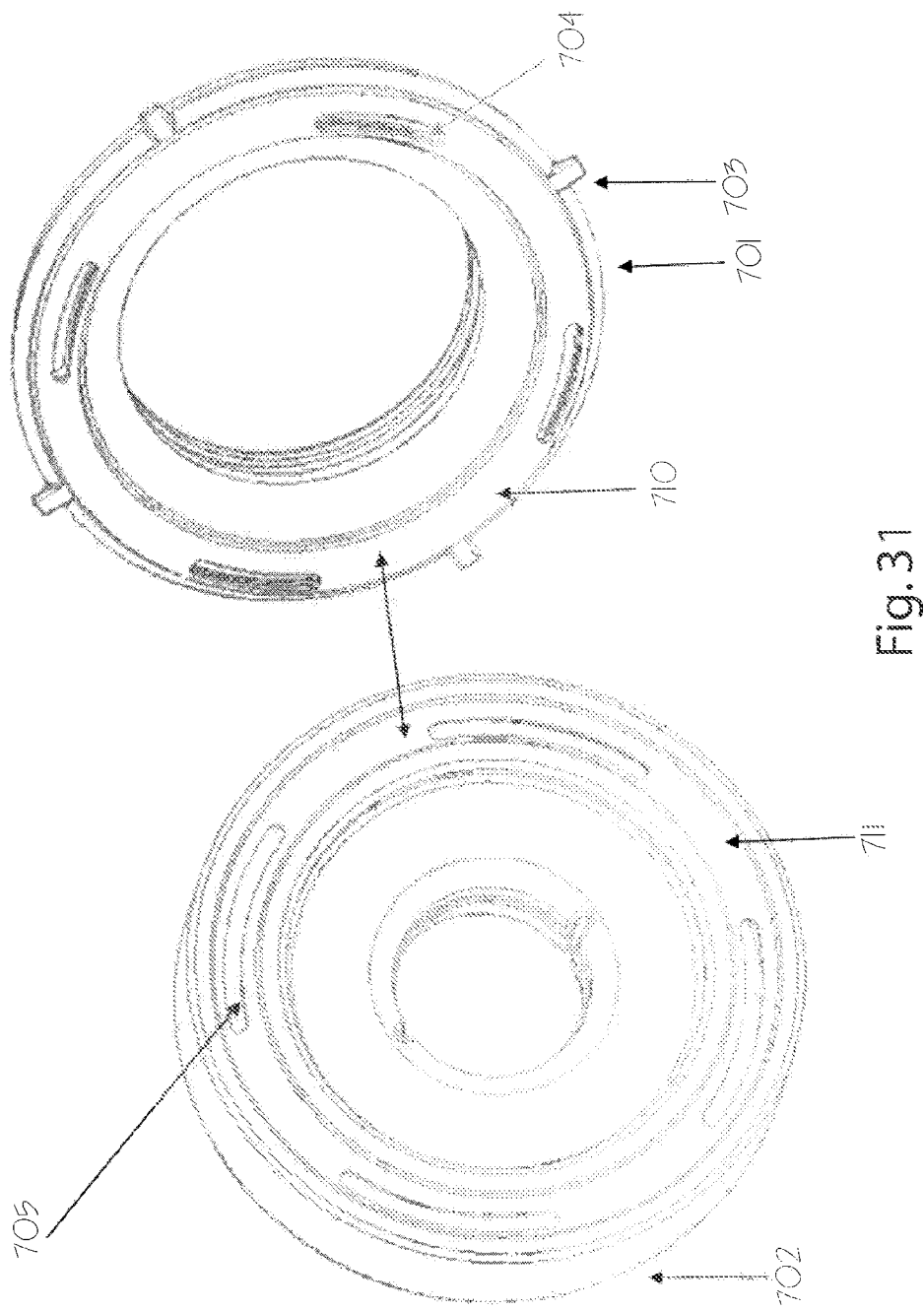

FIG. 31. Isometric view of disassembled alternate RBC-Plasma receiver with indexing valve.

Figure 32:
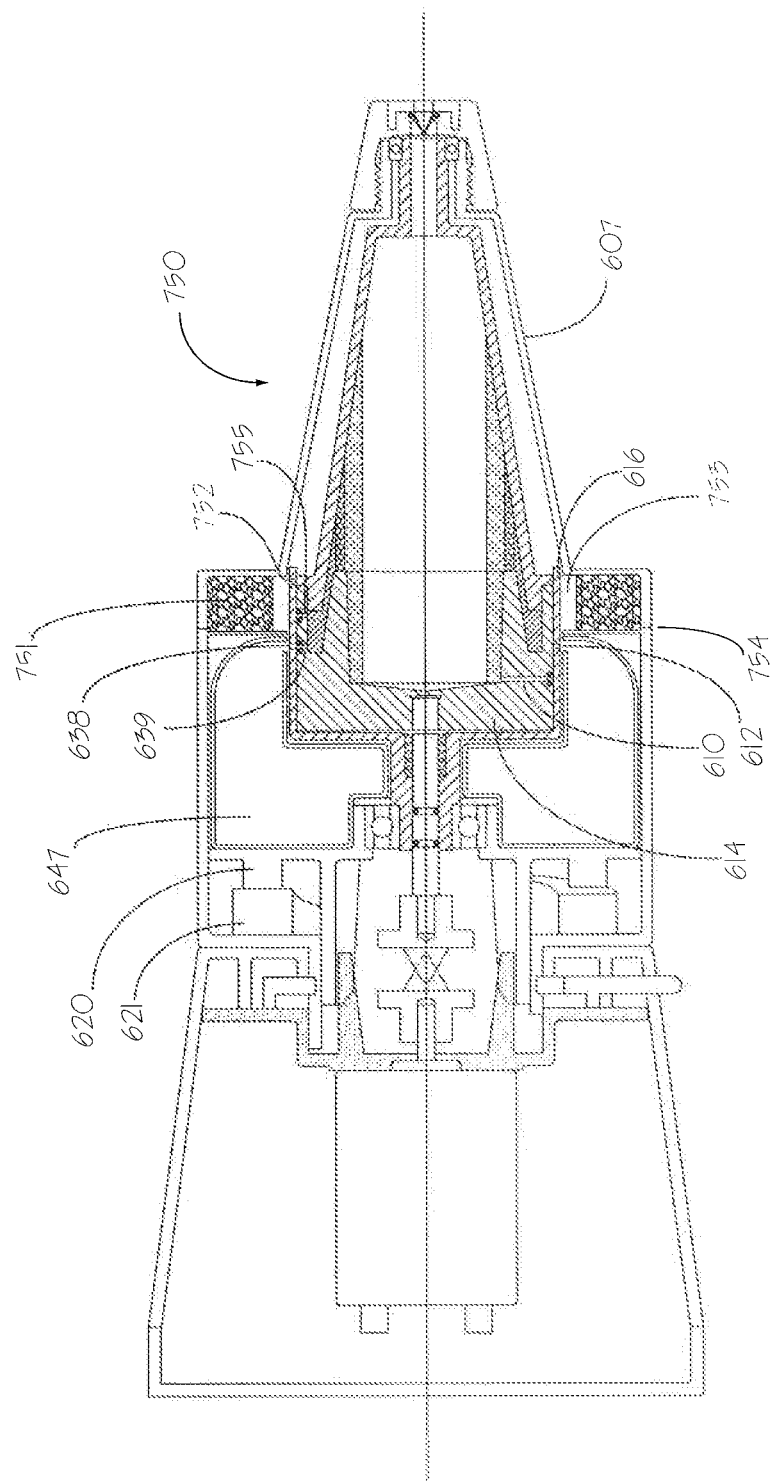

FIG. 32. Centrifuge with scaffold material in a compartment and arranged for receipt of buffy coat component.

FIG. 33. Simplified schematic of centrifuge chamber having a restriction feature in a portion of the circumferential channel and separated fluids.

Figure 33A:
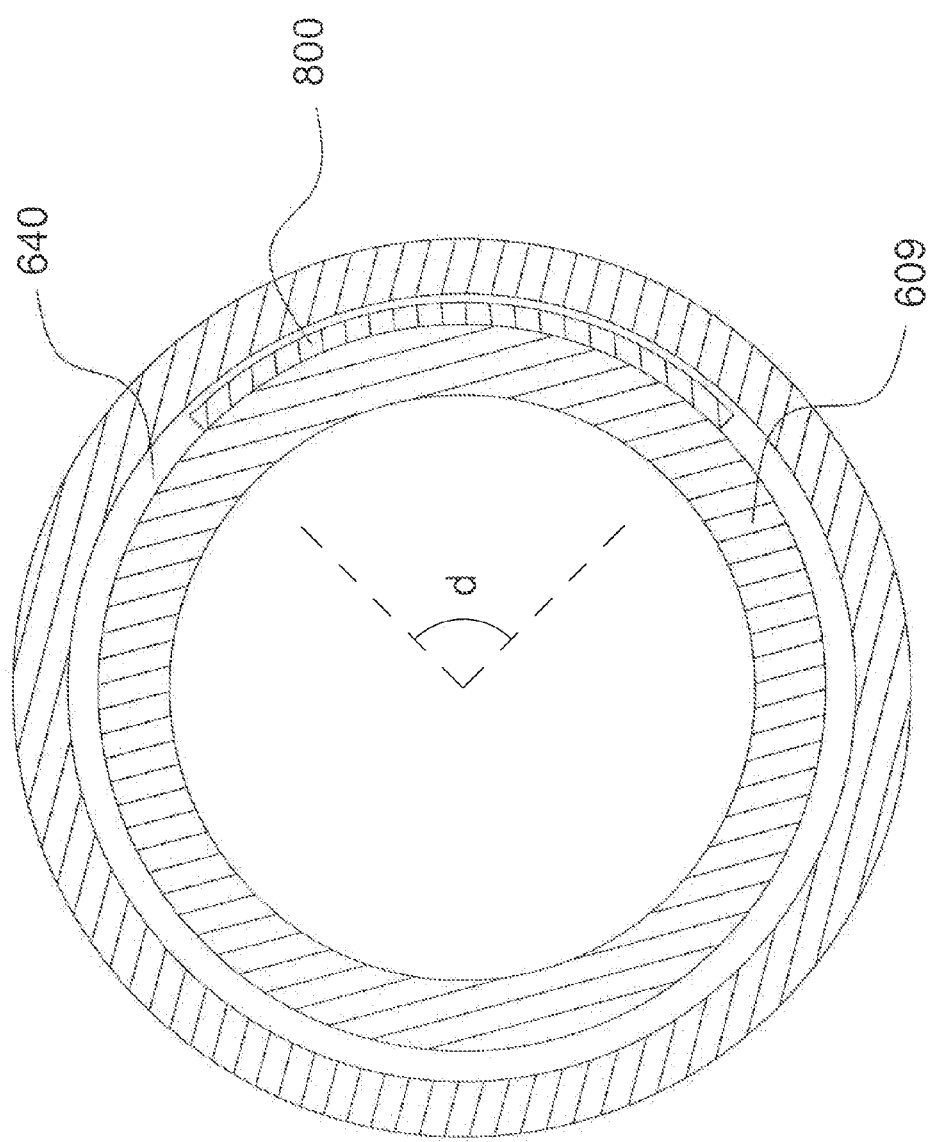

FIG. 33a. Transverse sectional view of section A-A of FIG. 33, with the portion of the circumferential channel corresponding to angle d featuring a restriction feature.

Figure 34:
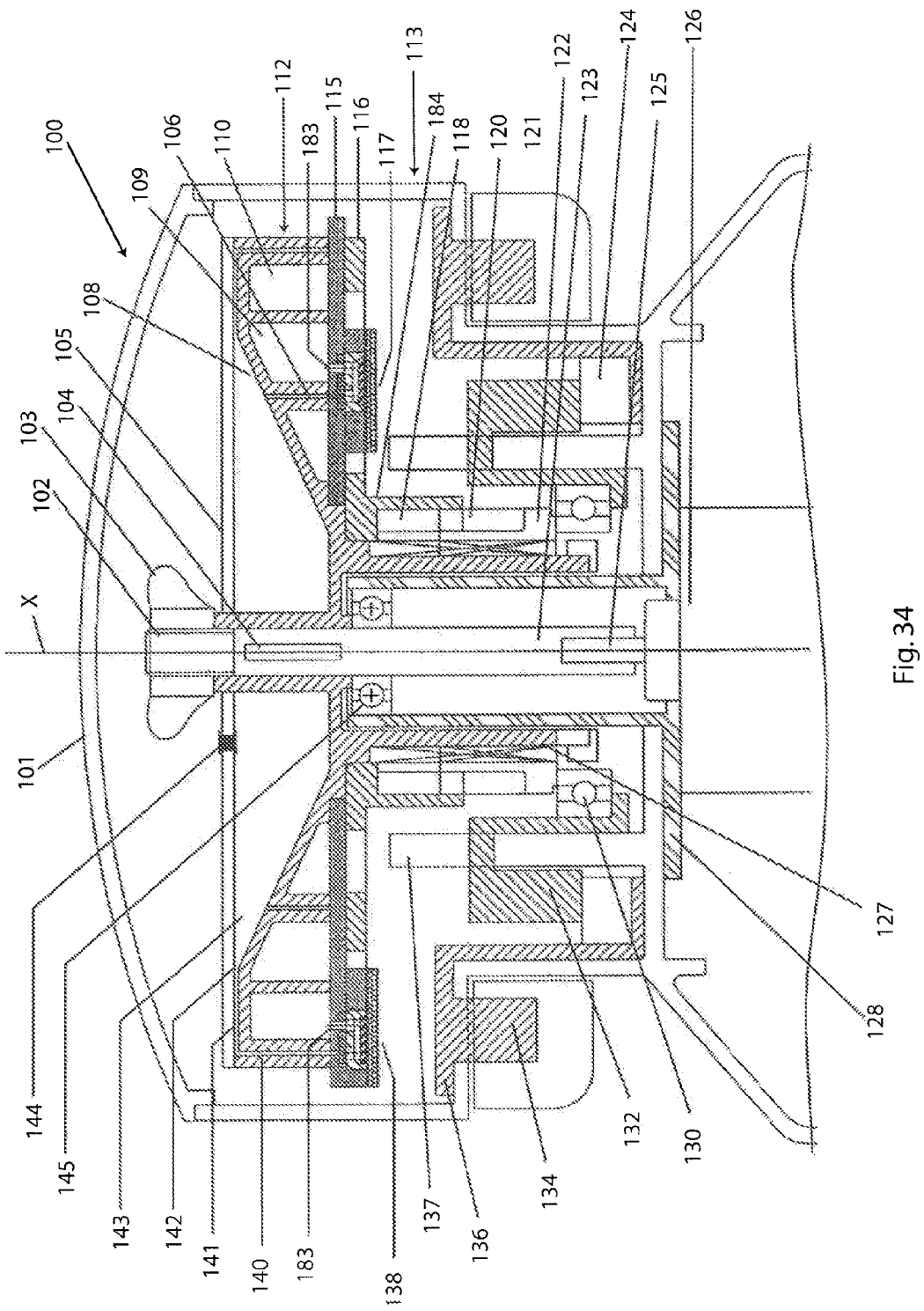

FIG. 34 Cross-sectional view of another alternative centrifuge with a disk-shaped rotating assembly.

Figure 35:
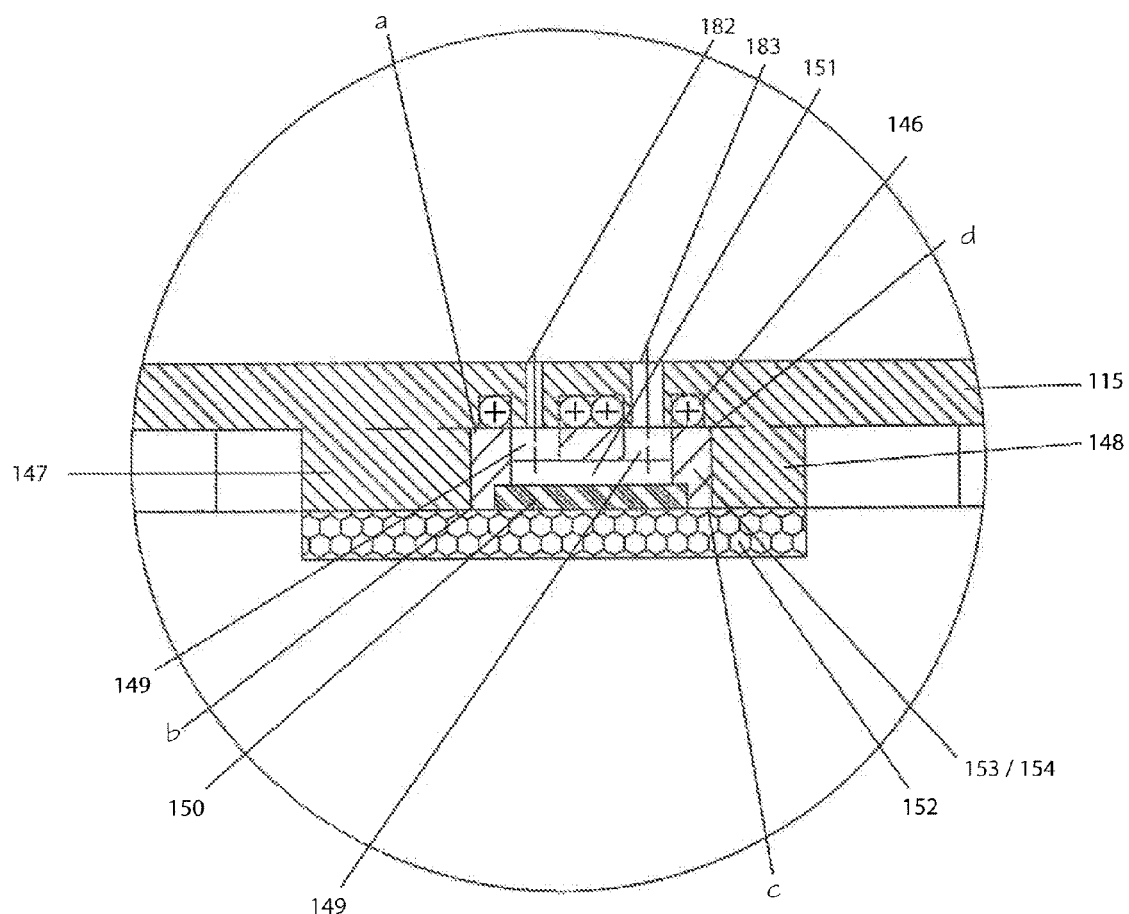

FIG. 35 Enlarged cross-sectional view the details of the valve arrangement of the disk-shaped rotating assembly of the centrifuge of FIG. 34.

Figure 36:
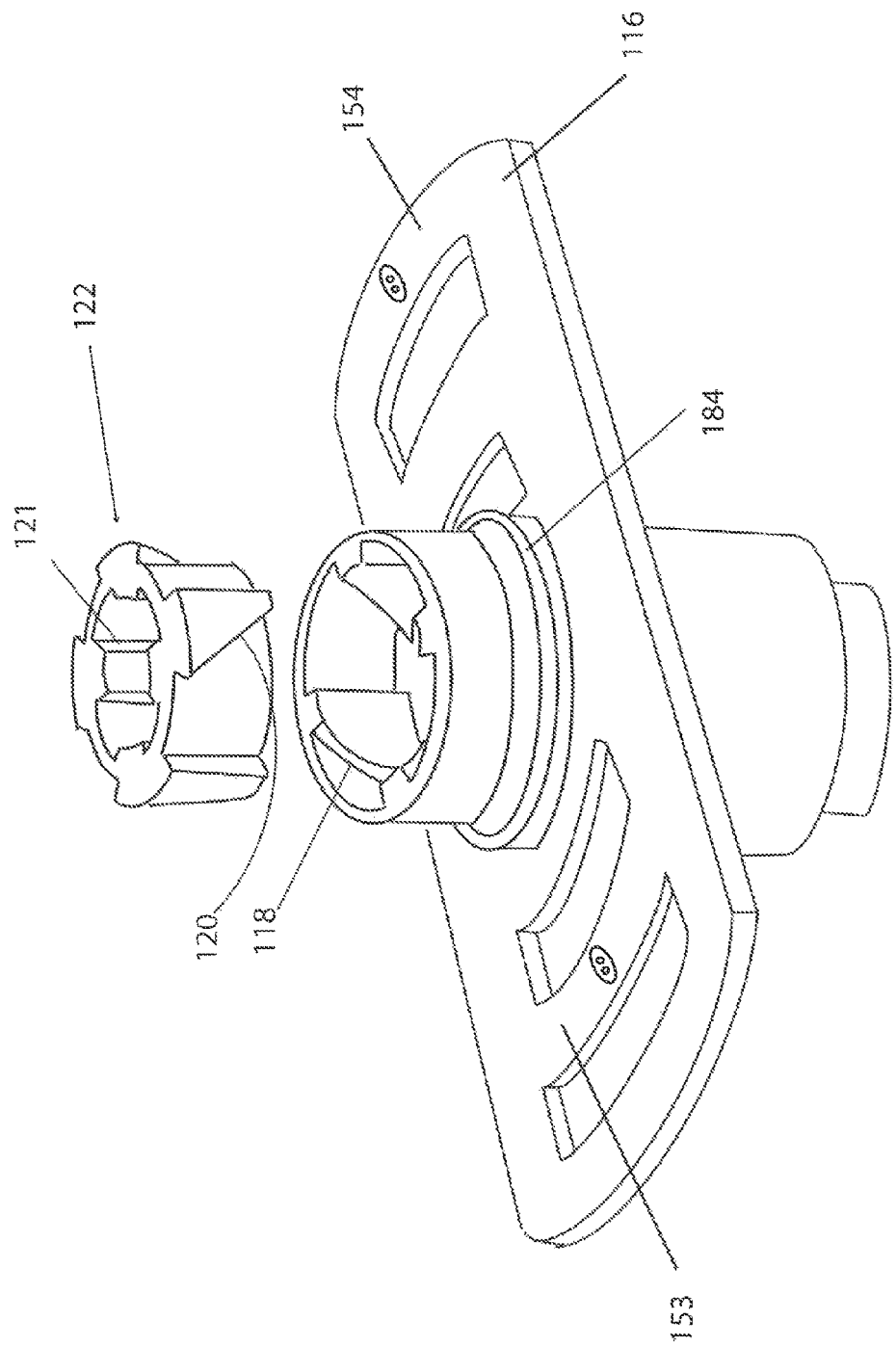

FIG. 36 Enlarged, exploded isometric view of components of the force transfer mechanism of the centrifuge of FIG. 34.

Figure 37:
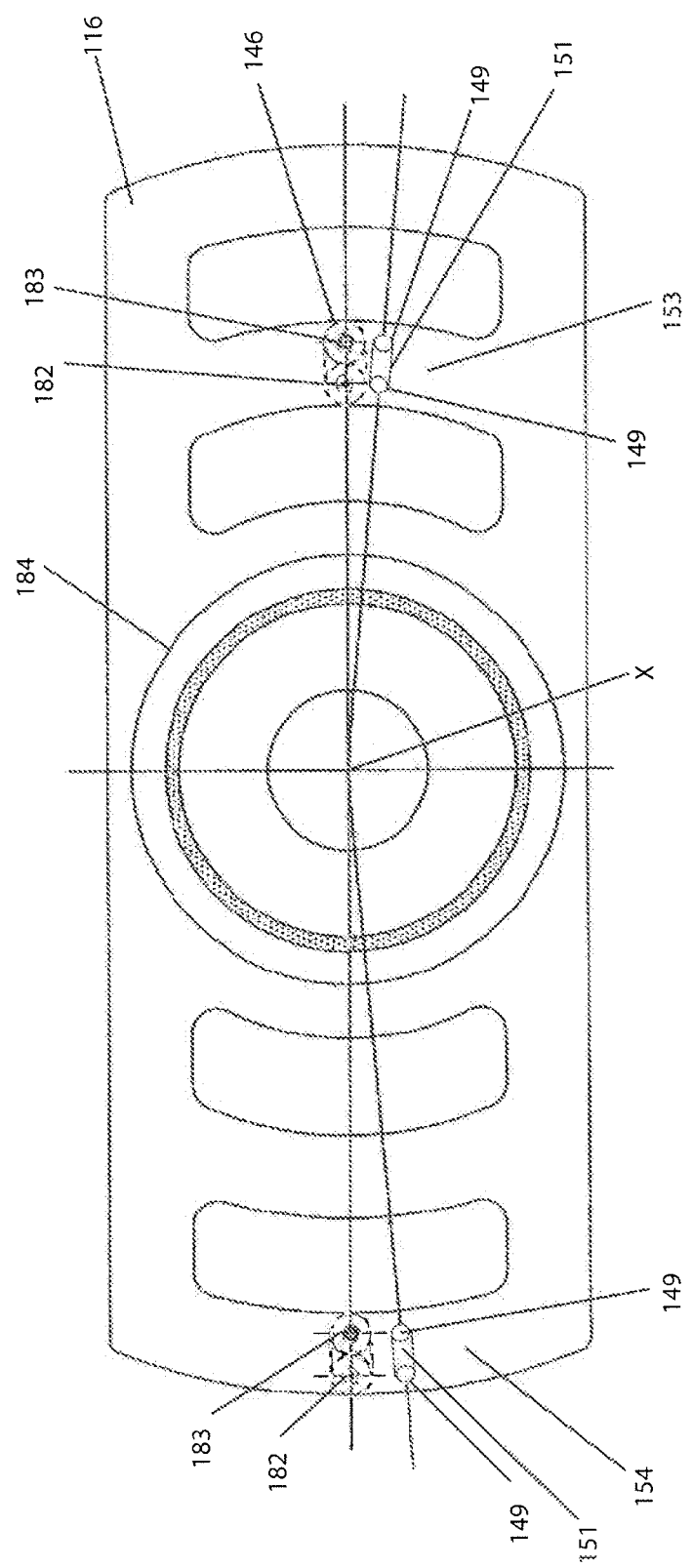

FIG. 37 Enlarged projection view of the valve components of the rotating assembly of the centrifuge of FIG. 34.

MODES FOR CARRYING OUT THE INVENTION

FIG. 1a provides an illustration for description of the principle of operation of the devices covered in this invention. A chamber of essentially frusto-conical shape 1, contains a mixture of several liquids of differing densities, and rotates about the longitudinal axis XX. The liquids 2, 3, and 4 separate into radially distinct layers as shown in section AA. The taper is beneficial in several ways, first it allows a small volume of liquid to offer a large radial depth (as shown at 11) compared with the radial depth the same volume would have if distributed over the whole length of a right circular cylinder of similar dimensions, see FIG. 1b at 14. Second, the taper provides a component of radial acceleration force that helps to scour the outer liquid constituent towards a port 9 placed at the larger cone diameter. Third, the taper also allows visualization of the constituent boundaries as axial locations such as 5 and 6 instead of radial locations such as 7 and 8 in some of the embodiments. It should be pointed out at this juncture that the term "taper" or "tapered" is used in its normal definitional sense, i.e., to become progressively smaller toward one end or to diminish gradually. Thus the taper of the chamber need not be linear, as shown in the exemplary embodiments contained herein, but may be arcuate or of other shapes as discussed below where it is recognized that any shape capable of high speed rotation can be utilizd, so long as there is an angled or tapered inner diameter to facilitate the appropriate flow of the red blood cells towards an RBC passage. In several embodiments the wall 12 of FIG. 1 moves toward the larger diameter and the frusto-conical volume reduces as one or more constituents are ported from the ports, for example at 9 and 10, leaving the center constituent 3 at its original volume. In other embodiments wall 12 remains in place and air is introduced on the center line at 13 to permit the porting of constituents 2 and 4 at 9 and 10 as the air core expands to replace the discharged constituents.

FIG. 2 is a mainly longitudinal section of an essentially circular device, external housing not shown. In FIG. 2 a liquid tight variable volume, the chamber (BSC), is formed from a tapered barrel 206, piston 210, piston seal 211 and end cap 215. Piston 210 and seal 211 are biased toward the larger end of the BSC by spring 209. Larger end of barrel 206 is closed by end cap 215. The inner surface of the end cap 215 forms the larger diameter end wall of the chamber, with the inner surface of the barrel 206 forming the chamber's tapering side wall. In the case where this device is used to enrich plasma from whole blood, end cap 215 has passages 216 and 217 bored within to permit the passage of red blood cells from passage 217 and plasma from passage 216. Passage 217 is shown passing through the outside skirt of the end cap that is in line with the outside wall of tapered barrel 206. A passage bored 90° from that shown at 217; through the inside face of end cap 215 at the maximum ID position would be functionally equivalent to the one shown at 217 and would have a shape similar to passage 216. Passages 217 and 216 connect with valves formed by O-rings 218 compressed in recesses 226 operating in concert with ports 228 and 227 respectively in sleeve 213. These valve components are shown enlarged in FIGS. 3b and 3d. Sleeve 213 fits slidably on end cap 215 to permit the port holes 228 and 227 to connect with the passages 216 and 217 at appropriate points in the operation. Sleeve 213 is keyed to end cap 215 to permit the transmission of rotary motion between these constituents (key not shown). Insert 219 is fastened to end cap 215 to provide an axle for the ball bearing 220 supporting the left hand end of the rotating assembly. Since the sleeve 213 is rotating with the chamber, a ball bearing 221 is provide to connect the sleeve to a non-revolving knob 223 via collar 225 and rods 222. The knob and sleeve can be placed in 3 positions: first position, port 228 open and port 227 closed: second position, both ports 227 and 228 closed: third position, port 228 closed and port 227 open. Barrel 206 is fastened to the shaft 205 of electric motor 201 using screw 207. No additional bearings are provided at the motor end, the motor bearings sufficing to support the barrel. The complete assembly is supported by a frame 208, the insert bearing 220 and the motor 201 being located on this same frame. The rotating components all rotate about axis XX.

To use the device for preparing PRP, a syringe 233 with needle 234, filled with anti-coagulated whole blood is inserted into the device through elastomeric seal 214 to load the chamber with whole blood 229. Knob 223 is placed in the first position to allow air to discharge from port 228 as the chamber is filled with blood. Whole blood 229 fully charges the chamber pushing the piston 210 and seal 211 to the far right, compressing spring 209.

FIG. 3a, a cross section at AA in FIG. 2, clarifies the construction of the knob 223 and rod components 222. FIG. 3b is a cross section at BB in FIG. 2 showing details for the valve components, those being the recess 226 in end cap 215, O-ring 218 and port 228 in sleeve 213 (the construction of the valve for port 227 is the same). FIG. 3c shows the section at CC of FIG. 2.

Once the chamber has been charged with whole blood, the knob and sleeve are placed in the second position with both valves closed, the syringe 223 is removed and the motor started. The motor is then run for times between 15 and 90 seconds depending on the speed used. Speeds of 10,000 rpm to 25,000 rpm have been used, developing centrifugal accelerations at the outside of the spinning chamber from 1000 g to 6000 g.

FIG. 4 shows the device of FIG. 2 in operation rotating at speed. The RBC port 228 and the plasma port 227 are both closed. The boundary between the RBC layer and the plasma layer is shown at 237. The piston 210 is still at the as-charged position and the spring 209 is fully compressed. The spring has two functions, it moves the piston to the left as red blood cells are discharged from the chamber through port 228, and the spring creates a significant minimum pressure in the revolving liquid: this prevents the core of the spinning liquid from reaching the vapor pressure of the liquids and may suppress cell damage in some circumstances.

Once the red blood cells and the plasma have separated, with the device still rotating, the knob and sleeve are placed in the first position and red blood cells are discharged from port 228 into the casing (casing not shown, but see FIGS. 17 and 18) surrounding the device. FIG. 5 shows the situation at the mid-point of the RBC 231 discharge when the piston 210 is in mid position. Once the majority of red blood cells have been discharged the valve is placed in the third position and plasma 230 is eliminated from port 227. FIG. 6 shows the situation at the end of the enrichment process: the plasma port 227 is still open and the piston is close to the far left position: platelets that have a specific gravity between that of plasma and RBCs are trapped at the RBC-plasma boundary layer 237; the plasma port is about to be closed and the motor stopped.

Typical volumes for the chamber are 20-100 mL, and the amount of enriched plasma removed at the termination of the procedure is approximately a quarter to an eighth of the original volume depending on the degree of enrichment desired.

In order to retain all the platelets and other factors gathering at the RBC-plasma boundary, it is essential to close port 228 before all the RBCs have been removed, otherwise there is the danger of these constituents flowing out with the last RBCs. To ensure that this does not occur, the blood sample hematocrit value is used to judge the residual volume of the chamber when the RBC port must be closed. This volume is observable as a piston axial position, and the valve is moved from position one to position three as the piston reaches this predetermined position.

The device described in FIGS. 2 through 6 uses a piston and seal traveling in a tapered tube, but a right circular cylinder may well function adequately for mixtures of liquids other than blood and where the residual volume of the first liquid discharged is not too critical. The tapered tube has the advantages mentioned in the discussion of FIG. 1. The position of the piston can be judged visually by the operator relative to graduations on the barrel (not shown), or an optical detector and automatic valve operation system can be used (not shown).

Since the residual enriched plasma is injected back into the patient the materials used for this device have to be medical grade materials, at least for those constituents contacting the blood. Polycarbonate or PTE are suitable for the barrel 206, end cap 215, sleeve 213, frame 208, knob 223 and collar 225. Insert 219 is of a suitable grade of passivated stainless steel such as 416 or 420. The ball bearings have to do duty at high speed but operate for very short times so stainless steel bearings of grade ABMA 1-3 are adequate. O-rings 218 and seal 211 are of silicone rubber. Since the motor does not contact blood, industrial motors (for example those made by Mabucci) are adequate.

FIG. 7 shows an embodiment with a flexible bladder 312 that initially conforms to the bore of the barrel 306, the bladder providing a variable volume chamber through its ability to invert as shown in FIGS. 10 and 11. This embodiment may serve to reduce the effect of entrapped air bubbles.

In FIG. 7 a liquid tight variable volume centrifuge chamber (the BSC) is formed from a tapered barrel 306 containing a molded bladder 312, and end cap 315. The bladder is captured in a return fold 339 between a barrel projection 338 and the end cap 315. Larger end of barrel 306 is closed by end cap 315. In the case where this device is used to enrich plasma from whole blood, end cap 315 has passages 316 and 317 bored within to permit the passage of red blood cells from passage 317 and plasma from passage 316. Passages 317 and 316 connect with valves formed by O-rings 318 compressed in recesses 326 operating in concert with ports 328 and 327 respectively in sleeve 313. Sleeve 313 fits slidably on end cap 315 to permit the ports 328 and 327 to connect with the passages 316 and 317 at appropriate points in the operation. The knob 323 and sleeve 313 can be placed in 3 positions: first position, port 328 open and port 327 closed: second position, both ports 327 and 328 closed: third position, port 328 closed and port 327 open. Sleeve 313 is keyed to end cap 315 to permit the transmission of rotary motion between these constituents (key not shown). Insert 319 is fastened to end cap 315 to provide an axle for the ball bearing 320 supporting the left hand end of the rotating assembly. Since the sleeve 313 is rotating with the chamber a ball bearing 321 is provide to connect the sleeve to a non-revolving knob 323 via collar 325 and rods 322. Barrel 306 is fastened to the shaft 305 of electric motor 301 using screw 307. No additional bearings are provided at the motor end, the motor bearings sufficing to support the barrel. The complete assembly is supported by a frame 308, the insert bearing 320 and the motor 301 being located on this frame. The revolving components all rotate about axis XX. In this illustration the sleeve is in the first position to keep the port 328 open for porting of air as the chamber is charged with blood, and the plasma port 327 is closed. Whole blood 329 fully charges the chamber. An elastomeric seal 314 permits the introduction of a needle 334 for the passage of whole blood into the chamber before the start of rotation, and removal of enriched plasma at the cessation of action.

FIG. 8 is a transverse cross section of the device shown in FIG. 7 at section AA. Whole blood 329 fills the BSC and bladder 312 which is fully in contact with barrel 306. Frame 308 runs under the rotating assembly.

FIG. 9 shows the device of FIG. 7 in operation rotating at speed. The sleeve 313 is in position two with both ports 327 and 328 closed. The boundary between RBCs 331 and plasma 330 is shown at 337. The bladder is still against the barrel now under the influence of the pressure developed by the spinning liquid mixture.

FIG. 10 depicts the situation after spinning for 60 seconds or so. The sleeve 313 is placed in position one, port 328 is open and RBCs 331 are being discharged through port 328. Plasma port 327 is closed. The bladder has moved to the left to compensate for the volume of RBCs that have been discharged. The shape adopted by the bladder is a balance between the forces developed by liquid pressure pushing the bladder to the right and atmospheric pressure (via vent 332) pushing the bladder to the left. Since the pressure at the center of the spinning liquid is near absolute zero the atmospheric pressure exceeds the left hand pressure that has been developed up to a certain radius, hence the re-entrant shape of the bladder. The volume of plasma 330 has remained the same as when introduced. The boundary between RBCs and plasma is shown at 337. In this view the RBC discharge is about to be stopped since the residual RBC volume 331 is low enough.

FIG. 11 illustrates the final position for the bladder 312 while the rotation continues but just prior to stopping. Sleeve 313 is in position three, RBC port 328 is closed and plasma port 327 is still open. Plasma has been discharged through port 327 and is about to be cut off by the bladder rolling onto end cap 315 and cutting off the passage 316. This illustrates the minimum volume of enriched plasma 330. At this point the sleeve 313 is moved to position two with both ports closed and the rotation is then stopped; the residual liquid is removed using a syringe in a similar manner to the charging described in FIG. 7.

Materials for the device of FIGS. 7 through 11 are similar to those for the device of FIGS. 2 through 6: the bladder by example can be made of silicone rubber, polyurethane or polyvinylchloride.

For the previous device 200 the piston position provided the signal for closure of the RBC port 328. In the case of the bladder the inverted bladder rolls along the tapered barrel bore, the axial position of the reverse edge providing (labeled 312 in FIG. 11) the volume and the signal for port closure. The cut-off of the plasma discharge is automatic as the bladder rolls over the port passage 316.

The device described in FIGS. 12 through 16 utilizes an air core and uses no bladder or piston.

The device of FIG. 12 is very similar in construction to the two previous embodiments, with a BSC formed from a barrel 406 and end cap 415. The inner surface of the end cap 415 forms the larger diameter end wall of the chamber, with the inner surface of the barrel 406 forming the chamber's tapering side wall. In this illustration whole blood 429 from syringe 433 fills the centrifuge chamber through needle 434 with both ports 428 and 427 closed. Air displaced by the blood leaks out through the clearance between the needle 434 and insert 419 bore as the blood is injected. FIG. 13 shows the circular section nature of FIG. 12. Once the charging syringe is removed, the motor is started and the chamber is rotated at 10,000 to 20,000 rpm for approximately one minute. At this point the sleeve 413 is moved to the second position, and RBCs are discharged through port 428 until the point shown in FIG. 14 where the minimum RBCs 431 remain. Meanwhile, the plasma adopts the region or layer 430, and a boundary 440 forms at the plasma-air radial interface, the air core 438 having entered through the bore of insert 419 (via a filter in the housing not shown, but see FIGS. 17 and 18). At this juncture the sleeve is moved to the third position, port 428 closed and port 427 opened. With this preferred device there is no bladder or piston to observe, so the operator observes the axial interface 436 between the RBCs 431 and the plasma 430 of the mixture through the transparent barrel to determine when to manually close the RBC port 428 and open the plasma port 427. With blood, this mixture interface is easy to see and can be automated with an optical detector. The difference in electrical resistivity between red blood cells and plasma can also be used to trigger an indicator or automated valve. An alternative way of determining the point at which to shut the RBC port is to use time. After one minute of running to separate the constituents of the blood, the RBC port is opened and a timer started. Since the pressure generated in the centrifuge is a predictable function of liquid specific gravity and running speed, and since the RBC port is a precisely calibrated orifice, the flow rate being discharged, and hence time can be computed for a given hematocrit value.

With the motor still running, the plasma discharges through port 427 until it reaches the situation in FIG. 15 where the residual RBCs are at layer 431 and the residual plasma at layer 430. The sleeve is then moved to the second position to close both ports. In the case of plasma the passage 416 is placed at a precise radial location to give an accurate final volume since no further flow of plasma will occur once the air core 438 has grown to that passage radial location. The motor is then stopped and the device placed on end, with the motor downward, so that the rotation axis is vertical as shown in FIG. 16. The remaining enriched plasma with some RBCs is removed by syringe and needle as illustrated.

An enclosure suitable for various embodiments discussed in this application is described in FIGS. 17 and 18; however these two figures show the enclosure applied specifically to the air core embodiment of FIGS. 12 through 16. The frame 508 is mounted to a battery power pack 503 that acts as the base for the enclosure. An outer casing 500 surrounds the centrifuge and is fastened to the battery pack 503, the joint being liquid and air-tight. A valve selector knob 545, integral with eccentric 546 and pin 547, is mounted in the casing such that the selector knob 545 can be turned by the operator to actuate the internal knob 523 via the pin 547 in groove 548 and hence the collar 525 and valve sleeve 513. In FIG. 17 the motor 501 driving the chamber BSC is controlled manually by switch 504 connected to battery pack 503 by wires 550. A bush 543 mounted at the left hand end of the enclosure 500 provides alignment for the entry of the syringe (433 of FIG. 12) needle when charging the chamber with whole blood or when extracting the enriched plasma. Immediately adjacent to bush 543 is a porous flexible pierceable filter 544. This filter has two functions: It filters the air entering the core of the centrifuge when it is running, and it prevents the egress of any aerosols into the atmosphere of blood fragments generated as the centrifuge discharges RBCs or plasma into the casing. A small slit in the filter allows the charging syringe needle to enter without damaging the effectiveness of the filter. Covering most of the interior walls of the casing 500 is a highly absorbent lining 542 to absorb the RBCS and plasma discharged into the casing as the air core 538 enlarges and the enrichment process proceeds. A lens and mask 549 placed in the wall of the casing 500 permits the operator to view the axial interface 536 of the RBCs and plasma as the process of enrichment proceeds. The mask and lens are chosen to enhance the contrast of the image seen of the liquid separation interface 536.

A photo detector (not shown) can be placed in the location of the lens to provide an electrical signal of the progress of the liquid separation interfaces, and an electromagnet actuator can drive the valve selector knob 545. These electrical elements in conjunction with a manual switch can be used to control the entire process once the motor has started.

From tests to date it would seem feasible in some applications to use a simple timer program to schedule the sleeve motions. For example, the following sequence can operate off a timer once the chamber is charged with blood, a) start motor, run for 60 seconds b) open RBC port and discharge RBCs for 30 seconds, c) close RBC port and open plasma port and run for 30 seconds, d) close both ports, and stop motor. Such a device might require the addition of a means of manually inserting the patient's hematocrit number to allow for varying proportions of RBCs to plasma.

Table 1 gives typical data obtained for the air core device of FIGS. 12 through 16 using porcine blood. The data was obtained with runs of one minute for the initial separation and approximately one more minute to discharge the RBCs and plasma.

TABLE 1

| Sample | Platelet Count (×10³/microliter) | Platelet Concentration Factor | % Platelet Recovery | % Red Blood Cells Removed |
|---|---|---|---|---|
| Baseline | 229 | NA | NA | NA |
| Run 1 | 1656 | 7.2 | 100 | 93 |
| Run 2 | 1457 | 6.4 | 88 | 92 |
| Run 3 | 1446 | 6.3 | 87 | 93 |
| Run 4 | 1685 | 7.3 | 100 | 94 |

For all three embodiments discussed, piston, bladder and air core, the size and position of the ports and passages are very important. As the centrifuge rotates, the pressure developed within the chamber varies as the square of the speed and the square of the radius of rotation. To gain manual control over the discharge of constituents the discharge needs to take place over a manageable time. The RBC port for example needs to be sized to allow passage of the RBCs over a period of about 30 seconds. Conditions must be selected to allow the RBC port to function without blockage as the RBCs try to clump, and flow has to be kept low enough to stop the platelets from being swirled into the exit vortex. For centrifuges using whole blood samples of approximately 30 mL, it has been found that RBC ports of the order 0.008 inch diameter work well if speeds are in the region 15,000 to 20,000 rpm and chamber barrels are about 1.0 to 1.25 inch in diameter at the largest point. Plasma ports can be larger since the risk of losing the platelets is less: values of about 0.010 inch diameter are adequate. Placement of the plasma ports relative to the center axis of rotation has a direct effect on the attainable concentration factor. The closer to the center, the less plasma is removed and less concentration is achievable. Additionally, in various embodiments of the invention discussed it will be noticed that a small annulus 241, 341, 441, 541 is created at the large diameter end of the chamber. This annulus creates a localized area of increased radial depth, but of small volume, for the RBCs prior to their entry into the RBC passages 217, 317, 417. This increase in depth reduces the tendency for the platelets and other desired factors from exiting with the RBCs being discharged through the RBC port 228, 328, 428 under influence of the exit vortex created locally close to the same ports (not shown).

In all the embodiments discussed the accuracy of the RBC port closure point can be improved by employing a separation aid, such as a flowable separator gel of an intermediate specific gravity between the red blood cells and the platelets. The separator gel spreads over the red blood cell layer moving the other layers further towards the center axis. The separator gel automatically caps the first port when all of the red blood cells have exited. The separator gel viscosity is designed so that it will not pass through the small exit port at the centrifuge speed employed in the BSC. The automatic shut off of the first port can also be accomplished with a separation aid in the form of a solid material of intermediate specific gravity that is designed to enter and close off the port when the red blood cells have fully exited. An example would be plastic beads such as microspheres with the desired intermediate specific gravity that are large enough to cap the port when agglomerated as they flow toward the port.

For the bladder and air core embodiments the visualization of the RBC plasma axial boundaries can be improved by incorporating back lighting, such as in the form of an LED mounted inside the BSV adjacent to the motor centerline. Additional windings in the motor could provide the low power needed to power the lamp.

With adjustments to size and locations of the port and passage dimensions, the subject invention also has the capability for separating and concentrating a wide variety of therapeutically beneficial cells and other biological constituents. Many of these biological constituents have the potential for regenerative therapy and can be characterized as regenerative agents. These regenerative agents can assist with the regeneration, restoration, or repair of a structure or assist with the function of an organ, tissue or physiologic unit or system to provide a therapeutic benefit to a living being. Examples of regenerative agents include for example: stem cells, fat cells, progenitor cells, bone marrow, synovial fluid, blood, endothelial cells, macrophages, fibroblasts, pericytes, smooth muscle cells, uni-potent and multi-potent progenitor and precursor cells, lymphocytes, etc. The invention also has the potential to process soft or liquid tissues or tissue components or tissue mixtures including but not limited to adipose tissue, skin, muscle, etc. to provide a therapeutic regenerative agent. The resulting separated or concentrated products from the various embodiments described herein may be used as is known in the art. Medical treatment procedures may call for the concentrated product to be applied directly to a treatment site, or incorporated into a treatment device (e.g., administered to an absorbent implant material prior to, concurrent with, or post-implantation), or even combined with another material as a method of treatment, for example, by combining with a particulate material to form a paste (e.g., combined with a extracellular matrix that has been formulated as a powder).

The blood centrifuge container may also incorporate an adjustable port, e.g. a tube with an open end extending radially into the BSC and hinged at the outer periphery in such a manner that the tube can be swung in an arc for the open end to scan a range of radii (not shown). The location of the open end of the tube can be adjusted before or during operation such that it is located at a desired position with respect to the axis of rotation. For example, the entrance port could be located towards the periphery of the centrifuge container to initially vent undesired cells, and later adjusted towards the center of the container to vent platelet poor plasma. Alternatively, if the plasma fraction is what is desired to be removed, the port can be positioned so that essentially only plasma is tapped from the stratified mixture.

The apparatus may also be configured to shut off, or at least to cease rotating, once a predetermined quantity of one or more constituents such as plasma has been tapped. Specifically, a port may be positioned such that, upon stratification, the plasma constituent is adjacent the port. When the valve for that port is opened, plasma is dispatched out through the port. The port may also be configured with a sensor that senses the presence or absence of plasma. As such, the apparatus can be configured such that the barrel continues to rotate as long as plasma is sensed at or in the port, but when plasma is no longer sensed, the sensor provides a signal to the motor to stop (thereby stopping the rotation of the barrel) or signaling the opening of a tap. As plasma continues to be removed from the barrel through the port, eventually the supply of plasma at the radius of the port is exhausted, thereby causing a signal to be sent from said sensor, and the barrel stops rotating. Of course, each of these signals may arise from the sensing of any stratified layer, not just plasma.

It may be desirable to collect one or more of the discarded fractions of the liquid specimen in addition to the concentrated fraction. This can be accomplished by one of several methods. A collection bag or chamber can be connected to an exit port on the sleeve. This bag or chamber will rotate with the barrel so provisions must be taken to balance it around the axis of rotation. Another method would be to have a circumferential funnel opposite the desired exit port that would collect the fraction being discharged and guide the fluid to a collection point by gravity flow. This is further illustrated later in reference to FIG. 25.

Further embodiments are shown in FIGS. 19 through 26. These figures describe a device using the air core principle covered in FIGS. 12 through 17 but incorporating improvements designed to maximize the enrichment obtainable when preparing PRP. FIG. 19 shows the two major components of a centrifuge designed to be used in two components, a reusable drive unit 601 and a disposable portion 600. The separation of the centrifuge into two components allows the disposable component to be more cost effective.

FIG. 20a is a schematic representing a half mirror section of a revolving chamber defined by the boundary letters 'defg'. Significant dimensions are noted by length references L1 through L8, and the radii identified as D1 through D8. As can be seen in FIG. 20a, D1 corresponds to the length of the radius measured from the rotational axis XX to the outer end of the channel 640, as shown in this embodiment having an optional plenum at the end of the channel, where exiting RBCs 641 enter into the RBC passage 639. Similarly, D2 and D3 identify the inner diameters for the right and left sides, respectively, of the plenum at the end of the channel 640 farthest from axis XX. D4 and D7 mark the outer and inner diameters, respectively, of the flat located on the right hand end of wedge 609. D5 identifies the diameter at the interface between the red blood cells 641 and the buffy coat 642. D6 identifies the diameter at the interface between the buffy coat 642 and the plasma 643. D8 identifies the inner diameter of plasma passage 610, and corresponds to the interface of the plasma 643 interface with the air core 646. The length measurements L1 through L8 are based upon a distance measured from the reference line corresponding to the right side of the plasma passage 610. L1 and L2 are measured to the left and right hand sides, respectively, of the plenum at the end of the channel 640. L3 identifies the length to the flat on the right hand side of a wedge 609 (to be described later), measured from the reference line. L4 and L5 identify the location of left and right markers 644. L6 corresponds to the length to the edge of the rotation chamber measured at the diameter corresponding to the buffy coat/plasma interface D6. L7 corresponds to the length to the edge of the rotation chamber measured at the diameter corresponding to the inner diameter of the flat located on the right hand edge of wedge 609. L8 corresponds to the length to the edge of the rotation chamber measured at the diameter corresponding to the inner diameter of the entry into the plasma passage 610.

The rotational axis XX passes through boundary 'dg'. The major cross hatched area represents the tapered chamber with the outer wall having a half angle 'a'. Inserted into the conical recess of the chamber is the wedge 609 having an external frusto-conical portion of half angle 'b' that defines RBC channel 640 and an internal reverse frusto-conical recess defining half angle 'c' that defines the boundary of the plasma 643. It should be noted that half angle 'b' need not necessarily be the same as half angle 'a', in other words the channel 640 may be tapered, not parallel.

As fluid exits the RBC outlet port, the fluid exiting through the RBC passage 639 experiences high shear forces, and the RBC channel 640 serves to ensure that the RBC passage 639 entry port is at the end of the channel 640 and at a distance removed from the RBC-BC interface, with the channel dimensioned to allow for significantly slower local flow speeds at the RBC's entrance into the channel 640, relative to the high exit speed the RBC experiences as it exits through the RBC passage 639.

For example, in one embodiment, RBCs collect at the outer edge of the spinning chamber and discharge through one or more RBC passages 639 fed from a circumferential groove or plenum, which, in turn, is fed from a thin circumferential channel 640, or alternatively, circumferential sections forming multiple channels 640, starting adjacent to the buffy-coat collection areas. The circumferential channel 640 has a circumference many times larger than the radial depth of the channel. For a device providing a 60 Ml centrifuge, and having a channel with a 4.5 inch circumference by 0.020 radial depth the orifice diameter for RBC passage 639 would be of the order 0.010 inch. This combination spinning at approximately 17000 RPM would result in velocities of 2000-3000 cm/sec from the orifice at RBC passage 639, and only 1.5 cm/sec along the channel 640. Thus the channel 640 slows the flow adjacent the separation layer by a factor of over 1000 to 1. In another embodiment (not shown) not having a plenum, the RBC passages may be fed directly from the thin circumferential channel, starting adjacent to the buffy-coat collection area. Similar performance, in achieving a reduction of flow rate at the separation layer, when compared to the orifice exit, would be expected as that described with reference to the embodiment having a plenum.

It has been observed that there may be a benefit in evacuating the RBCs under a reduced rotational speed of the spinning chamber. This reduction of rotational speed must be accomplished in a manner that does not disrupt the stratification of the separated constituents, further; the reduced rotational speed must not be reduced to the point of allowing significant degradation of the established stratification of the constituents. For example, upon achieving satisfactory stratification through the operation of the device at a first speed suitable for separation, a gradual ramping down of the rotation speed will maintain the stratification, and once arriving at a second rotational speed, the RBC cells may then be ejected through the RBC passage 639, at a correspondingly reduced velocity as a consequence of the lower forces created through the reduced rotational speed of the spinning chamber. For the example previously described, having a rotational speed of approximately 17000 RPM for separation, the gradual reduction may occur in a controlled fashion over a determined period of time, until settling at a targeted lower rate of rotation, in this new example rotating at approximately 13000 RPM, in order to allow evacuation of the RBCs while still preserving the integrity of the RBC/BC interface. It is also recognized that minor adjustments to the timing of these steps may, for practical purposes, may achieve similar results, such as opening of the RBC valving while the speed is still ramping down, but close to the targeted evacuation rate.

Modifications to the dimensions, or rotational speeds may be employed to ensure that a reduction in localized flow rates, when measured at the RBC passage 639 and compared to the RBC entry into the channel 640, may be made to achieve different reduction rates, such as reduced beyond approximately 500:1, or 100:1, instead of the 1000:1 described above. As can be seen in the embodiment of FIG. 20a, the channel 640 is arranged on a radially shallow angle a, and is shown having a plenum at the terminus of the channel, from which the RBC passage 639 provides for the discharge of the RBC. In another embodiment (not shown), the device may not provide a plenum at the terminus of the channel, but rather the channel terminus may include the outlet for the RBC passage, or the channel may reduce in dimension (taper) and funnel directly into the outlet for the RBC passage. As described above, the devices of this invention aim to reduce the effect of the exiting RBCs upon the buffy coat components, as may be accomplished by providing for spatial separation between the RBC outlet and the RBC/buffy coat interface. It is this spatial separation, with or without a plenum in the channel, that reduces the tendency for the platelets and other desired factors from exiting with the RBCs being discharged through the RBC passage 639 under influence of the exit vortex created locally close to the port. By operating the device in a manner that prevents plasma or buffy coat components from entering the channel 640, the high shear forces will be limited in effect only to the RBC component, and will be unable to disrupt the interface between the RBC and the BC. Typically, when comparing the concentrated blood product with the starting material, about 93% of the RBC's are removed using the chamber as described above, and as depicted in FIG. 20a. It may be desirable in some instances to remove an even greater proportion of the RBC's. Values of approximately 98% removal have been achieved by further managing the turbulent flow towards and directly above RBC passage 639. The management of the turbulent flow above and adjacent to the RBC passage may be achieved in some embodiments by, at least partially restricting or even completely closing off the flow into the circumferential channel (in a direction of flow that is generally from the flat of the wedge, towards the plenum, if any), without preventing the flow of fluid through the channel (in a direction that is largely perpendicular to, and circumferential around, the axis of rotation) towards the RBC passage. This restriction may be created over some portion of the circle that is the circumferential channel. For example, in an embodiment, the width of channel 640, at least the portion closest to the RBC passage, can be at least partially reduced, for example, in one embodiment, from at least 1% to 100%, in another embodiment from at least 10% to 100%, or in yet another embodiment, from at least 20% to 100%, and in still another embodiment, from 50% to 100% reduction, over a portion of the circumferential channel, for example, in an embodiment from about 10 degrees to about 350 degrees, or, in another embodiment from about 15 degrees to about 270 degrees, or, in still another embodiment, from about 20 to 180 degrees of the circumference, with the angular center optionally being substantially aligned with the location of the RBC passage 639. FIG. 33 depicts a restrictive feature 800 that restricts the flow of fluid into the channel 640, and as shown in FIG. 33a, is in the portion of the channel encompassed by angle d (here depicted as 90 degrees) of the circumference. The restrictive feature may be integrated as part of the rotating chamber, such as by machining or molding of the rotation chamber, or alternatively may be manufactured as a separate component and later affixed in some manner known to those skilled in the art, to either the wedge 609 surface (as shown in FIG. 33), or alternatively, to the interior surface of the rotating chamber (not shown). The restriction may be of uniform dimensions, as shown in FIG. 33a, or alternatively, in an embodiment (not shown) there may be provided a variable reduction in the channel 640, where the greatest restriction of the entrance into the channel is at the portion of the channel that is aligned with the RBC passage, and the restriction percentage is reduced in a gradual or steep taper, or even a stepped manner, as the distance of the channel increases from the RBC passage. For this embodiment, the goal is to provide the appropriate percentage restriction tailored to counteract the variability of the flow rate into the channel arising from the variable proximity to the RBC passage; thus in the regions of the channel closest to the RBC passage, the percentage of restriction to the channel will be maximized, while away from the RBC passage, the percentage of the restriction of the channel will be appropriately reduced, thus by ensuring uniform flow rates into the channel, the disturbance to the interface between the separated layers (e.g., RBC/BC interface) is minimized. In these, and any other embodiment of the centrifuge devices described herein, it is recognized that by using materials in the construction of this part of the chamber that are similar in density to blood, a condition of imbalance for the rotating chamber is avoided, or alternatively the rotating chamber may be balanced using counter weights, properly placed, as known to those skilled in the art.

Similarly, by placing the plasma passage 610 at a location removed from the buffy coat component (and optionally located within a plenum as depicted in FIG. 27a), and with the buffy coat-plasma interface not extending inward beyond D7, the buffy coat can be contained within the chamber, as with the shallow angle c, the high shear forces at the plasma passage 610 will not cause the disruption of the BC-plasma interface. Thus there is a reduction in the tendency for the platelets and other desired factors from exiting with the plasma discharged through the plasma passage 610 under influence of the exit vortex created locally close to the port. Though depicted in FIG. 20a as located at the base of the wedge 609, the plasma passage may be located elsewhere, so long as the opening is at a suitable radius that is smaller than the radius of the buffy coat-plasma interface, such as at a location corresponding to L8 in FIG. 20a. Through these features, the embodiments described aid in preserving substantially all of the buffy coat component within the chamber and enhancing concentration or enrichment efficiency of the finished product.

Furthermore, with reference to FIG. 27a, there is depicted an embodiment identical to that shown in FIG. 20a, except that there is included a plasma plenum 655 in the form of circumferential groove (or portions of a circumferential groove) housing the orifice(s) that lead into the plasma passage 610. In this embodiment, the exiting plasma will flow along the tapered channel defined by the boundaries of the wedge 609, and the air core interface with the plasma. While the chamber is being rotated, and the plasma valve open, the plasma will flow towards the plasma passages (depicted here located at the base of the wedge 609), and spill over the wedge base and into a plasma plenum 655. Once within the plasma plenum, the plasma will flow along the length of the plenum (i.e. circumferentially) until it encounters and exits through the orifice(s) leading to the plasma passage 610. While the plasma is traveling within the plenum 655, it will not exert shear forces upon the plasma/buffy coat interface, which is at a distance removed, and physically shielded by the presence of the wedge 609.

Comparing the FIGS. 20b and 27b will allow visualization of the direction of fluid flow as the plasma approaches the plasma outlet, whether as a continuous slope (the geometry shown in FIG. 20b), or with a plenum 655 (the geometry shown in FIG. 27b). These figures represent a projection view, looking down towards the opening to the plasma passage 610, as if one is looking from the axis of rotation towards the outside diameter of the chamber.

With reference to FIG. 20b, the plasma is depicted as traveling from right to left, and as the fluid approaches the left edge of the chamber, the fluid will be drawn towards the outlets for plasma passage 610. In this embodiment not having a plasma plenum, the shear forces will be proportionally reduced with increasing distance from the opening, thus as the plasma travels along the inside face of the wedge (along angle c), the shear forces will not necessarily be uniform throughout the entire diameter of the region, but will be higher when alongside the locations of the openings to the plasma passage 610. While the geometry of FIG. 20a has been empirically determined to be effective in minimizing shear forces affecting the buffy coat/plasma interface, it may be possible to even further reduce the shear forces experienced at the flat of the wedge during the operation of the device.

With reference to FIG. 27b, the plasma is depicted as traveling from right to left, and enters into the plasma plenum 655, prior to flowing along the plenum towards the openings 610. As can be seen by the uniform arrows (right side) depicting fluid flow towards the plenum 655, the presence of the plenum is expected to reduce variations in shear force, when measured circumferentially within the plasma channel (the plasma flowing between the wedge face at angle c and the air core), as the plasma will approach the base of the wedge 609, and flow into the plasma plenum 655, and thus create an effect similar to water flowing over the breast of a dam. That is, prior to cresting the obstruction, whether upstream of the dam, or prior to entering the plenum, the fluids flow slowly and smoothly, then once past the obstruction, whether downstream of the dam or within the plenum, the fluid flow rates will be relatively much higher and less uniform. As can be seen by the arrows depicting the fluid flow pattern, the flow of plasma towards the plasma plenum is expected to be uniformly distributed over the entire diameter, then once the plasma has crested the wedge, and is within the plenum 655, then there will be large variations in fluid movement as the plasma flows out the one or more openings to the plasma passage 610. Since the variable direction shear forces are largely contained within the plenum, and not affecting plasma flowing along the wedge face, this embodiment would be expected to allow for enhanced enrichment factors of the buffy coat components. The geometry of this embodiment allows for retained plasma, measured as the depth between D8 and D6, to be minimized, due to the reduced variability of plasma flow rates, when measured circumferentially along the plasma channel, which would otherwise tend to disrupt the buffy coat/plasma interface.

Furthermore, with reference to FIG. 20a, it should be pointed out that the volume of plasma remaining after all the discharged plasma has left the chamber is defined by the boundary diameters D8 and D6. This volume can be tuned to get the value of enrichment desired by adjusting these same mentioned dimensions.

It should also be made clear that to obtain high degrees of enrichment, the depth of plasma beneath the buffy-coat (as seen in FIG. 20a) must decrease (diameter dimension (D6–D8)/2 decreases) so the risk of platelet loss increases because the out-flowing plasma shears the buffy/plasma interface more closely. However, the pressure driving the plasma outflow gradually drops to zero as the plasma diameter approaches D8 since pressure driving the plasma flow is proportional to the square of the speed of rotation, multiplied by the difference of the squares of the radius of the opening of the plasma passage located at D8 and the radius of the plasma/air interface within the chamber.

By taking advantage of this steadily reducing flow effect as the plasma approaches D8, the plasma depth (D8–D6) can be minimized, with little loss of buffy coat due to shear, and the residual plasma volume minimized and the enrichment maximized.

To summarize, RBC/buffy-coat shear is minimized using the outer diameter channel to control RBC/buffy-coat shear, and plasma/buffy coat shear is controlled by geometry and the reducing plasma to air core driving pressure.

Thus, while the chamber is rotating, and prior to the discharge of any of the plasma, there is a larger pressure head driving the plasma out through the plasma outlet and into plasma passage 610, subsequently, as the volume of plasma in the chamber decreases, the pressure head above the plasma outlet is reduced in a proportionate amount, until the plasma level reaches the level of the plasma outlet at D8, and all plasma flow out through the plasma passage 610 terminates. As the flow rate through the plasma passage 610 is reduced as the plasma volume is reduced, this provides the added benefit that the tendency for shear forces to affect the buffy coat is minimized, as at the point the plasma flowing out and the buffy coat are at nearest proximity to each other (i.e., the distance between D6 and D8 is at its minimum), the plasma evacuation flow rate will be at its lowest rate.

In operation blood fills the chamber and after a period of time at speed separates in to red blood cells (RBC), buffy coat and plasma. After separation, RBC passage 639 is opened and RBCs discharge from RBC passage 639, the interface of the RBC's being evident at L5 at the transparent conical surface. Visible markers are placed on the chamber at L5 and L4 to guide an operator in the closing of RBC passage 639: when the RBC interface reaches somewhere between L5 and L4 the discharge of RBC's out of RBC passage 639 is stopped by manipulation of valves to be described later. At this point, residual RBCs occupy a predefined volume defined by the conical channel 640 and the circumferential recess at the left hand end of the RBC channel 639. When collecting buffy coat (BC) 642, defined on the illustration by the honeycomb hatch, it is important to prevent the BC from migrating into the RBC channel 640, since the BC cannot be recovered at the end of the procedure if they migrate there. To ensure that this does not happen, the rate at which the RBC interface appears to move along the conical surface of the chamber is controlled to a velocity that is sufficiently low for an operator to stop the process (by closing RBC passage 639) as the interface travels between makers placed at L5 and L4. This velocity is a function of speed of rotation, diameter of the chamber, size of the RBC discharge port connected to passage 639, and the half angle 'a' of the chamber. These variables are adjusted to give an interface velocity at L5 or L4 that is manageable by a human operator but that does not impede the rapid separation required (whole process of separation, discharge of unwanted RBCs and plasma in less than 2 minutes). In testing various parameters, it has been experimentally determined that an interface velocity of approximately 4 mm/sec allows accurate intervention by the operator, though it is recognized that higher and lower velocities may be desirable, on the range of less than 10 mm/sec. (In the case where the RBC to Buffy coat interface is detected by optical sensors or the like the approach velocity of the interface can exceed the 10 mm/sec. rate). When RBC port 638 is initially opened, there is a potential for temporary turbulence due to the sudden pressure drop that may cause some disruption of the clarity of the interface between the RBC and BC, at D6. The effect of this turbulence can be minimized by an automatic ramp down in the centrifuge speed that is controlled by the software in the base unit 601. Changes in centrifugation speed can be programmed in the software to automatically initiate by timers in the software or signals generated by movement of the valve mechanisms. When the RBC discharge is stopped, the BC is captured at the end of the flat or separation surface on the right hand end of the wedge 609, defined by diameters D4 and D7. Though the separation surface is depicted in FIG. 20*a* as being at 90 degrees to the axis of rotation, it is envisioned that the separation surface may be at another angle relative to the axis of rotation. The separation surface forms the "top" surface of the wedge 609 when the centrifuge is in its normal upright orientation. If the RBCs are stopped at L5, the BC outer diameter is D5, if the RBCs are stopped at L4 the BC outer diameter is at D4. The buffy coat (BC) volume is around 0.5% of the blood volume initially introduced, so the flat on the end of the wedge (D4, D7) can be defined to ensure that in the worst case (RBC stopped at L5) the BC stays on the separation surface and does not extend into the inner half angle cone 'c'. Once the RBC passage 639 is closed, the plasma passage 610 is opened and plasma flows to discharge. The illustration shows the situation when all the plasma has flowed out of plasma passage 610 and flow has stopped because the air core 646 has expanded to the diameter of the passage inlet at D8. Prevention of BC getting into the inner cone is important since the axial velocity of the plasma surface accelerates as it approaches the exit passage 610 and fast shear velocity at the BC/Plasma interface results in loss of platelets into the plasma. With radial separation of BC to air core (D6–D8)/2 of the order 1 mm-2 mm, the loss of platelets into plasma is acceptable and enrichment factors (EF) of 8:1 or more can be consistently obtained. Enrichment factors are defined by the following equation: (EF=(# of platelets captured in the BC sample per unit volume)/(# of platelets in the original whole blood sample per unit volume)). Fundamentally, this design has been conceived to minimize the shear at the RBC/BC and BC/Plasma interfaces and hence reduce loss of BC to the RBC discharge or the plasma discharge.

In one embodiment, the orientation of the device in use is with the axis of rotation XX being vertical, with the port valve 602 at the top of the device. As a consequence of the geometry of the rotating chamber, when the rotation is halted, any fluid (e.g., RBC) that is within the channel 640, will tend to remain contained in that channel, and substantially all other fluid above the line corresponding to the flat 608 of the wedge 609 while in operation (i.e., to the right of L3 in FIG. 20*a*), will flow by gravity, upon cessation of rotation, and pool directly underneath the port valve 602, and is available to be harvested, such as by being drawn into a needle directed through the port valve and into the pool of concentrated materials. It is recognized that the various embodiments described herein may be operated at another angle (e.g., horizontal), and then optionally rotated to vertical for harvesting, after cessation of rotation. By maintaining the RBCs sequestered within the channel 640 upon cessation of rotation of the chamber, the concentration of the buffy coat components can be maximized, as those materials within the channel (e.g., RBCs) are not available to further dilute the concentrated buffy coat or other blood components. In some embodiments, it may be advantageous to add a surface tension modifying coating (e.g., hydrophilic or hydrophobic coating) to at least a portion of the rotating chamber, such as the flat 608 at the end of the wedge 609 to prevent some of the captured BC from remaining on the flat due to surface tension. Furthermore, there may be a benefit in providing an angle (e.g., 1 to 45 degrees) to the flat of the wedge, in order to direct the flow of fluid towards the central collection area, if in a generally vertical orientation.

It has been observed that causing the rotation chamber to decelerate rapidly, or alternatively abruptly, or with an uneven rate of decrease, will lead to an increase in the amount of platelets in the collection area, relative to a more gradual deceleration of the rotation chamber. It is believed the rapid deceleration, such as may be accomplished by incorporating a braking system into the device, will create mixing of the components above the flat of the wedge, and avoids the occurrence of residual concentrated buffy coat components remaining on the surface of the flat of the wedge. It is believed that the red blood cells remaining within the chamber and within the channel, will remain largely contained within the channel, and not mix with the buffy coat, even upon rapid deceleration. Alternatively, one may simply physically dislodge platelets, such as by tapping, shaking, jarring, or otherwise disturbing any components that, due to surface tension, had remained away from the collection area, such that they can now be collected.

The geometry of the embodiments of the device incorporating the wedge 609 provides at least 3 benefits aiding in the efficiency, and operation of the device, as the wedge 609 serves to: 1) create spatial separation; 2) form the channel; and 3) increase the apparent depth of liquids. First, the wedge creates spatial separation between the outlets for the plasma and the RBC, and therefore can minimize the effects of shear forces at the outlet from affecting the buffy coat components which remain distant alongside the flat of the wedge. Second, the wedge partially forms the channel, as the outermost surface of the wedge, at angle b, provides part of the inner boundary of the channel 640. Third, the wedge enhances the ease of operating the device, as it enhances the apparent depth of the liquids displaced by the existence of the wedge. That is, the wedge serves to displace the volume of the fluids that are in the wedge region (between D2 and D8), and has the effect of increasing the apparent depth of these liquids, as dimensions between D4 and D5 are increased due to the displacement, and necessarily the spacing between markers 644, at L4 and L5, can accordingly be made larger and provide greater resolution for the operator. With the effect that the operator can now more accurately determine when to halt the discharge of the RBC through the RBC passage 639.

FIG. 21 shows the device of FIG. 19 assembled and in the running state with the RBC port 638 open, the plasma port 612 closed, and the RBC discharged to the RBC-Plasma receiver 647. No plasma 643 has yet been discharged to the receiving chamber. The air core 646 is fully established and the separated fluid components are established with clear boundaries. The spinning centrifuge blood-containing chamber is made up from two elements, the tapered barrel 606 and the end cap 614. This chamber spins in two bearings 619 and 604, the smaller bearing 604 locating the narrow end of the chamber, and the larger bearing 619 locating the larger end of the chamber indirectly via the drive shaft 617 and the valve cap 616. The smaller bearing 604 is mounted in the transparent mid cover 607 and the larger bearing in follower 618. Valve cap 616 rotates with the chamber components driven by a key or pin (not shown) from the end cap 614, and can translate axially along the rotation axis propelled axially by the follower 618, which in turn is moved axially by cam followers 620 and cams 621. Axial movement of valve cap 616 controls the position of RBC port 638 and plasma port 612, and thus controls the discharge of RBCs from RBC passage 639 or plasma from plasma passage 610. Cams 621 (typically 3 in number but may be more or less than 3) are integral with drum 613. Follower 618 can move axially within drum 613 but is prevented from rotation by male keys 631 on the follower and female keys on substructure 624. By rotating drum 613 the operator moves follower 620 axially and thus controls the position of the RBC and plasma ports 638 and 612. RBC-plasma receiver 647 surrounds the rotating elements to capture the discharged RBCs and excess plasma and moves axially with the valve cap 616.

Clearance between shaft 617 and valve cap 616, and the clearance between valve cap 616 and end cap 614 affects the fit and concentricity between end cap 614 and valve cap 616. 'O'-rings 648 and 611 act as seals and/or act as suspensions between these two caps. If the clearances are held very small the 'O'-rings act only as seals, but if the clearance is increased substantially the 'O'-rings do double duty as seals and as suspensions. Such suspension characteristics can be selected so that the natural frequency of the valve cap 616 oscillating on the chamber assembly (shaft 617, end cap 614, and barrel 606) is substantially lower or substantially higher than the operating speed.

Centrifuge coupling 633 attached to drive shaft 617 accepts torsional drive from motor 626 via motor coupling 629. Motor 626 is mounted on substructure 624 that is fastened firmly to base enclosure 625. An operator activated latch 622 ensures that disposable portion 600 is firmly located relative to reusable portion 601 by engaging in an annulus integral with drum 613.

Disposable portion 600 arrives as a sterile unit and is used adjacent to a sterile field in an operatory environment. On completion of the procedure for preparing and applying PRP or PPP (which could involve running the device multiple times for multiple applications for a single patient) disposable portion 600 is discarded into the bio waste stream. However the reusable portion 601 remains in the operatory and may get moved elsewhere for storage. To ensure that no whole blood or blood components contaminate the reusable portion 601, a variety of elements may be employed to prevent the egress of these fluids. With reference to FIG. 26, absorbable washers 632 and 636 can capture any spillage from receiver 647, and gel accelerator 649 can cause the discharged fluids in receiver 647 to gel into a non-flowing gelatinous mass. Alternatively sealed bearings (not shown) at 619 and rolling diaphragms (not shown) between drum 613 and follower 618 can capture all liquids. Absorbable materials can be made from porous polyethylene (as sold under the tradename 'Porex'), superabsorbent polymers, polyacrylates, polyelectrolytes, hydrogels, chalk, cellulose fibers or sponges, or woven textile, or other suitable materials known in the art. Gel accelerators can be made from materials as supplied by Multisorb Technologies, Inc. under the name Drimop®. Residuals of the PRP collected in the chamber are contained by port valve 602. Combinations of these solutions to leakage will also be clear to those skilled in the art.

FIGS. 28-31 depict a radial indexing valve receiver 700, which is an alternate embodiment of the previously discussed RBC-plasma receiver 647. This radial indexing valve receiver incorporates a radial indexing valve that works in cooperation with the rotating drum 613 and follower 618 (as shown previously in FIG. 21) in order to prevent the contents from spilling from the receiver. The radial indexing valve receiver 700 consists of two mating components, the upper valve 701 and the lower storage chamber 702. The upper valve 701 preferably includes four slots 704 and the lower storage chamber 702 includes four slots 705. The number of slots can be varied and typically the numbers of slots in each component are the same. The upper valve 701 includes indexing tabs 703 that cooperate with grooves (not shown) in drum 613 so that the upper valve 701 rotates when drum 613 is rotated. The upper valve 701 also includes a 360 degree liquid inlet window 707. The lower storage chamber 702 includes grooves 706 on its inner circumference that cooperate with tabs (not shown) on follower 618. Grooves 706 serve to key the lower storage chamber 702 to the follower 618 and prevents the lower storage chamber 702 from rotating when drum 613 is rotated. With reference to FIG. 30, the upper valve 701 and lower storage chamber 702 include annular interlocking features 709 and 708. As can be seen in greater detail in the disassembled depiction of FIG. 31, the interlocking features include the slots 704, 705 and mating surfaces 710, 711. As can be seen in FIG. 30, the interlocking features 709, 708 define an interference fit so that upper valve 701 and lower storage chamber 702 can be snapped together where mating surfaces 710 and 711 create a water tight seal. In use, the receiver 700 is to be supplied in the position as shown in FIG. 28 where the slots 704 in the upper valve 701 do not overlap with slots 705 in the storage chamber 702. The centrifuge chamber 646 is then to be filled with blood and the centrifuge is activated. When drum 613 is rotated to open RBC valve port 638 (as previously discussed with reference to FIG. 21), the upper valve 701 rotates with the drum, thus at least partially overlapping slots 704 and 705 and thereby creating a passage between the two receiver components 701 and 702, and as seen in FIG. 29. The expelled RBC's 641 enter the upper valve 701 through 360 degree liquid inlet window 707 and drain by gravity into lower storage chamber 702, through the overlapping region of the slots. When drum 613 is rotated back to its home position to stop the flow of RBC's 641 from valve port 638, slots 704 and 705 return to the non-overlapping position shown in FIG. 28 thus sealing the RBC's in the lower storage chamber 702. Similarly, when drum 613 is rotated in the opposite direction to open the plasma port 612 the opposite sides of slots 704 and 705 are caused to overlap, thus allowing the ejected plasma 643 to drain into the lower storage chamber 702 through the overlapping slots. Drum 613 is then rotated back to its home position at the end of the process to return slots 704 and 705 to the non-overlapping position, thus sealing the discarded fluid in the lower storage chamber 702. This prevents any spillage of the fluid during subsequent handling and disposal of the disposable portion 600.

Typical dimensioning of slots 704 and 705 is such that there will be overlap when the upper valve 701 is rotated in either direction. In a preferred embodiment, the upper valve slots 704 each encompass 30 degrees of the circumference while the lower storage chamber slots 705 encompass 50 degrees of the circumference. This dimensioning leaves 5 degrees between the edges of the slots, when in the closed orientation. Drum 613 is to be rotated approximately 35 degrees to open ports in valve cap 616. This will cause an overlap of slots 704 and 705 of 30 degrees, or put another way, each entire slot 704 of the upper valve 701 will be totally open to the lower storage chamber 702 through slot 705. Other combinations of slot geometry and placement are possible and would be obvious to one skilled in the art. The upper valve 701 and storage chamber 702 are typically blow molded components, using resilient thermoplastic resins, including but not limited to, polypropylene and polyethylene.

Reusable portion 601 is powered by a cord mounted transformer (not shown) from an AC supply, or from a DC power pack such as those used for cordless drills and the like. Additional items not shown are (but not limited to) a simple display mounted on the base enclosure 625 that indicates power on-off to the centrifuge, elapsed time from power on, and may include items such an audible alarm for warning the operator when elapsed times reach certain levels. In addition hall-effect switches or reed switches (not shown) mounted in the base 625 which respond to magnets mounted in the disposable portion 600 can be used to indicate the rotation of drum 613 in base enclosure 625, and-or can be used to select varying motor speeds that might be necessary for optimum separation of fluid components.

Instead of an operator revolving drum 613 manually, actuators (e.g. motor-gearbox combinations or screw jacks) in the base 625 can rotate the drum automatically in response to signals from the switches described above and-or from a small solid state computer employed to optimize operation.

FIG. 22 is a simplified transverse section of FIG. 21 at AA. The blood has separated into its major components plasma 643, RBCs 641, and Buffy-coat (BC) at 642.

FIG. 23 is a simplified transverse section through BB of FIG. 21. This section shows the construction of the plasma valve consisting of passage 610, and 'O' ring 611. The construction of these outlet ports is similar to that shown in FIG. 3b. When this valve is opened, port 612 will be moved to a position in alignment with passage 610, to allow for the flow of fluid therethrough.

FIG. 24 shows the device of FIG. 21 running in the situation where the RBC valve port 638 is closed, the plasma port 612 is open, and the plasma discharge has been completed. The volume of plasma 643 is the final volume.

When platelet poor plasma (PPP) is required for a procedure a slightly different configuration is required for the PPP receiver. FIG. 25 has most components similar to those shown in FIG. 21 but there are two receivers, one for RBCs 637 and one for PPP 635. Since two fluid components are captured by discharge from the spinning chamber the receivers both have to be fixed axially relative to drum 613 to accept the different axial locations of the plasma port 612 and RBC port 638 as they discharge appropriate fluid component. A plasma access port 645 spans the walls of the receiver 635 and extends through slot or opening (not shown) in drum 613. This port is of elastomeric material such as nitrile rubber that permits the passage of a hypodermic needle for the removal of the PPP.

In use the operator places a sterile disposable portion 600 into the reusable portion 601, the drum position being preset at the factory to the position where both plasma port 612 and RBC port 638 are closed. The operator then fills a syringe with whole blood from the patient and introduces the blood via the syringe through port valve 602 into the centrifuge chamber until the chamber is filled. The device is activated and the motor runs for about one minute by which time the blood has separated into the primary layers of RBC, buffy-coat, and plasma. At this time the drum is turned to position the RBC valve to the open position whereupon RBCs start to discharge into receiver 637. As the RBCs discharge the interface between RBCs and buffy coat (D5 in FIG. 20a) approaches markings on the rotating barrel at 644 (L5 and L4 of FIG. 20a). When the interface is between marks at 644 (about 30 seconds after the RBC port 638 is opened) the drum is turned to close the RBC port and open the plasma port 612. Plasma then discharges into the receiver and continues to do so until the air core limits further discharge. At this point (about 30 seconds after the plasma port was opened) the motor is stopped and the enriched residual sample in the chamber is removed via port 602 with a syringe and cannula for injection into the patient (or onto material about to be used as an implant). In the case of a PPP preparation the process is the same as that described for PRP except that the device conforms to the device shown in FIG. 25 and the PPP is extracted from the side elastomeric port 645 of FIG. 25.

It is recognized that by employing varying speeds of centrifugation, and altering the diameters at which the outlets from the chamber are placed, it is possible to concentrate different components, or isolate different specific gravity fractions of the fluid material within the rotation chamber. For example, rotating at a slower speed, as known to those skilled in the art, and removing the bulk of the RBCs as described above, will provide a plasma material with the suspended platelets. When rotated at lower speeds, the platelets will not differentiate by specific gravity from the plasma. Upon increasing the speed of rotation, the platelets will then tend to differentiate by specific gravity from the plasma, allowing flexibility in achieving the desired combination of blood products sought by the operator.

While the various embodiments discussed previously have described the blood separation chamber having a circular cross section, it is recognized that any shape capable of high speed rotation can be utilized, so long as there is an angled or tapered inner diameter to facilitate the appropriate flow of the red blood cells towards the RBC passage. For example, a separation chamber that provides an ovalized cross section may be employed, as it will be properly balanced and suitable for the rotational speeds required. Similarly, other separation chambers having cross-sectional profiles in varying shapes (e.g., octagonal, square, triangular, etc.) can be employed, and if necessary, balanced with weights to ensure proper balance when rotating. Furthermore, it is also recognized that multiple chambers may be utilized in the device, such as by providing 2 or more sections of a circle, or alternatively 2 or more vessels may be balanced to allow rotation of the multiple chambers, collectively forming a rotor, where each of the chambers would provide for discharge of particular blood components (e.g., RBC and Plasma), while allowing for the concentration and access to the desired blood component concentrated in each of the chambers.

The embodiments described herein are chiefly intended for use in separating components from whole blood, though they may be used with other liquids as well. In the case of blood product, once the device has been operated to stratify the blood into its constituent components, and the red blood cells and plasma removed from the blood separation chamber via the previously described RBC and plasma passages, the concentrated buffy coat containing platelets and white blood cells will remain within the chamber. In all the embodiments discussed, the operator of the device may further choose to clarify the resulting buffy coat by adding one or more additional biocompatible solutions, as a separation aid, into the device and optionally performing further centrifugation steps. These additional biocompatible solutions are sometimes referred to as focusing fluids. As previously described, the buffy coat consists of several constituents, including platelets and leukocytes (i.e. white cells), each having unique specific gravities. The leukocytes contain granulocytes and lymphoid cells such as lymphocytes and monocytes, each of these having unique specific gravities. For some applications, it may be important to isolate or remove one or several of these components from the buffy coat to provide a further purified therapeutic material. For instance, some researchers have found improved in vitro performance by removing leukocytes from the buffy coat (S. R. Mrowiec et al., A novel technique for preparing improved buffy coat platelet concentrates, Blood Cells, Molecules and Diseases (1995) 21 (3) February 15: 25-23). By way of example, a fixed quantity of one or more liquids (e.g. focusing fluids) having specifically targeted specific gravities could be delivered into the blood separation chamber to allow further separation of various components of the buffy coat (e.g. leukocytes) thereby focusing in upon a very specific sub-component of the blood. Alternatively, a focusing fluid may be used to enable the removal of all of the red blood cells or plasma, by being of a targeted specific gravity between the buffy coat and either the red blood cells or the plasma components, such that by repeating the concentration process described above, a blood component free from residual traces of either the plasma or red blood cells may be achieved. Such focusing fluids could include colorant, markers or other indicators to help distinguish the boundaries between the targeted and non-targeted biologic components. Fluids such as Ficoll-Paque sodium diatrizoate solution (density of 1.077 g/mL, distributed by GE Healthcare), Percoll (density of 1.088 g/mL, distributed by GE Healthcare), and Cellotion (distributed by Zenoaq) and other fluids known in the art could be used for purifying, separating and/or concentrating a wide variety of therapeutically beneficial cells and other biological constituents.

In another embodiment the biocompatible focusing fluid may selectively bind to a blood product and subsequently be isolated or separated by centrifugation, to result in a more concentrated desired blood component. Various techniques are known in the art for accomplishing the binding, for example, solid bead components of desired specific gravity may be coated with antibodies and employed to selectively bind the focusing fluid layer with the targeted blood component (or conversely, the blood component to be separated from the desired blood component). Alternatively, various techniques and reagents known to one skilled in the art, using techniques known, for example, from separation chemistry (e.g., chromatography or absorption) may be employed (such as ion exchange resins as used in HPLC and FPLC methodologies). In these embodiments, upon adding the focusing fluid to the blood separation chamber containing the previously concentrated blood product, and allowed an opportunity to bind, the desired blood product will be caused to separate from the unwanted blood product when the rotation is employed to stratify the materials within the blood separation chamber. Removal of separated products can proceed through one or both of the outlets as described previously. The binding of the focusing fluid in this embodiment may be reversible using techniques known in the art, such that upon being harvested, the blood component may be unbound from the focusing fluid, and optionally subjected to another purification procedure to provide harvested blood product free of any focusing fluid.

As before, with an operator or sensor causing the actuation of the valve mechanism controlling the discharge of fluids from the chamber, a detectable interface would be beneficial in determining when to close outlet valves. For this reason, the focusing fluid is preferably distinguishable in some manner at the interface with the other components within the chamber, for example, by being distinguishable by color. Alternatively, prior to the centrifugation with the focusing fluid, a biocompatible, selective dye or marker material may be added to distinguish the fluids within the chamber, and create the interface that is detectable by the operator or sensor. Thus, the selective coloring would facilitate detection of an interface between the desired components, and those components sought to be removed from the blood separation chamber through one or both of the outlet ports.

In another embodiment, device 750 is configured as shown in FIG. 32 in order to directly apply a selected fraction of the blood sample to a biologically compatible scaffold 751 via the spraying action from port 752 of the spinning chamber. Examples of scaffolds include but are not limited to purified collagen pads or powder, extracellular matrix sheet or powdered products, bone void fillers and resorbable or non-resorbable synthetic meshes. In the embodiment shown in FIG. 32, the cam 621 has four positions, 1-4, with position #1 being the lowest position, instead of the three previously described with regards to earlier embodiments. Valve cap 616 has additional BC port 752 and end cap 614 has additional BC passage 755. Following the centrifugation procedure as previously described, follower 620 is rotated from the neutral position #3 to position #4 on cam 621 to align port 638 with RBC passage 639, such that the red blood cells exit from port 638 into receiver 647. At the appropriate time, follower 620 is rotated to the #2 position on cam 621 to align port 612 with passage 610, such that plasma exits from port 612 into receiver 647. In the final step, follower 620 is rotated to position #1 on cam 621 to align BC port 752 with passage 755 to allow BC to exit to a BC receiver 753. In the embodiment of FIG. 32, the BC receiver 753 contains a scaffold 751. The scaffold 751 can receive the BC as it is discharged into the BC receiver; for example, the scaffold may be directly sprayed with the BC or alternatively, the BC can wick into the material by capillary action or absorption into the scaffold 751. When the desired amount of BC has exited at port 752, the follower 620 is returned to neutral position #3 on cam 621 and the motor switched off. Scaffold 751, now treated with BC, may then be aseptically removed from receiver 753. While various access methods may be employed, one example is to provide access by disengaging mid-cover 607, at connection joint 754, to provide for scaffold access. Using analogous alterations of the design of receivers, cam and ports, it is possible to directly apply any of the blood fractions to a desired scaffold.

Direct application of BC to a scaffold results in a time savings, and less chance for contamination of the preparation, since the application is done automatically in a closed system rather than manually in an open container. It would also reduce the chances for infection of health care workers by reducing the amount of handling of a blood product that potentially contains a human pathogen.

In order to prevent premature destruction of the blood cells that are being applied to the scaffold 751 in receiver 753, the force at which the materials are ejected from the centrifugation chamber can be controlled. By example, it has been shown that in a device with a 30 ml capacity, with an exit hole diameter of 0.01", the centrifuge gave a higher proportion of intact cells when the centrifugal force (g) was reduced to below about 1000 g, with additional improvement in cell survival as speeds were reduced further, to the range of about 300 g. Changes in centrifugation speed can be programmed in the software to automatically initiate by timers in the software or signals generated by movement of the valve mechanisms.

Another alternative, exemplary embodiment of a centrifuge 100 constructed in accordance with this invention is shown in FIG. 34. That centrifuge is also arranged for separation, concentration and collection of select constituents of a biologic liquid mixture (such as, but not limited to, blood) and basically comprises two main assemblies, namely, a removable disk-shaped rotating assembly 112 and a housing 113. The housing contains the rotating assembly, a drive motor 126 and associated electrical drive circuits (not shown) and switches (not shown). The removable disk-shaped rotating assembly 112 basically comprises a separation chamber 143, and, in this exemplary case, two collection chambers 109 and 110 for receipt of separated constituents. In particular, in the exemplary embodiment depicted, the rotating assembly comprises a first or outer collection chamber 110 for the collection of higher specific gravity fluids, e.g., RBCs and a second or inner collection chamber 109 for the collection of lower specific gravity fluids, e.g., plasma. Each of these chambers is annular in shape, but could be of a different shape, so long as the rotating assembly was constructed to be balanced to prevent unbalance-induced vibration. A cover 101 encloses the rotating assembly 112 when the centrifuge is running. In this embodiment, it is envisioned that the housing 113, with its various internal components would be reusable inasmuch as it would not directly come into contact with the biologic liquid mixture. The removable rotating assembly 112, in contradistinction may be considered disposable after use.

The three chambers of the rotating assembly 112 are made up from several components, including a main body 108 having an extending hub 127, a cover plate 105, and a valve plate 115. These three components are secured together to provide leak-proof seals at all the interfaces. Alternatively, these components may be of unitary construction and formed as a single piece, using various manufacturing techniques, including, for example, stereolithography or casting. The fixed valve plate 115 is fixedly secured to the extending hub 127, so that a rotational force applied to the hub will result in the rotation of the rotational assembly. The rotating assembly also features an access port in the form of a pierceable membrane 144 located in the cover plate 105 to serve as the means for introduction of the biologic liquid mixture into the separation chamber 143, for processing. The access port can be of any suitable construction, e.g., a one-way duckbill valve. The access port may also serve as the means for removal of any residual separated component of the biologic mixture, e.g., the buffy coat if the biologic mixture is blood.

In operation, fluid flow between the separation chamber 143, and the collection chambers 110 and 109, is controlled by valves 138 and 117 (to be described later) that can be actuated independently, to selectively open and close, in order to control the flow of fluid therethrough. The valves are in fluid communication with the interior of the separation chamber via fluid passageways 141, 140 and 106, and will thus rotate as part of the rotating assembly. The fluid passageway 140 constitutes a channel between the underside of the top plate 105 and the body 108 and is in fluid communication with the interior of the separation chamber 143. The passageway 141 is in fluid communication with passageway 140. The passageway 140 is annular in shape and is in fluid communication with the valve 138 which is located at the passageway's terminus. It should be pointed out at this juncture that the passageway 140 need not be of annular shape. If not annular in shape, the rotating assembly should include either a similarly shaped passageway diametrically opposed to the passageway 140 or something else to balance the assembly so that will not vibrate upon rotation. The fluid passageway 106 is also in fluid communication with the interior of the separation chamber 143, but at a smaller radial distance than the fluid passageway 141. The passageway 106 is in fluid communication with the valve 117, which is located at the passageway's terminus. The passageway 106 is not annular in shape, but rather constitutes a bore. Preferably, a similar passageway is located diametrically opposed to the passageway 106 to result in a balanced assembly. If desired the passageway 106 could be annular.

As will be explained, the valves 138 and 117 feature elements that are static and dynamic relative to the other elements of the rotating assembly. The static elements are fixed with respect to the rotating assembly while the dynamic elements are arranged to shift or pivot, relative to the rotating assembly.

As shown in FIG. 34, and in expanded detail in FIGS. 35 and 37, each of the valves 138 and 117 is a 2-way (on/off) valve. Each valve includes a common valve plate 115 which forms the static (stationary) portion of each valve. The movable (slidable) portion of each valve is in the form of an arcuate section or segment of a common valve slider 116 (FIG. 37). Each valve is arranged so that when in its open position it permits fluid flow through it into its respective collection chamber. In particular, when open, the valve 138 permits fluid to flow through it into the collection chamber 110. Similarly, when open, the valve 117 permits fluid to flow through it into the collection chamber 109. Thus, the valves enable the controlled transfer of separated constituents of the biologic liquid mixture from the separation chamber 143 to the collection chambers 110 and 109.

To ensure leak proof operation, the valves employ resilient sealing materials between the respective parts of the valve that oppose each other and slide or pivot relative to each other. In particular, as clearly shown in FIG. 35, which represents the construction of each of the valves 138 and 117, the static portion of each valve, i.e., the valve plate 115, houses two O-rings 146 in respective circular recesses in the valve plate 115. Two pillars 147 and 148, which are integral with the valve plate 115, project downward therefrom. The pillars cooperate with a support guide cover 152 which is fixedly secured to each pillar to define a slot therebetween. The cross section of the slot is designated by "abcd" (see FIG. 35). The slot abcd of each valve extends below the valve plate 115, parallel to the plane of the valve plate and is arranged to slidably receive therein a respective arcuate segment of the common valve slider 116. In particular, the slot of valve 138 slidably receives the arcuate segment 154 (FIG. 37) of the valve slider 116, while the slot of the valve 117 slidably receives the arcuate segment 153 of the valve slider. The valve slider 116 is arranged to be pivoted about the central longitudinal axis (the rotation axis X shown in FIGS. 34 and 37) of the rotating assembly 112 to operate (i.e., open and close) the valves 138 and 117 as will be described later.

As best seen in FIG. 35, the valve plate 115 includes an entrance port or hole 182 and an exit port or hole 183 for each valve. The ports 182 and 183 extend through the associated portion of the valve plate into fluid communication with the slot abed located therebelow. Each valve includes a seal plate 150 which is fixedly secured to the underside of its associated arcuate segment 153 or 154 and is located within the slot abed of that valve. The arcuate segment 154 of the valve slider 116 includes a pair of drillings or holes 149 bridged by a transverse slot 151. The two drillings 149 of the arcuate segment 154 are arranged to be brought into alignment and fluid communication with the ports 182 and 183 of the valve 138 when the valve slider 116 is pivoted in one rotational direction about the axis X. Similarly, the two drillings 149 of the arcuate segment 153 are arranged to be brought into alignment and fluid communication with the ports 182 and 183 of the valve 117 when the valve slider 116 is pivoted in the opposite rotational direction about the axis X. Accordingly, when the valve slider 116 is pivoted to the position aligning its drillings 149 with the ports 182 and 183 of the valve 138 the higher specific gravity fluid that is separated by the centrifugation is permitted to flow from the separation chamber 143 through the channel 141 down the passageway 140 into port 182. From there that fluid flows through the transverse slot 151 to the exit port 183 from whence it flows into the chamber 110. When the valve slider 116 is pivoted to the position aligning its drillings 149 with the ports 182 and 183 of the valve 117 the lower specific gravity fluid that is separated by the centrifugation is permitted to flow from the separation chamber 143 through the passageway 106 into port 182. From there that fluid flows through the transverse slot 151 to the exit port 183 from whence it flows into the chamber 109.

The dimension of the slot abed are selected to provide appropriate compression to O-rings 146 to prevent leakage when the arcuate slider segments 153 and 154 slide through to open and close the valves.

Since the valves 138 and 117 are part of the rotating assembly, a force translating mechanism is provided to effect the actuation of the valves, while the device is in operation. This force translation may be accomplished using various techniques known to those skilled in the art. One exemplary force transfer mechanism suitable for use in the device will now be described.

In order to enable the valve slider to be pivoted in the two rotational directions about axis X with respect to the valve plate 115, a pair of components with helical teeth are provided. Those components are arranged to be moved axially relative to each other as best seen in FIG. 36, all while rotating to create a centrifugal field for the separation of the biologic liquid mixture. Referring to FIG. 34, it can be seen that the chamber body 108 has male axial splines 121 incorporated on the extending hub 127. A translator, 122 having female splines slides axially on the male splines 121 of the extending hub 127. The translator includes helical teeth 120 on its exterior. A valve slider hub 184 has inner helical teeth 118 that mate with the exterior teeth 120 on the translator. The translator 122 is moved axially via ball bearing 130 by the axial motion of a sleeve 132. That sleeve is keyed with slots 137 in portions of housing 113. The sleeve 132 is driven axially in turn by cams 124 formed on the interior of a control sleeve 136. The control sleeve 136 is arranged to be rotated, driven by tabs 134. The tabs pass through slots in the housing 113. The control sleeve 136 has three positions, with the middle position corresponding to the valve plate positions shown in FIG. 37. As the control sleeve 136 is rotated, the sleeve 132 riding on cams 124 creates an axial motion, which the translator 122 converts to a rotary motion, which in turn effects the pivoting of the valve slider 116, so as to direct the actuation of the valves. A return spring (not shown) biases the valve plate 115 in torsion, such that the translator 122 is driven toward the motor 126.

The entire removable rotating assembly 112 mounts on the drive shaft 123 of the motor 126, and is held in place by wing nut 103. The rotation of the rotating assembly 112 is driven by the motor 126 and an associated driveshaft 123 through a key 104. The driveshaft 123 is located by ball bearing 145 and the motor drive end 125. The motor 126 is mounted on a frame 128 that also locates the ball bearing 145.

In operation of the device 100, the control sleeve 136 is placed in the central position, controlled by detents (not shown). A new removable rotating assembly 112 is placed over the drive shaft 123 and pressed down to compress the return spring (not shown) and thus position the valve plate 115 in its starting position, that is with the two valve slots 151 in the position shown in FIG. 37. The wing nut 103 is then spun onto threaded portion 102 of driveshaft 123, to hold the removable rotating assembly 112 in place. A charge of fluid (the biologic liquid mixture, e.g., blood) for separation is injected into chamber 143 via membrane 144. The motor 126 is turned on and allowed to run at a speed appropriate for separation of the biologic liquid mixture into its several constituent layers as concentric layers within the separation chamber 143. At adequate rotational speeds, this separation will occur in approximately ninety seconds or less, more typically about one minute. For mixtures with very similar specific gravities, this time period may be extended. Once separation of the constituents has occurred, the tab 134 is moved into a second position, to pivot the valve slider 116 in one rotational direction about the axis X to the position such that one of the holes 149 in the first valve 138 aligns with the entrance port 182 and the other of the holes 149 aligns with the exit port 183, thereby opening that valve so that the high specific gravity fraction of the biologic liquid mixture flows into chamber 110 through first valve 138.

In accordance with one preferred embodiment of this invention, the interface created by the separation of the biologic liquid mixture into fractions is visually detectable, such that it may be observed through a transparent portion in the top plate 105. Alternatively, the interface may be detected electronically, using sensors as has been discussed previously. It is recognized that there may be a benefit in providing a contrasting color, or mirrored surface, over at least a portion of the rotating chamber disposed opposite a detector, or opposite to the transparent portion of the top plate of the rotating assembly, in order to enhance the detectability of the interface by the operator or detector.

The movement of the interface is monitored as the higher specific gravity constituent flows into chamber 110. As this interface approaches the entrance 142 to channel 141, and when the interface reaches a predetermined point, relative to the entrance 142 into channel 141, the fluid flow through first valve 138 is halted, such as by acting upon the tab 134 to trigger the closing of the first valve 138. Though the time for the evacuation of the higher specific gravity fluid will vary based upon the speed of the rotation, the viscosity of the fluid, and the diameter of the most restrictive portion of the flowpath, it is anticipated that this will typically be after approximately 15 seconds of flow. Where the operator is detecting the interface, and monitoring in order to determine when to close the first valve, it is necessary that the rate of movement of the interface is such that a person may have adequate time to react and trigger the closing of the valve, as has been discussed previously.

Subsequently, the tab 134 is then moved to a third position, which then pivots the valve slider 116 in the opposite rotational direction about axis X to the position such that one of the holes 149 in the second valve 117 aligns with the entrance port 182 and the other of the holes 149 aligns with the exit port 183, thereby opening that valve so that lower specific gravity fraction of the biologic liquid mixture flows into chamber 109 through the second valve 117. This flow continues until air enters passageway 106, whereupon flow ceases. At this juncture, typically about 2-3 minutes into the procedure, the tab 134 is returned to its original, first position, with both valves 138 and 117 now closed, and the motor is de-energized. A predetermined volume of the lower specific gravity constituent, together with the remains of any intermediate specific gravity constituents (e.g., buffy coat, if the biologic mixture is blood), are now trapped in the separation chamber 143, and ready for removal for use, for example, by directing a syringe into the separation chamber via membrane 144. The removable rotating assembly 112 may then be separated from the driveshaft 123, and the contents of one or more of the three chambers 143, 108, and 109 can be harvested if desired (via membrane and syringe, for example).

As will be appreciated by those skilled in the art, in order to function properly, the device 100 incorporates one or more vents (not shown) to allow for fluid displacement. Ideally, one of the vents provides for air to enter the chamber 143 as the fluid flows into chambers 109 and 110, and another two vents allow air to escape as fluid flows into chambers 109 and 110.

In an embodiment of the centrifuge 100, it may be desirable to provide for the separation of a biologic liquid mixture, e.g., blood, charge of approximately 30 mL. To that end the above described rotating assembly 112 may be sized with a maximum diameter of approximately 8 cm, and a height measured along the longitudinal axis (the rotation axis X) of approximately 1 cm. It is recognized that increasing or decreasing the dimensions may be desirable in order to achieve a desired sample size for processing.

As has been discussed previously, it is recognized that the chambers of the device depicted in FIGS. 34-37, may be either annular chambers, or alternatively, may be a plurality of linked chambers forming two or more sections of a circle, or alternatively, two or more vessels may be balanced to allow rotation of the multiple chambers, collectively forming a rotor, where each of the chambers provides for discharge of particular blood components (e.g., RBC and Plasma), while allowing for the concentration and access to the desired blood component concentrated in each of the chambers.

In any of the embodiments described herein, the device may benefit from the incorporation of a tilt sensor that would halt the rotation, or at a minimum reduce the rotation speed, of the chamber, should the device be toppled or operated at an undesirable angle. Given the rotation speed that the device is expected to operate under, the angle would not likely affect the stratification of the fluid components, but rather, this would prevent unintended movement, that is known with devices that include rotating elements, or those prone to vibrate while in operation.

The above described embodiments may be made available in kit form, including the device and accessories needed for operation of the device, including instructions for use and packaging suitable for storage and preserving sterility. In some instances, the kit may provide instructions along with the centrifuge device (either as a single unit, or separable components), and optionally including accessories such as separation aids, including focusing fluids, or rapid test kits useful for providing qualitative or quantitative information regarding the concentrated product. Various blood testing procedures are known in the art, but it is anticipated that any rapid testing kit that provides useful information regarding, for example, the concentration factor or recovery efficiency of the concentrated products may be incorporated into the kit. Such a kit may require comparing the results for blood components that have been subjected to the rapid test kit after concentration, and optionally prior to concentration. It is envisioned that the accessories may be contained within a separate container within the packaging, or contained within the blood separation chamber during packaging, or made available apart from the centrifuge unit. For the embodiment providing a reusable drive component with a motor that is arranged to be coupled to a disposable centrifuge component, the kit may include multiple disposable centrifuge components each suitable for use with the reusable drive component.

Thus since the inventive process and inventions disclosed herein may be embodied by additional steps or other specific forms without departing from the spirit of general characteristics thereof, some of which steps and forms have been indicated, the embodiments described herein are to be considered in all respects illustrative and not restrictive. The scope of the invention is to be indicated by the appended claims, rather than the foregoing description, and all changes which come within the meaning and range of equivalency of the claims are intended to be embraced therein.

What is claimed is:

1. A centrifuge comprising:
   a) a chamber comprising:
      (i) a barrel having a longitudinal axis, and a second end and a first end, with a side wall extending therebetween, wherein said first end has a diameter smaller than a diameter of said second end;
      (ii) said second end of said barrel being arranged to be selectively closed off;
      (iii) a first port provided in said chamber at a first radial distance from said longitudinal axis, and in fluid communication with a first valve;
      (iv) a second port provided in said chamber at a second radial distance from said longitudinal axis, and in fluid communication with a second valve, with said second radial distance being less than said first radial distance; and
      (v) at least a portion of said chamber being transparent;
   b) a motor to rotate said chamber about said longitudinal axis, thereby producing a centrifugal field.

2. The centrifuge of claim 1, further comprising a biologic liquid mixture of at least two constituents having different specific gravities, said chamber containing said biologic liquid mixture, and where each of said first and second valves are independently selectively openable, such that while said first port is opened, at least a portion of said first constituent is automatically ejected out of said first port as a result of pressure built up by said centrifugal field, and while said second port is opened, at least a portion of a second constituent is automatically ejected out of said second port as a result of pressure built up by said centrifugal field.

3. The centrifuge of claim 1, wherein said side wall extends in a taper from said second end to said first end.

4. The centrifuge of claim 1, wherein said side wall extends in a uniform taper from said second end to said first end.

5. The centrifuge of claim 1, wherein said barrel is a frustum of a cone, and tapered with respect to said longitudinal axis.

6. The centrifuge of claim 1, additionally comprising an end cap for selectively closing off said second end of said barrel, said first port being in fluid communication with said first valve by a first passageway, and said second port being in fluid communication with said second valve by a second passageway, and wherein each of said first and second passageways extend through said end cap to the exterior of said chamber.

7. The centrifuge of claim 6, further comprising a valve cap that is slidably fit over said end cap, said valve cap having a first outlet port and a second outlet port, wherein said end cap and valve cap are movable relative to each other, such that for said first valve, said first passageway can be brought into alignment with said first outlet port in said valve cap in order to selectively enable the flow of a fluid therethrough, and for said second valve, said second passageway can be brought into alignment with said second outlet port in said valve cap in order to selectively enable the flow of a fluid therethrough.

8. The centrifuge of claim 7, wherein said movement of said end cap and valve cap relative to each other is responsive to a signal.

9. The centrifuge of claim 8, wherein said signal is derived from one of: observing an interface occurring between separated constituents of a biologic liquid mixture; detecting an interface occurring between separated constituents of a biologic liquid mixture by at least one automatic detector; and an automatic response after passage of a defined period of time.

10. The centrifuge of claim 1, wherein said chamber further comprises an annular wedge located within said barrel and projecting from said end cap, said annular wedge having a side wall located adjacent said wall of said barrel to define therebetween a circumferential channel.

11. The centrifuge of claim 1, further comprising a reusable component and a disposable component, said disposable component being releasably securable to said reusable component, and wherein said reusable component comprises said motor and said disposable component comprises said chamber.

12. The centrifuge of claim 1, further comprising an inlet for the addition of a biologic liquid mixture into said chamber.

13. The centrifuge of claim 1, further comprising a vent to permit air to enter said chamber.

14. The method of isolating and concentrating a fraction of a biologic liquid mixture, comprising the steps of:
   a. providing a centrifuge comprising:
      i. a chamber comprising a barrel having a longitudinal axis, a first end, a second end, and a sidewall extending between said second end and said first end, wherein said first end has a diameter smaller than the diameter of said second end and wherein at least a portion of said chamber is transparent,
      ii. said second end of said barrel being arranged to be selectively closed off,
      iii. a first port provided in said chamber at a first radial distance from said longitudinal axis, and in fluid communication with a first valve,
      iv. a second port provided in said chamber at a second radial distance from said longitudinal axis and in fluid communication with a second valve, with said second radial distance being less than said first radial distance,
      v. a motor to rotate said chamber about the longitudinal axis;
   b. introducing an entire volume of said biologic liquid mixture into said chamber;
   c. rotating said chamber about said longitudinal axis, and separating said biologic liquid mixture by specific gravity into a first fraction and a second fraction;
   d. selectively opening said first valve to eject at least a portion of said first fraction from said chamber through said first port, thereby leaving a residual of said biologic liquid mixture in said chamber; and
   e. selectively opening said second valve after the opening of said first valve, to eject at least a portion of said residual of said biologic liquid mixture from said chamber through said second port.

15. The method of claim 14 further comprising:
   f. collecting at least a portion of said biologic liquid mixture remaining within said chamber.

16. The method of claim 14 further comprising between step d and step e, monitoring an interface between said first fraction and said second fraction through said wall, said wall being transparent.

17. The method of claim 16, wherein said monitoring of said interface is one of: observing an interface occurring between separated constituents of a biologic liquid mixture; and detecting an interface occurring between separated constituents of a biologic liquid mixture by at least one automatic detector.

18. The method of claim 14 further comprising between step d and step e, the step of selectively closing said first valve.

19. The method of claim 14 wherein said biologic liquid mixture is one of blood, bone marrow aspirate, and combinations thereof.

20. The method of claim 18, wherein said biologic liquid mixture is blood, and said first fraction comprises a red blood cell fraction, and said second fraction comprises a plasma fraction.

21. The method of claim 20, said biologic liquid mixture further comprising platelet rich plasma.

22. The method of claim 14, wherein said biologic liquid mixture is blood, and said separation of said fractions results in one or more of: at least a 6.3 platelet concentration factor; at least 87% platelet recovery; and at least 92% of red blood cells removed from said biologic liquid mixture.

\* \* \* \* \*